United States Patent
Sano et al.

(10) Patent No.: US 7,097,990 B2
(45) Date of Patent: Aug. 29, 2006

(54) METHOD OF SCREENING CELL DEATH INHIBITOR

(75) Inventors: Yorikata Sano, Tsukuba (JP); Kohei Inamura, Tsukuba (JP); Akira Miyake, Tsukuba (JP); Hiromichi Yokoi, Tsukuba (JP); Katsura Nozawa, Tsukuba (JP); Shinobu Mochizuki, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/492,477

(22) PCT Filed: Aug. 8, 2002

(86) PCT No.: PCT/JP02/08128

§ 371 (c)(1),
(2), (4) Date: Apr. 12, 2004

(87) PCT Pub. No.: WO03/033727

PCT Pub. Date: Apr. 24, 2003

(65) Prior Publication Data

US 2004/0235069 A1 Nov. 25, 2004

(30) Foreign Application Priority Data

Oct. 12, 2001 (JP) ............................. 2001-315339
Jan. 30, 2002 (JP) ............................. 2002-21175

(51) Int. Cl.
- *C07K 14/705* (2006.01)
- *G01N 33/68* (2006.01)
- *C12N 15/12* (2006.01)
- *C12N 15/63* (2006.01)
- *C12N 15/79* (2006.01)
- *C12N 15/85* (2006.01)

(52) U.S. Cl. ................ 435/7.21; 435/69.1; 435/320.1; 435/252.3; 536/23.5; 530/350

(58) Field of Classification Search .................... 435/4, 435/69.1, 320.1, 325, 252.3, 254.2
See application file for complete search history.

(56) References Cited

U.S. PATENT DOCUMENTS

| | | | | |
|---|---|---|---|---|
| 5,194,596 A | * | 3/1993 | Tischer et al. | 530/399 |
| 5,350,836 A | * | 9/1994 | Kopchick et al. | 530/399 |
| 6,451,602 B1 | * | 9/2002 | Popoff et al. | 435/375 |
| 6,548,272 B1 | * | 4/2003 | Shimizu et al. | 435/69.1 |
| 2002/0182635 A1 | * | 12/2002 | Penner et al. | 435/7.1 |

FOREIGN PATENT DOCUMENTS

| | | |
|---|---|---|
| EP | 1 048 727 A1 | 11/2000 |
| WO | WO 99/35158 A1 | 7/1999 |
| WO | WO 00/40614 A3 | 7/2000 |
| WO | WO 00/65056 A2 | 11/2000 |
| WO | WO 02/38608 A2 | 5/2002 |
| WO | WO 02/072824 A2 | 9/2002 |
| WO | WO 02/076488 A1 | 10/2002 |
| WO | WO 02/095010 A2 | 11/2002 |
| WO | WO 02/102994 A2 | 12/2002 |
| WO | WO 03/004622 A2 | 1/2003 |
| WO | WO 03/025130 A2 | 3/2003 |
| WO | WO 03/038063 A2 | 5/2003 |
| WO | WO 03/073983 A2 | 9/2003 |

OTHER PUBLICATIONS

Kandel, E.R., Schwartz, J.H., and Jessell, T. Principles of Neural Science. Third Edition, 1991. New York: Elsevier Science Publishing Co., Inc.*

Hille, B. Ionic Channels of Excitable Membranes. Second Edition, 1992. Sunderland, MA: Sinauer Associates.*

Hopp, T.P. and Woods, K.R. (1981). Prediction of protein antigenic determinants from amino acid sequences. Proceedings of the National Academy of Sciences USA 78:3824-3828.*

Vukicevic, S., Kopp, J.B., Luyten, F.P., and Sampath, T.K. 1996. Induction of nephrogenic mesenchyme by osteogenic protein 1 (bone morphometric protein 7). Proceedings of the National Academies of Sciences U.S.A. 93: 9021-9026.*

Alberts, B, Bray, D, Lewis, J, Raff, M, Roberts, K, Watson, JD. 1994. Molecular Biology of the Cell. Third Edition. New York: Garland Publishing, Inc.*

GenBank accession No. Q91YD4.*

Smith S. 2001. The world according to PARP. Trends in Biochemical Sciences 26:174-179.*

Hille, B. Ionic channels of excitable membranes. 1992. Sunderland, MA:Sinauer Associates, pp. 4-19.*

(Continued)

*Primary Examiner*—Robert C. Hayes
*Assistant Examiner*—Daniel E. Kolker
(74) *Attorney, Agent, or Firm*—Sughrue Mion, PLLC

(57) ABSTRACT

There is provided a method of screening for substance that inhibits cell death induced by activation of PARP, particularly a substance that is useful as a therapeutic and/or preventive agent for rheumatoid arthritis, neuronal death at the time of cerebral ischemia, cell death of the heart after myocardial infarction reperfusion, autoimmune destruction of β-cells of pancreatic islets of Langerhans, cell death after shock, or inflammatory reaction by immunocyte death. Also provided are a novel protein and a novel gene encoding the same. The aforementioned screening method comprises a step of allowing a test substance to contact a cell expressing an LTRPC2 protein under a conditions such that the LTRPC2 protein can be activated, and a step of analyzing inhibition of LTRPC2 protein activation. The aforementioned novel protein is a rat or mouse LTRPC2 protein, and the aforementioned novel gene is a rat or mouse LTRPC2 gene.

17 Claims, No Drawings

OTHER PUBLICATIONS

Marshall "Gene Therapy's Growing Pains". Science, vol. 269 (1995), pp. 1050-1055.*

Verma I.M. et al. 1997. Nature 389:239-242.*

Orkin S.H. et al. 1995. "Report and Recommendations of the Panel to Assess the NIH Investment in Research on Gene Therapy".*

Laniel 2001. Journal of Biological Chemistry 276:20766-20773.*

Shackelford 2000. Free Radical Biology and Medicine 28:1387-1404.*

NCBI locus AJ344343.*

Schendel 1998. Current Protocols in Molecular Biology 16.1.1-16.1.3.*

UniProt Accession No. Q91YD4.*

Feng Qian et al., "Candidates for Nonselective Cation Channels and Store-Operated Channels in Insulin-Secreting Cells", Diabetes, 2002, vol. 51, Supplement 1, pp. 8183-8189.

Edith Wehage et al., "Activation of the Cation Channel Long Transient Receptor Potential Channel 2 (LTRPC2) by Hydrogen Peroxide", Journal of Biological Chemistry, 2002, vol. 277, No. 26, pp. 23150-23156.

Anne-Laure Perraud et al., "ADP-ribose gating of the calcium-permeable LTRPC2 channel revealed by Nudix motif homology", Nature, 2001, vol. 411, No. 6837, pp. 595-599.

"The 73$^{rd}$ Annual Meeting of The Japanese Pharmacological Society Mar. 23-25, 2000 Y okohama Japan", The Japanese Journal of Pharmacology, 2000, vol. 82, Supplemental I, p. 83.

Yorikata Sano et al., "Immunocyte $Ca^{2+}$Influx System Mediated by LTRPC2", Science, 2001, vol. 293, No. 5533, pp. 1327-1330.

Kentaro Nagamine et al., "Molecular Cloning of a Novel Putative $Ca^{2+}$Channel Protein (TRPC7) Highly Expressed in Brain", Genomics, 1998, vol. 54, pp. 124-131.

Yuji Hara et al., "LTRPC2 $Ca^{2+}$-Permeable Channel Activated by Changes in Redox Status Confers Susceptibility to Cell Death", Molecular Cell, 2002, vol. 9, pp. 163-173.

International Search Report dated Sep. 5, 2002.

Feng Qian et al., "Candidates for Nonselective Cation Channels and Store-Operated Channels in Insulin-Secreting Cells", Diabetes, 2002, vol. 51, Supplement 1, pp. S183-S189.

* cited by examiner

METHOD OF SCREENING CELL DEATH INHIBITOR

This is a National Stage of International Application No. PCT/JP02/08128, filed Aug. 8, 2002.

TECHNICAL FIELD

This invention relates to a method for screening a cell death inhibitor. Also, the present invention relates to novel rat LTRPC2 and mouse LTRPC2.

BACKGROUND OF THE INVENTION

Poly-ADP-ribose polymerase (PARP) existing in the nucleus is an enzyme which is activated by DNA degradation caused by inducible nitrogen oxide, oxygen radical and the like and thereby effects addition of the ADP ribose moiety of nicotinamide adenine dinucleotide (NAD) to nuclear protein and DNA. That is, a DNA damage activates PARP to cause addition of a large amount of ADP ribose to histone and PARP itself while consuming ATP. It is considered that intracellular NAD and ATP are reduced as the result to cause cell death due to intracellular energy depletion (Zhang, J. and Snyder, S. H., Science, 263, 687–689, 1995). Five genes coding for the PARP protein have so far been reported, and it is considered that the PARP activity is expressed through functioning of these genes. Among these genes, PARP-1 gene is the gene analyzed in most detail and is considered to be a gene having the most high contribution to the cell death accompanied by the activation of PARP protein (Smith, S., Trends Biochem. Sci., 26174–179, 2001).

It has been reported that NAD depletion by a DNA damage in cells of pancreatic islets of Langerhans does not occur in a PARP gene-deleted mutant mouse (Heller, B. et al., J. Biol. Chem., 270, 11176–11180, 1995). In addition, according to another reference, it has been revealed that the NAD depletion by a DNA damage does not occur also in cerebral cortex neuron in the aforementioned mutant mouse, and it has been reported that the cerebral infarction range accompanied by transient cerebral ischemia is significantly reduced in this mouse (Eliasson, M. J. et al., Nature Med., 3, 1089–1095, 1997). Thus, it is known that the cell death induced by the activation of PARP causes serious diseases in tissues of the living body. Also known as diseases in which the cell death induced by the activation of PARP is concerned include neuronal death at the time of cerebral ischemia, cell death of the heart after myocardial infarction reperfusion, autoimmune destruction of β-cells of pancreatic islets of Langerhans in type I diabetes mellitus, cell death after shock, inflammatory reaction by immunocyte death, and rheumatoid arthritis as an autoimmune disease which onsets by the generation of an abnormality in immune functions (Eliasson, M. J. et al., Nature Med., 3, 1089–1095, 1997; Zingarelli, B., Salzman, A. L. and Szabo, C., Circ. Res., 83, 85–94, 1998; Burkart, V. et al., Nature Med., 5, 314–319, 1999; Pieper, A. A. et al., Proc. Natl. Acad. Sci., 96, 3059–3064, 1997; Szabo, C., Cuzzocrea, S., Zingarelli, B., O'Connor, M. and Saltzman, A. L., J. Clin. Invest., 100, 723–735, 1997; Oliver F. J. et al., EMBO J., 18, 4446–4454, 1999; Szabo, C. et al., Proc. Natl. Acad. Sci., 95, 3867–72, 1998).

On the other hand, it is known that N-methyl-N'-nitro-N-nitrosoguanidine (MNNG) or $H_2O_2$ causes cell death by activating PARP (Halappanavar, S. S. et al., J. Biol. Chem., 274, 37097–37104, 1999; Watson, A. J., Askew, J. N. and Benson, R. S., Gastroenterology, 109, 472–482, 1995), and it is known that 3,4-dihydro-5-[4-(1-piperidinyl)butoxy]-1 (2H)-isoquinolinone (DPQ), 3-aminobenzamide or nicotinamide inhibits cell death caused by PARP through the inhibition of the activation of PARP (Takahashi, K. et al., Brain Res., 829, 46–54, 1999; Watson, A. J., Askew, J. N. and Benson, R. S., Gastroenterology, 109, 472–482, 1995)).

However, the presence of a factor existing in the downstream of PARP has not been clarified yet, and it is not clear at present about the cell death-inducing mechanism of the PARP activation.

On the other hand, a human LTRPC2 (long transient receptor potential channel 2) gene was obtained in 1998 (Genomics, 54, 1, 124–131, 1998). Regarding a mouse LTRPC2 gene, there are reports stating that it was obtained (Japanese Journal of Pharmacology, Suppl. 1, 83, 2000, Molecular Cell, 9, 163–173, 2002), but its actual nucleotide sequence has not been reported. In addition, information on a rat LTRPC2 has not been reported. It has been revealed that the human LTRPC2 gene is activated by intracellular ADP ribose or NAD and functions as a calcium permeable non-selective cation channel (Sano, Y. et al., Science, 293, 1327–1330, 2001). Though it has been suggested that the controlling mechanism of LTRPC2 by ADP-ribose may have an important role in cellular functions (Nature, 411, 6837, 595–599, 2001), it is not clear about the functioning mechanism of LTRPC2 in cells and its subsequent influence upon the cells.

In addition, expression of the LTRPC2 gene in a cell prepared by cloning an immunocyte has been revealed, but its expression in actual human blood, particularly in immunocyte-containing lymphocyte, is not clear.

As has been described in the above, the fact itself that activation of PARP induces cell death is known, but the presence of a factor existing in the downstream of PARP is not clarified and its mechanism is unclear. Thus, great concern has been directed toward a method for screening a substance capable of inhibiting cell death induced by the activation of PARP, particularly a substance which is useful as a therapeutic agent and/or a preventive agent for a disease in which cell death induced by the activation of PARP is concerned (e.g., rheumatoid arthritis, neuronal death at the time of cerebral ischemia, cell death of the heart after myocardial infarction reperfusion, autoimmune destruction of β-cells of pancreatic islets of Langerhans, cell death after shock, or inflammatory reaction by immunocyte death).

DISCLOSURE OF THE INVENTION

As a result of extensive studies, the present inventors have found for the first time that activation of the LTRPC2 protein is regulated by the activation of PARP and has a function to induce cell death. In addition, it was found also for the first time that the LTRPC2 gene is expressed in human lymphocyte and that its expression level is increased in rheumatoid arthritis.

More illustratively, as shown in Example 6 which is described later, activation of LTRPC2 protein was observed when a substance known as the activator of PARP, namely MNNG or $H_2O_2$, was added to a cell in which the LTRPC2 protein was expressed. In addition, as shown in Example 7, when DPQ, 3-aminobenzamide or nicotinamide as a PARP inhibitor was added together with a PARP activator (e.g., MNNG or $H_2O_2$), activation of the LTRPC2 protein was significantly inhibited.

Further, as shown in Example 10, cell death by a PARP activator $H_2O_2$ was accelerated in a cell in which the LTRPC2 protein was expressed.

Also, as shown in Example 2, the LTRPC2 gene was frequently expressed in lymphocyte carrying an immune function and, as shown in Example 12, the expression level of the LTRPC2 gene was increased in a model animal of rheumatoid arthritis as one of immune diseases.

In addition, as shown in Example 17, it was found that the LTRPC2 protein accelerates cell death by streptozotocin stimulation as a type I diabetes mellitus model.

Accordingly, by selecting a substance which inhibits activation of the LTRPC2 protein, a substance capable of inhibiting cell death induced by the activation of PARP can be identified, and furthermore, a substance useful as a therapeutic drug for a disease caused by cell death, for example, a therapeutic drug for rheumatoid arthritis as an immune disease, neuronal death after cerebral ischemia or autoimmune destruction of β-cells of pancreatic islets of Langerhans in type I diabetes mellitus, can be found out. The present invention provides a screening system based on these findings.

Accordingly, the present invention relates to (1) a method for screening a substance useful for inhibiting cell death, characterized in that it comprises a step of allowing a substance to be tested to contact with a cell expressing a polypeptide consisting of the amino acid sequence represented by SEQ ID NO:2, SEQ ID NO:4 or SEQ ID NO:14 or a variation functionally equivalent thereof, under such a condition that the aforementioned polypeptide or a variation functionally equivalent thereof can be activated, and a step of analyzing inhibition of the activation of the aforementioned polypeptide or a variation functionally equivalent thereof, (2) a process for producing a pharmaceutical composition for cell death inhibition, characterized in that it comprises a step of carrying out screening using the screening method described in (1), and a step of preparing a pharmaceutical preparation using a substance obtained by the aforementioned screening, (3) (i) a polypeptide which comprises the amino acid sequence represented by SEQ ID NO:4 or SEQ ID NO:14 and also exhibiting the LTRPC2 protein activity, or (ii) a polypeptide which comprises an amino acid sequence in which one or several amino acids in the amino acid sequence represented by SEQ ID NO:4 or SEQ ID NO:14 are substituted, deleted and/or inserted and also exhibiting the LTRPC2 protein activity (with the proviso that a polypeptide consisting of the amino acid sequence represented by SEQ ID NO:2 is excluded), (4) a polypeptide which consists of the amino acid sequence represented by SEQ ID NO:4 or SEQ ID NO:14, (5) a polynucleotide which encodes the polypeptide according to (3) or (4), (6) a vector which comprises the polynucleotide according to (5), (7) a cell which comprises the vector according to (6), and (8) a process for producing the polypeptide according to (3) or (4), characterized in that it comprises a step of culturing the cell according to (7).

BEST MODE FOR CARRYING OUT THE INVENTION

The following describes the present invention in detail.

Both of apoptosis and necrosis are included in the term "cell death" as used herein. Apoptosis is a programmed cell death which is a cell death positively induced by the cell itself under a physiological condition. On the other hand, necrosis indicates death of a part of the living body and is a cell death induced by force under a non-physiological condition.

[1] Polypeptide and Polynucleotide of the Present Invention

The polypeptides consisting of the amino acid sequences represented by SEQ ID NO:4 and SEQ ID NO:14 are natural type LTRPC2 proteins respectively derived from rat and mouse. The "polypeptide consisting of the amino acid sequence represented by SEQ ID NO:4 or SEQ ID NO:14" or a variation functionally equivalent thereof (with the proviso that a polypeptide consisting of the amino acid sequence represented by SEQ ID NO:2 is excluded) is in itself a novel polypeptide and included in the polypeptide of the present invention.

As the variation functionally equivalent of the "polypeptide consisting of the amino acid sequence represented by SEQ ID NO:4", for example, (1) a polypeptide which comprises the amino acid sequence represented by SEQ ID NO:4 and also shows the LTRPC2 protein activity;

(2) a polypeptide which comprises an amino acid sequence in which one or two or more, preferably from 1 to 5, more preferably from 1 to 3, further preferably one, of amino acids in the amino acid sequence represented by SEQ ID NO:4 are substituted, deleted and/or inserted and also shows the LTRPC2 protein activity;

(3) a partial fragment of a polypeptide which consists of the amino acid sequence represented by SEQ ID NO:4 and is also a partial fragment showing the LTRPC2 protein activity; or (4) a polypeptide which comprises an amino acid sequence having a homology of 84% or more (preferably 90% or more, more preferably 95% or more, further preferably 98% or more, and particularly preferably 99% or more) with the amino acid sequence represented by SEQ ID NO:4 and also shows the LTRPC2 protein activity, and the like may be exemplified.

Also, as the variation functionally equivalent of the "polypeptide consisting of the amino acid sequence represented by SEQ ID NO:14", for example, (1) a polypeptide which comprises the amino acid sequence represented by SEQ ID NO:14 and also shows the LTRPC2 protein activity;

(2) a polypeptide which comprises an amino acid sequence in which one or two or more, preferably from 1 to 5, more preferably from 1 to 3, further preferably one, of amino acids in the amino acid sequence represented by SEQ ID NO:14 are substituted, deleted and/or inserted and also shows the LTRPC2 protein activity;

(3) a partial fragment of a polypeptide which consists of the amino acid sequence represented by SEQ ID NO:14 and is also a partial fragment showing the LTRPC2 protein activity; or (4) a polypeptide which comprises an amino acid sequence having a homology of 84% or more (preferably 90% or more, more preferably 95% or more, further preferably 98% or more, and particularly preferably 99% or more) with the amino acid sequence represented by SEQ ID NO:14 and also shows the LTRPC2 protein activity, and the like may be exemplified.

The term "homology" as used herein means a value obtained using the bl2seq program (Tatiana A. Tatusova and Thomas L. Madden, *FEMS Microbiol. Lett.*, 174, 247–250, 1999) of a BLAST package [sgi 32 bit version, version 2.0.12; obtained from National Center for Biotechnology Information (NCBI)]. As parameters in this case, "blastp" is used as the "program name", and "0" as the "Gap insertion Cost value", "0" as the "Gap elongation Cost value" and "BLOSUM62" as the "Matrix", respectively, as the pairwise alignment parameters.

The term a polypeptide shows "LTRPC2 protein activity" as used in this specification means that it shows the same activity of the known human natural type LTRPC2 protein consisting of the amino acid sequence represented by SEQ ID NO:2, and it illustratively means an activity to cause permeation of ions as a result of the generation of a passage for ions by the aforementioned polypeptide by itself existing in the membrane, when a PARP activator is allowed to undergo the reaction for example under the co-expression of PARP.

In this specification, whether or not a polypeptide shows "LTRPC2 protein activity" is not particularly limited, but it can be verified for example by the following method (preferably the method described in Example 6). That is, a cell expressing PARP is transfected with an expression vector comprising a polynucleotide coding for the LTRPC2 protein. $^{86}Rb^+$ is incorporated in advance into the thus obtained cells and then a PARP activator is added thereto. Release of $^{86}Rb^+$ from the cells via the LTRPC2 protein formed as the result can be verified using a change in the radioactivity of $^{86}Rb^+$ in the extracellular moiety or inside the cells.

A polypeptide in which an appropriate marker sequence and the like are added to the N-terminus and/or C-terminus of the amino acid sequence represented by SEQ ID NO:4 or 14 (with the proviso that it must show the LTRPC2 protein activity) can be exemplified as the "polypeptide which comprises the amino acid sequence represented by SEQ ID NO:4 or 14 and also shows the LTRPC2 protein activity" as one of the variation functionally equivalents of the "polypeptide consisting of the amino acid sequence represented by SEQ ID NO:4 or 14". As the aforementioned marker sequence, a sequence for confirming expression of a peptide, for confirming intracellular localization or for easily carrying out purification and the like can be used, and its examples include FLAG epitope, hexa-histidine tag, hemagglutinin tag, myc epitope and the like.

Origin of the variation functionally equivalent of the "polypeptide consisting of the amino acid sequence represented by SEQ ID NO:4 or 14" is not limited to human, rat or mouse. For example, the aforementioned variation functionally equivalent include not only a natural allele mutant of the polypeptide consisting of the amino acid sequence represented by SEQ ID NO:4 or 14 in human, rat or mouse (with the proviso that it shows the LTRPC2 protein activity), or a polypeptide formed by a amino acid substitution such as single nucleotide polymorphism (SNP) or the like (with the proviso that it shows the LTRPC2 protein activity), but also a naturally existing variation functionally equivalent derived from a living thing other than human, rat and mouse [e.g., a mammal other than human and rat (e.g., hamster or dog)]. Also included are polypeptides and the like which are artificially modified by genetic engineering techniques based on these natural polypeptides, particularly the amino acid sequence represented by SEQ ID NO:4 or 14.

The polynucleotides coding for the novel polypeptides of the present invention are by themselves novel ones and therefore are included in the polynucleotide of the present invention. The polynucleotide of the present invention is preferably a polynucleotide coding for a polypeptide consisting of the amino acid sequence represented by SEQ ID NO:4 or SEQ ID NO:14, more preferably a polynucleotide comprising a sequence comprising bases of from the 84th position to the 4,610th position in the nucleotide sequence represented by SEQ ID NO:3 or comprising a sequence comprising bases of from the 36th position to the 4,559th position in the nucleotide sequence represented by SEQ ID NO:13. Further preferred is a sequence comprising bases of from the 84th position to the 4,610th position in the nucleotide sequence represented by SEQ ID NO:3. In this connection, both of DNA and RNA are included in the term "polynucleotide" as used herein.

The polypeptide or polynucleotide of the present invention can be used as a tool for screening a substance for a cell death inhibition.

[2] Cell for Screening Use and Expression Vector and Cell of the Present Invention The polypeptide consisting of the amino acid sequence represented by SEQ ID NO:2 is a known human natural type LTRPC2 protein. The polypeptides comprising the amino acid sequences represented by SEQ ID NO:2, SEQ ID NO:4 and SEQ ID NO:14 and variation functionally equivalents thereof are generally referred to as "LTRPC2 protein".

As the variation functionally equivalent of the "polypeptide consisting of the amino acid sequence represented by SEQ ID NO:2", for example, (1) a polypeptide which comprises the amino acid sequence represented by SEQ ID NO:2 and also shows the LTRPC2 protein activity;

(2) a polypeptide which comprises an amino acid sequence in which one or two or more, preferably from 1 to 5, more preferably from 1 to 3, further preferably one, of amino acids in the amino acid sequence represented by SEQ ID NO:2 are substituted, deleted and/or inserted and also shows the LTRPC2 protein activity;

(3) a partial fragment of a polypeptide which consists of the amino acid sequence represented by SEQ ID NO:2 and is also a partial fragment showing the LTRPC2 protein activity; or (4) a polypeptide which comprises an amino acid sequence having a homology of 84% or more (preferably 90% or more, more preferably 95% or more, further preferably 98% or more, and particularly preferably 99% or more) with the amino acid sequence represented by SEQ ID NO:2 and also shows the LTRPC2 protein activity, or the like can be exemplified. Similar to the case of the variation functionally equivalent of the polypeptide consisting of the amino acid sequence represented by SEQ ID NO:4 or SEQ ID NO:14, its origin is not limited, and a polypeptide artificially modified by genetic engineering techniques is also included therein.

The cell to be used in the screening method of the present invention (to be called cell for screening) is not particularly limited, with the proviso that it is a cell expressing the aforementioned LTRPC2 protein, and any one of the cells produced by genetic engineering techniques and the naturally occurring cells can be used, but it is desirable to use a cell produced by genetic engineering techniques. Also, a cell expressing a polypeptide consisting of the amino acid sequence represented by SEQ ID NO:2 or a variation functionally equivalent thereof is desirable, and a cell expressing a polypeptide consisting of the amino acid sequence represented by SEQ ID NO:2, SEQ ID NO:4 or SEQ ID NO:14 is more desirable. The cell for screening can be used as a screening tool for a substance for cell death inhibition.

A vector containing the polynucleotide of the present invention and a cell containing this vector are respectively novel and included in the vector of the present invention and the cell of the present invention. The cell of the present invention is included in the aforementioned cell for screening use and can be used in the screening of the present invention.

[3] Method for Producing Cell for Screening Use

Though the method for producing cell for screening use is not particularly limited, it can be obtained, for example, by ligating a polynucleotide coding for the LTRPC2 protein into an appropriate vector DNA and transforming a host cell (preferably a eucaryote, particularly preferably CHO cell). Also, it is possible to effect expression of the polynucleotide in respective host cell by introducing an appropriate promoter and a sequence related to gene expression into such a vector.

The method for producing a polynucleotide coding for the LTRPC2 protein (includes the polynucleotide of the present invention), which can be used for the production of the cell for screening use, is not particularly limited, but (1) a method which uses PCR, (2) a method which uses a usual genetic engineering technique (namely, a method in which a transformant containing the cDNA of interest is selected from transformants transformed with a cDNA library), (3) a chemical synthesis method or the like can be exemplified. The following describes respective production methods one by one. In this connection, though the following descriptions are described with reference to the polynucleotide of the present invention, LTRPC2 protein-encoding polynucleotides other than the polynucleotide of the present invention can also be produced in the same manner.

By the method which uses PCR, the polynucleotide of the present invention can be produced for example by the following procedure.

That is, mRNA is extracted from a cell or tissue having the ability to produce the polypeptide of the present invention. Next, based on the nucleotide sequence of a polynucleotide coding for the polypeptide of the present invention, a set of two primers which can sandwich complete length mRNA corresponding to the polypeptide of the present invention or a set of two primers which can sandwich a partial mRNA region thereof are prepared. By carrying out the reverse transcriptase-polymerase chain reaction (RT-PCR), complete length cDNA coding for the polypeptide of the present invention or a part thereof can be obtained.

More illustratively, total RNA containing the mRNA coding for the polypeptide of the present invention is extracted by a known method from a cell or tissue having the ability to produce the polypeptide of the present invention. Examples of the extraction method include a guanidine thiocyanate hot phenol method, a guanidine thiocyanate-guanidine hydrochloride method, a guanidine thiocyanate cesium chloride method and the like, but it is desirable to use the guanidine thiocyanate cesium chloride method. The cell or tissue having the ability to produce the polypeptide of the present invention can be specified for example by the Northern blotting method which uses a polynucleotide coding for the polypeptide of the present invention or a part thereof or the Western blotting method which uses an antibody specific for the polypeptide of the present invention.

Subsequently, the thus extracted mRNA is purified. Purification of the mRNA can be carried out in accordance with a conventional method; for example, it can be purified by effecting adsorption of the mRNA to an oligo(dT) cellulose column and then eluting the same. As occasion demands, the mRNA can be further fractionated by a sucrose density gradient centrifugation or the like method. In addition, a commercially available already extracted and purified mRNA can also be used without carrying out extraction of the mRNA.

Next, a single-stranded cDNA is synthesized by carrying out a reverse transcriptase reaction of the thus purified mRNA in the presence, for example, of a random primer, an oligo(dT) primer and/or a custom-synthesized primer. This synthesis can be carried out by a conventional method. The cDNA of interest can be amplified by carrying out PCR using the thus obtained single-stranded cDNA and two primers sandwiching the complete length or a partial region of the polynucleotide of interest. The thus obtained DNA is fractionated by an agarose gel electrophoresis or the like. As occasion demands, a DNA fragment of interest can also be obtained by digesting the aforementioned DNA with restriction enzymes and the like and ligating the fragments. In addition, a DNA fragment of interest can also be obtained from a genomic DNA.

According to the method which uses a usual genetic engineering technique, the polynucleotide of the present invention can be produced, for example, by the procedure described in b) The second production method of 1) Method for producing protein genes in "Mode for Carrying Out the Invention" of WO 01/34785.

Regarding the method which uses a chemical synthesis, the polynucleotide of the present invention can be produced, for example, by the procedures described in c) The third production method and d) The fourth production method of 1) Method for producing protein genes in "Mode for Carrying Out the Invention" of the aforementioned patent document. More illustratively, it can also be obtained by ligating nucleotide fragments produced by a chemical synthesis method. In addition, each polynucleotide (oligonucleotide) can be synthesized using a DNA synthesizer (e.g., Oligo 1000M DNA Synthesizer (manufactured by Beckman), 394 DNA/RNA Synthesizer (manufactured by Applied Biosystems) or the like).

Sequence determination of the DNA samples obtained by the various methods so far described can be carried out, for example, by the Maxam-Gilbert chemical modification method (Maxam, A. M. and Gilbert, W., "Methods in Enzymology", 65, 499–559, 1980), the dideoxy nucleotide chain termination method (Messing, J. and Vieira, J., *Gene*, 19, 269–276, 1982).

A host cell (preferably a eucaryote) can be transformed by integrating the thus isolated polynucleotide of the present invention into an appropriate vector DNA. Also, it is possible to effect expression of the polynucleotide in respective host cell by introducing an appropriate promoter and a sequence related to gene expression into such a vector.

As the host cell and expression vector which can be used for the production of the cell for screening use, for example, known host cell and expression vector generally usable in the genetic engineering can be used.

For example, cells of a vertebrate, an insect, a yeast and the like are included in the host cell of a eucaryote, and examples of the vertebrate cells include a monkey cell COS cell (Gluzman, Y., *Cell*, 23, 175–182, 1981), CHO dhfr⁻ cell which is a dihydrofolate reductase-deficient strain of Chinese hamster ovary cell (CHO) (Urlaub, G. and Chasin, L. A., *Proc. Natl. Acad. Sci. USA*, 77, 4216–4220, 1980), a human fetal kidney derived HEK 293 cell and a 293-EBNA cell (manufactured by Invitrogen) prepared by introducing Epstein-Barr virus EBNA-1 gene into the aforementioned HEK 293 cell.

When CHO cell is used as the host cell, a transformed cell which stably produce the LTRPC2 protein can be obtained by co-transfecting a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989), pSV2-neo (Southern, P. J. and Berg, P., *J. Mol. Appl. Genet.*, 1, 327–341, 1982) or the lie, together with an expression vector containing a polynucleotide coding for the LTRPC2 protein, and by selecting a G418-resistant colony.

As the expression vector for vertebrate cells, a vector having a promoter generally positioned at the upstream of the polynucleotide to be expressed, an RNA splicing site, polyadenylation site, transcription termination sequence and the like can be used, which may further have a replication origin as occasion demands. Examples of the aforementioned expression vector include pSV2dhfr having SV40 early promoter (Subramani, S. et al., *Mol. Cell. Biol.*, 1, 854–864, 1981), pEF-BOS having a human elongation factor promoter (Mizushima, S. and Nagata, S., Nucleic Acids Res., 18, 5322, 1990), pCEP4 having a cytomegalovirus promoter (manufactured by Invitrogen), pcDNA3.1 (+) (manufactured by Invitrogen) and the like.

The aforementioned expression vector can be incorporated into cells for example by the DEAE-dextran method (Luthman, H. and Magnusson, G., *Nucleic Acids Res.*, 11, 1295–1308, 1983), the calcium phosphate-DNA coprecipitation method (Graham, F. L. and van der Ed, A. J., *Virology*, 52, 456–457, 1973), a method which uses a commercially available transfection reagent (e.g., FuGENE™6 Transfection Reagent; manufactured by Roche Diagnostics), the electroporation method (Neumann, E. et al., *EMBO J.*, 1, 841–845, 1982) or the like.

The cell containing a polynucleotide coding for the LTRPC2 protein can be cultured in accordance with a conventional method, and the LTRPC2 protein is produced on the cell surface by the aforementioned culturing. As the medium which can be used in the aforementioned culturing, various media conventionally used in response to the employed host cells can be optionally selected. For example, in the case of CHO cell, a medium prepared by adding a serum component such as fetal bovine serum (FBS) or the like, as occasion demands to, for example, Dulbecco's modified Eagle's minimum essential medium or the like medium can be used. Also, in the case of the 293 cell, a medium prepared by adding G418 to Dulbecco's modified Eagle's minimum essential medium or the like medium supplemented with a serum component such as a fetal bovine serum (FBS) or the like can be used.

[4] Method for Screening a Substance Useful for Cell Death Inhibition

The method of the present invention for screening a substance useful for cell death inhibition includes (1) a step of allowing a substance to be tested to contact with a cell expressing the LTRPC2 protein under such a condition that the LTRPC2 protein can be activated and (2) a step of analyzing inhibition of the activation of the LTRPC2 protein.

According to the screening method of the present invention, a substance to be tested is allowed to contact with the cell for screening use under such a condition that the LTRPC2 protein can be activated. As the condition under which the LTRPC2 protein can be activated, in the presence of a LTRPC2 protein activator can for example be cited. As the aforementioned LTRPC2 protein activator, ADP ribose or NAD or a PARP activator (e.g., MNNG or $H_2O_2$) can for example be cited.

According to the screening method of the present invention, though not particularly limited, for example, the cell can be contacted with a substance to be tested after activation of the LTRPC2 protein or the cell can be contacted with a substance to be tested simultaneously with the activation of the LTRPC2 protein. In the former case, activation of the LTRPC2 protein is inhibited when the substance to be tested is a substance which inhibits activation of the LTRPC2 protein, and on the contrary, activation of the LTRPC2 protein is maintained when the substance to be tested is not a substance which inhibits activation of the LTRPC2 protein. In the latter case, on the other hand, activation of the LTRPC2 protein does not occur or is attenuated when the substance to be tested is a substance which inhibits activation of the LTRPC2 protein. On the contrary, activation of the LTRPC2 protein occurs when the substance to be tested is not a substance which inhibits activation of the LTRPC2 protein.

When the screening method of the present invention is used, a substance which inhibits activation of the LTRPC2 protein (namely an antagonist) can be screened. As has been found for the first time by the inventors, activation of the LTRPC2 protein is controlled by the activation of PARP. In addition, it is well known that cell death is induced by the activation of PARP. Accordingly, it has been revealed for the first time by the inventors that activation of the LTRPC2 protein is induced by the activation of PARP, and cell death is further induced as the result. Thus, a substance which inhibits activation of the LTRPC2 protein can inhibit a cell death induced by the activation of PARP and therefore is useful as the active ingredient of a therapeutic and/or preventive agent for a disease in which the cell death induced by the activation of PARP is concerned.

More illustratively, based on the difference in the method for analyzing activation of the LTRPC2 protein, for example, (a) a screening method which uses a patch-clamp method, (b) a screening method which uses influx or efflux of a radioisotope ion, (c) a screening method which uses efflux of $Rb^+$ ion, or (d) a screening method which uses an intracellular $Ca^+$ indicator may be exemplified as the screening method of the present invention.

When a substance which inhibits activation of the LTRPC2 protein and is useful as a cell death inhibitor is screened making use of the aforementioned patch-clamp method of (a), whether or not the activation of LTRPC2 protein is inhibited can be analyzed by measuring whole cell current in the cell for screening use using, for example, a whole-cell patch-clamp method (Hille, B., "Ionic Channels of Excitable Membranes", 2nd Ed., 1992, Sinauer Associates Inc., Mass.). That is, though not particularly limited, the screening method of the present invention which uses a patch-clamp method includes, for example, a step in which the cell for screening use membrane potential-clamped by the whole-cell patch-clamp method and said cell for screening use is allowed to contact with a substance to be tested under such a condition that the LTRPC2 protein can be activated and a step in which a change in the whole cell current in said cell for screening use is analyzed.

More illustratively, whole cell current in the cell for screening use is measured by membrane potential-clamped the cell for screening use by the whole-cell patch-clamp method and adding an LTRPC2 protein activating compound (e.g., ADP ribose, NAD, $H_2O_2$ or MNNG). In that case, a solution containing 145 mmol/L NaCl, 5 mmol/L KCl, 2 mmol/L $CaCl_2$, 2 mmol/L $MgCl_2$ and 10 mmol/L HEPES-Na (pH 7.4) is used as the extracellular solution, and a solution containing 150 mmol/L CsCl, 5 mmol/L $MgCl_2$ and 10 mmol/L HEPES-Cs (pH 7.2) can be used as the intracellular solution. By subsequently measuring changes in the current when a substance to be tested is added to the extracellular solution or intracellular solution, a substance which inhibits activation of the LTRPC2 protein can be screened. For example, in case that change in the whole cell current which is generated by the activation stimulus of the LTRPC2 protein disappears or is attenuated in the cell for screening use when a substance to be tested is added, it can be judged that said substance to be tested is a substance which inhibits activation of the LTRPC2 protein.

When a substance which inhibits activation of the LTRPC2 protein and is useful as a cell death inhibitor is screened making use of the aforementioned efflux of radioisotope ion of (b), its channel activity can be measured for example using respective radioisotope of $Ca^{2+}$, $Na^+$ or $K^+$ ion as the index (Sidney P. Colowick and Nathan O. Kaplan "Methods in Enzymology", 88 (1), 1982, Academic Press, 346–347). This analyzing method is based on a well known finding that the LTRPC2 protein causes permeation of $Ca^{2+}$, $Na^+$ or $K^+$ ion (Sano, Y. et al., *Science*, 293, 1327–1330, 2001).

Though not particularly limited, the screening method of the present invention which uses efflux of a radioisotope ion includes, for example, a step in which a radioisotope is incorporated into the cell for screening use and then said cell for screening use is allowed to contact with a substance to be tested under such a condition that the LTRPC2 protein can be activated and a step in which amount of the radioactivity discharged into the extracellular moiety of the cell for screening use, or amount of the radioactivity remained in the cell is analyzed.

More illustratively, it can be measured using $^{45}Ca^{2+}$, $^{22}Na^+$ or $^{42}K^+$ as the radioisotope of each ion. When $K^+$ is used, $K^+$ is incorporated into the cell in advance and then $K^+$ remained in the extracellular solution is removed. Thereafter, since the radioisotope $K^+$ is permeated when the LTRPC2 protein is activated using an LTRPC2 protein activator, the radioactivity in the extracellular solution (namely, the radioactivity discharged into the extracellular moiety) or the radioactivity remained in the cell can be used as the index of the channel activity. In case that $^{45}Ca^{2+}$ or $^{22}Na^+$ is used, the radioisotope permeates when the LTRPC2 protein is activated using an LTRPC2 protein activator under a condition of putting the $^{45}Ca^{2+}$ or $^{22}Na^+$ in the reaction solution, so that the radioactivity in the extracellular solution (namely, the radioactivity remained in the extracellular moiety) or the radioactivity influxed into the cell can be used as the index of the channel activity (Experimental Medicine Supplement "Cultured Cell Experimentation Methods for Molecular Biology Studies", edited by T. Kuroki, N. Kyo and K. Senda, 1995, published by Yodosha; to be referred to as reference 1 hereinafter). In that case, a substance which inhibits activation of the LTRPC2 protein can be screened by adding a substance to be tested in the presence of an LTRPC2 protein activator and measuring the radioactivity in the extracellular solution (namely, the radioactivity discharged into the extracellular moiety) or the radioactivity remained in the cell. More illustratively, it can be carried out in accordance with the "(c) screening method which uses efflux of $Rb^+$ ion" which is described below.

In general, an ion channel capable of effecting permeation of $K^+$ ion can also pass $Rb^+$ ion similar to the case of $K^+$ ion, so that the channel activity can be measured using efflux of a radioisotope $^{86}Rb^+$ as the index (Sidney P. Colowick and Nathan O. Kaplan "Methods in Enzymology", 88 (1), 1982, Academic Press, 346–347; to be referred to as reference 2 hereinafter).

Though not particularly limited, the screening method of the present invention in which a substance which inhibits activation of the LTRPC2 protein and is useful as a cell death inhibitor is screened making use of the aforementioned efflux of $Rb^+$ ion of (c) includes, for example, a step in which a radioisotope $^{86}Rb^+$ ion is incorporated into the cell for screening use and then said cell for screening use is allowed to contact with a substance to be tested under such a condition that the LTRPC2 protein can be activated and a step in which amount of the radioactivity of $^{86}Rb^+$ discharged into the extracellular moiety of the cell for screening use, or amount of the radioactivity of $^{86}Rb^+$ remained in the cell is analyzed.

According to the screening method of the present invention which uses efflux of $Rb^+$ ion, $^{86}Rb^+$ can be incorporated into the aforementioned cell by incubating the cell for screening use together with $^{86}RbCl$ (e.g., at 37° C. for 24 hours) (reference 1), The un-incorporated $^{86}Rb^+$ is removed by washing the cell with usual physiological saline. Since the amount of $^{86}Rb^+$ discharged into the extracellular moiety is increased when the LTRPC2 protein is activated, the radioactivity of $^{86}Rb^+$ in the extracellular solution or the radioactivity of $^{86}Rb^+$ remained in the cell can be used as the index of the channel activity.

More illustratively, for example, the cell for screening use incorporated in advance with $^{86}Rb^+$ is incubated (e.g., at 37° C. for 30 minutes) in a solution (e.g., physiological saline) containing a substance to be tested, in the presence of an LTRPC2 protein, and then the radioactivity of $^{86}Rb^+$ in the extracellular solution or the radioactivity of $^{86}Rb^+$ remained in the cell is measured. In that case, it is desirable to carry out the same operation as a negative control using a solution which does not contain the substance to be tested and in the absence of the LTRPC2 protein activator, and to carry out the same operation as a positive control using a solution which does not contain the substance to be tested and in the presence of the LTRPC2 protein activator. Since the LTRPC2 protein is not activated in the aforementioned negative control, $^{86}Rb^+$ is not discharged into the extracellular moiety, while $^{86}Rb^+$ is discharged into the extracellular moiety in the positive control because of the activation of LTRPC2 protein. When (1) discharge of $^{86}Rb^+$ into the extracellular moiety is nor observed similar to the case of the aforementioned negative control or (2) discharged amount of $^{86}Rb^+$ into the extracellular moiety is reduced in comparison with the aforementioned positive control, in case that a substance to be tested is added in the presence of an LTRPC2 protein activator, it can be judged that the aforementioned substance to be tested is a substance which inhibits activation of the LTRPC2 protein. It is desirable that the screening method of the present invention which uses discharge of $Rb^+$ ion is carried out under the conditions which are described later in Example 7.

When a substance which inhibits activation of the LTRPC2 protein and is useful as a cell death inhibitor is screened making use of the aforementioned intracellular $Ca^+$ indicator of (d), Fluo3-AM or the like can for example be used as the intracellular $Ca^+$ indicator. An intracellular $Ca^+$ indicator can optically detect changes in the intracellular $Ca^+$ concentration accompanied by the opening of the LTRPC2 protein (Experimental Medicine Supplement "Intracellular Calcium Experimentation Protocol", edited by S. Kudo, 1996, published by Yodosha). Activity of the LTRPC2 protein can be measured by the use of these indicators, and it is possible to screen a compound which inhibits activation of the LTRPC2 protein, by comparing changes in the amount at the time of the activation of LTRPC2 protein in the presence and absence of a substance to be tested. Though not particularly limited, the screening method of the present invention which uses an intracellular $Ca^+$ indicator includes, for example, a step in which an intracellular $Ca^+$ indicator is incorporated into the cell for screening use and then said cell for screening use is allowed to contact with a substance to be tested under such a condition that the LTRPC2 protein can be activated and a step in which changed amount of the intracellular $Ca^+$ indicator in the aforementioned cell for screening use is optically analyzed.

More illustratively, when the amount of $Ca^+$ permeating into the cell is reduced or disappears in comparison with the case of the absence of a substance to be tested, in case that the substance to be tested is added in the presence of an LTRPC2 protein activator, it can be judged that the aforementioned substance to be tested is a substance which inhibits activation of the LTRPC2 protein.

The substances to be tested as the objects to be selected by the screening method of the present invention are not particularly limited, but various conventionally known compounds (including peptides) registered in Chemical File, a group of compounds obtained by the combinatorial chemistry techniques (Terrett, N. K. et al., *Tetrahedron*, 51, 8135–8137, 1995), or a group of random peptides prepared by applying the phage display method (Felici, F. et al., *J. Mol. Biol.*, 222, 301–310, 1991) and the like can be used. Also, microorganisms, plants, marine organisms, animal-derived natural components (e.g., culture supernatants or tissue extracts) and the like can also be used as the substances to be tested by the screening. In addition, compounds (including peptides) prepared by chemically or biologically modifying the compounds (including peptides) selected by the screening method of the present invention can also be used.

[5] Method for Producing Pharmaceutical Composition for Cell Death Inhibition

A method for producing a pharmaceutical composition for cell death inhibition, characterized in that it comprises a step of carrying out a screening using the screening method of the present invention and a step of preparing a pharmaceutical preparation using a substance obtained by the aforementioned screening, is included in the present invention.

The pharmaceutical preparation which comprises a substance obtained by the screening method of the present invention as the active ingredient can be prepared by using carriers, fillers and/or other additive agents generally used in preparing medicaments, in response to the type of the aforementioned active ingredient.

Examples of the administration include oral administration by tablets, pills, capsules, granules, fine subtilaes, powders, solutions for oral use and the like and parenteral administration by injections (e.g., intravenous, intramuscular, intraarticular or the like), suppositories, percutaneous preparations, transmucosal preparations and the like. Particularly in the case of peptides which are digested in the stomach, parenteral administration such as intravenous injection or the like is desirable.

In the solid composition for oral administration, one or more active substances can be mixed with at least one inert diluent such as lactose, mannitol, glucose, microcrystalline cellulose, hydroxypropylcellulose, starch, polyvinyl pyrrolidone, aluminum magnesium silicate or the like. In the usual way, the aforementioned composition may contain other additives than the inert diluent, such as a lubricant, a disintegrating agent, a stabilizing agent, a solubilizing or solubilization assisting agent and the like. If necessary, tablets or pills may be coated with a sugar coating or a film of a gastric or enteric substance.

The liquid composition for oral administration can include, for example, emulsions, solutions, suspensions, syrups or elixirs and can contain a generally used inert diluent such as purified water or ethanol. In addition to the inert diluent, the aforementioned composition can also contain a moistening agent, a suspending agent a sweetener, an aromatic or an antiseptic.

The injections for parenteral administration can include aseptic aqueous or non-aqueous solutions, suspensions or emulsions. As a diluent, the water-soluble aqueous solutions or suspensions can include distilled water for injection, physiological saline or the like. Examples of the diluent for use in the non-aqueous solutions or suspensions include propylene glycol, polyethylene glycol, plant oil (e.g., olive oil), alcohols (e.g., ethanol), polysorbate 80 or the like. The aforementioned composition can further contain a moistening agent, an emulsifying agent, a dispersing agent, a stabilizing agent, a solubilizing or solubilization assisting agent, an antiseptic or the like. The aforementioned composition can be sterilized, for example, by filtration through a bacteria retaining filter, blending of a germicide or irradiation. Alternatively, it can be used by firstly making into a sterile solid composition and dissolving it in sterile water or a sterile solvent for injection prior to its use.

The dose can be optionally decided by taking into consideration strength of the activity of the active ingredient, namely a substance which inhibits activation of the LTRPC2 protein or a substance obtained by the screening method of the present invention, and symptoms, age, sex and the like of each patient to be treated.

For example, in the case of oral administration, the dose is usually from 0.1 to 100 mg, preferably from 0.1 to 50 mg, per day per adult (as 60 kg body weight). In the case of parenteral administration, it is from 0.01 to 50 mg, preferably from 0.01 to 10 mg, as a mode of injections.

EXAMPLES

The following illustratively describes the present invention based on examples, but they do not limit the scope of the present invention. In this connection, unless otherwise noted, genetic engineering techniques and channel activity analysis can be carried out in accordance with the conventionally known methods (Maniatis, T. et al., "Molecular Cloning—A Laboratory Manual", 1982, Cold Spring Harbor Laboratory, NY; Hille, B., "Ionic Channels of Excitable Membranes", 2nd Ed., 1992, Sinauer Associates Inc., MA).

In carrying out cloning in the examples, SUPERSCRIPT First-Strand Synthesis System for RT-PCR manufactured by Invitrogen was used as the kit for reverse transcription reaction, and TOPO XL PCR Cloning Kit manufactured by Invitrogen as the cloning kit.

Example 1

<Isolation of Gene Coding for Human LTRPC2 Protein and Construction of Expression Vector>

A complete length cDNA coding for a human LTRPC2 protein consisting of the amino acid sequence represented by SEQ ID NO:2 (to be referred simply to as "human LTRPC2 protein" in each of the following Examples) was obtained by the reverse transcription-polymerase chain reaction (RT-PCR) using a human leukocyte mRNA as the temperate. Firstly, a single-stranded cDNA was synthesized by carrying out reverse transcription of the human leukocyte mRNA (10 ng) using the kit for reverse transcription reaction. Using this single-stranded cDNA as the template, PCR was carried out by a hot start method using Taq DNA polymerase (LA Taq DNA polymerase; manufactured by Takara Shuzo). The aforementioned PCR was carried out using an oligonucleotide comprising the nucleotide sequence represented by SEQ ID NO:5 as the sense primer, and an oligonucleotide comprising the nucleotide sequence represented by SEQ ID NO:6 as the antisense primer, and firstly carrying out thermal denaturation at 98° C. (1 minute) and then repeating a cycle of 98° C. (15 seconds)/65° C. (30 seconds)/72° C. (6 minutes) 35 times. As a result, a DNA fragment of about 4.7 kbp was amplified.

This DNA fragment was cloned into pCR-TOPO vector using the cloning kit. LTRPC2-cDNA alone was isolated by digesting the thus obtained plasmid DNA with a restriction enzyme EcoRI and then cloned using a pcDNA3.1 (+) plasmid (manufactured by Invitrogen). Since the pcDNA3.1 (+) plasmid has a cytomegalovirus-derived promoter sequence, it can be used for expressing the LTRPC2 protein in animal cells. When nucleotide sequence of the thus obtained clone pcDNA3.1-LTRPC2 was analyzed by the dideoxy terminator method using a DNA sequencer (ABI 3700 DNA Sequencer; manufactured by Applied Biosystems), the sequence represented by SEQ ID NO:1 was obtained.

Example 2

<Expression Distribution of Human LTRPC2 Gene>

Expression distribution of human LTRPC2 gene in human tissues and human blood was analyzed by the RT-PCR method. Regarding the human tissues, 5 ng of each of mRNA preparations derive from respective human tissues (manufactured by Clontech) was subjected to a DNase treatment and then to reverse transcription using a kit for reverse transcription reaction (Advantage RT-for-PCR Kit; manufactured by Clontech), thereby obtaining a single-stranded cDNA. Using this single-stranded cDNA as the template, PCR was carried out by a hot start method using Taq DNA polymerase (LA Taq DNA polymerase; manufactured by Takara Shuzo).

A 100 ml portion of human blood was collected from an anonymous in-house volunteer (healthy person), using a syringe containing heparin sodium for preventing blood coagulation. The blood sample was fractionated into eosinophil, neutrophil, lymphocyte and platelet using Ficoll-Paque reagent (manufactured by Amersham Pharmacia), and then total RNA was extracted from each of them using ISOGEN reagent (manufactured by Nippon Gene). In this case, the actual operation was carried out in accordance with respective protocols attached to the Ficoll-Paque reagent and ISOGEN reagent. A single-stranded cDNA was obtained by subjecting 20 ng of each total RNA to a DNase treatment and then to reverse transcription using the kit for reverse transcription reaction. Using this single-stranded cDNA as the template, PCR was carried out by a hot start method using Taq DNA polymerase (LA Taq DNA polymerase; manufactured by Takara Shuzo).

The aforementioned PCR was carried out using an oligonucleotide comprising the nucleotide sequence represented by SEQ ID NO:7 as the sense primer, and an oligonucleotide comprising the nucleotide sequence represented by SEQ ID NO:8 as the antisense primer, and firstly carrying out thermal denaturation at 98° C. (1 minute) and then repeating a cycle of 98° C. (15 seconds)/70° C. (1 minute) 30 times. Each of these primers is a sequence specific for the human LTRPC2 gene, comprising a sequence comprising bases of from the 22nd to the 4,533rd positions in the nucleotide sequence represented by SEQ ID NO:1.

When RT-PCR analysis was carried out on respective human tissues (amygdala, caudate nucleus, hippocampus, corpus callosum, substantia nigra, thalamus, cerebellum, frontal lobe, hypothalamus, spinal cord, pituitary body, whole brain, heart, placenta, lung, trachea, liver, skeletal muscle, kidney, small intestine, stomach, spleen, bone marrow, thymus, thyroid gland, salivary gland, adrenal gland, mammary gland and prostate), a DNA fragment of about 660 bp was amplified in brain, spinal cord, heart, placenta, lung, trachea, small intestine, stomach, spleen, bone marrow, thymus and leukocyte. It was revealed based on this result that the mRNA of human LTRPC2 is expressed in tissues which have been reported to be related to diseases whose cause is a cell death accompanied by the PARP activation.

In addition, when the RT-PCR analysis was carried out on human blood, a DNA fragment of about 660 bp was amplified mainly in lymphocyte. It was revealed based on this result that the human LTRPC2 is expressed mainly in lymphocyte in the human blood. Since it has been revealed that lymphocyte carries an immune function, it was suggested that the LTRPC2 gene is taking an important role in an immune function.

Example 3

<Isolation of Gene Coding for Rat LTRPC2 Protein>

A complete length cDNA coding for a rat LTRPC2 protein consisting of the amino acid sequence represented by SEQ ID NO:4 (to be referred simply to as "rat LTRPC2 protein" in each of the following Examples) was obtained by RT-PCR using 10 ng of a rat brain mRNA (manufactured by Clontech) as the temperate, by the same techniques of Example 1. PCR was carried out using an oligonucleotide comprising the nucleotide sequence represented by SEQ ID NO:9 as the sense primer, and an oligonucleotide comprising the nucleotide sequence represented by SEQ ID NO:10 as the antisense primer, and firstly carrying out thermal denaturation at 98° C. (1 minute) and then repeating a cycle of 98° C. (15 seconds)/60° C. (30 seconds)/72° C. (5 minutes) 35 times. As a result, a DNA fragment of about 4.7 kbp was amplified. When this DNA fragment was cloned into pCR-TOPO vector and nucleotide sequence of the thus obtained clone pCR-TOPO-rat LTRPC2 was analyzed, the sequence represented by SEQ ID NO:3 was obtained. The nucleotide sequence represented by SEQ ID NO:3 has an open reading frame comprising 4,527 base pairs (a sequence comprising bases of from the 84th to 4,610th positions in the nucleotide sequence represented by SEQ ID NO:3). Amino acid sequence deduced from the aforementioned open reading frame was the amino acid sequence represented by SEQ ID NO:4 comprising 1,508 amino acid residues.

The amino acid sequence represented by SEQ ID NO:4 has a homology of 84% with the amino acid sequence represented by SEQ ID NO:2 (human LTRPC2 protein). In this connection, the aforementioned numerical value of homology is a value obtained by the aforementioned BLAST retrieval.

Example 4

<Expression Distribution of Rat LTRPC2 Gene>

Expression distribution of rat LTRPC2 gene in rat tissues was analyzed by the RT-PCR method. A 5 ng portion of each of mRNA preparations derive from respective rat tissues (manufactured by Clontech) was subjected to a DNase treatment and then to reverse transcription using the kit for reverse transcription reaction, thereby obtaining a single-stranded cDNA. Using this single-stranded cDNA as the template, PCR was carried out by a hot start method using a Taq DNA polymerase (Platinum Taq DNA polymerase; manufactured by Invitrogen). The aforementioned PCR was carried out using an oligonucleotide comprising the nucleotide sequence represented by SEQ ID NO:11 as the sense primer, and an oligonucleotide comprising the nucleotide sequence represented by SEQ ID NO:12 as the antisense primer, and firstly carrying out thermal denaturation at 95° C. (1 minute) and then repeating a cycle of 95° C. (15 seconds)/62° C. (30 seconds)/72° C. (1 minute) 35 times. Each of these primers is a sequence specific for the rat LTRPC2 gene, comprising a sequence comprising bases of from the 84th to 4,610th positions in the nucleotide sequence represented by SEQ ID NO:3.

When RT-PCR analysis was carried out on respective rat tissues (brain, heart, kidney, liver, lung, pancreas, retina, skeletal muscle, spleen and testis), a DNA fragment of about 380 bp was amplified in all of the tissues, thus revealing that the mRNA of rat LTRPC2 is expressed in each of the aforementioned tissues. In addition, it was revealed based on this result that the mRNA of rat LTRPC2 is expressed in tissues which have been reported to be related to diseases whose cause is a cell death accompanied by the PARP activation.

Example 5

<Expression of Human LTRPC2 Protein in Animal Cell>

In order to detect channel activity of the human LTRPC2 protein, expression of the aforementioned protein was induced in an animal cell. Using the expression vector pcDNA3.1-LTRPC2 obtained in Example 1 and a reagent for transfection (LIPOFECTAMINE 2000; manufactured by Invitrogen), transfection of a Chinese hamster ovary-derived CHO dhfr⁻ cell was carried out to induce expression of the human LTRPC2 protein. In this case, the aforementioned operation was carried out in accordance with the protocol attached to the aforementioned reagent for transfection and the known method (reference 1).

Example 6

<Detection of Activation of Human LTRPC2 Protein by PARP Activator>

This was carried out in accordance with the known methods (reference 1 and reference 2), except for the operation illustratively described in the following.

The transfected cells obtained in Example 5 ($1.6 \times 10^5$ cells) were incubated at 37° C. for 24 hours in the presence of $^{86}$RbCl (1 µCi/ml) to effect incorporation of $^{86}$Rb$^+$ into the cells and then washed with physiological saline to remove the $^{86}$Rb$^+$ which was not incorporated into the cells. The thus obtained cells were incubated at room temperature for 30 minutes in physiological saline supplemented with a PARP activator MNNG (final concentration=1 mmol/liter) or $H_2O_2$ (final concentration=0.06%). In this connection, the same operation was carried out as a control in general physiological saline (namely, physiological saline to which MNNG or $H_2O_2$ was not added).

The respective cells were washed with physiological saline, and then radioactivity of the $^{86}$Rb$^+$ remained in the cells was measured. As a result, residual activity of $^{86}$Rb$^+$ was reduced to 35.6% in the cells to which MNNG was added, and to 8.9% in the cells to which $H_2O_2$ was added, respectively, in comparison with the control cells. (cells to which MNNG or $H_2O_2$ was not added). This shows that $^{86}$Rb$^+$ in the cells was effluxed into the extracellular moiety caused by the activation of human LTRPC2 protein induced by MNNG or $H_2O_2$. It was revealed based on this result that the human LTRPC2 protein is activated by a PARP activator MNNG or $H_2O_2$.

Example 7

<Inhibition of Activation of Human LTRPC2 Protein by PARP Inhibitor>

This was carried out in accordance with the known methods (reference 1 and reference 2), except for the operation illustratively described in the following.

The transfected cells obtained in Example 5 ($1.6 \times 10^5$ cells) were incubated at 37° C. for 24 hours in the presence of $^{86}$RbCl (1 µCi/ml) to effect incorporation of $^{86}$Rb$^+$ into the cells and then washed with physiological saline to remove the $^{86}$Rb$^+$ which was not incorporated into the cells. The thus obtained cells were incubated at room temperature for 30 minutes in physiological saline supplemented with a PARP inhibitor DPQ (final concentration=100 µmol/liter), 3-aminobenzamide (final concentration=1 mmol/liter) or nicotinamide (final concentration=1 mmol/liter), in the presence of MNNG (final concentration=1 mmol/liter) or $H_2O_2$ (final concentration=0.06%). In this connection, the same operation was carried out as a control in physiological saline (namely, physiological saline to which DPQ, 3-aminobenzamide or nicotinamide was not added), in the absence of MNNG and $H_2O_2$.

The respective cells were washed with physiological saline, and then radioactivity of the $^{86}$Rb$^+$ remained in the cells was measured. As a result, residual activity of $^{86}$Rb$^+$ in respective cells to which the PARP inhibitor was added was similar to that of the control cells (cells to which MNNG or $H_2O_2$ was not added), namely the cells in which activity of the human LTRPC2 protein was not induced. More illustratively, the cells to which DPQ was added showed 93.4% (in the case of the presence of $H_2O_2$) or 95.5% (in the case of the presence of MNNG) of the $^{86}$Rb$^+$ residual activity. In the same manner, the cells to which 3-aminobenzamide was added showed 91.9% (in the case of the presence of $H_2O_2$) or 96.2% (in the case of the presence of MNNG) of the $^{86}$Rb$^+$ residual activity, and the cells to which nicotinamide was added showed 57.8% (in the case of the presence of $H_2O_2$) or 95.9% (in the case of the presence of MNNG) of the $^{86}$Rb$^+$ residual activity.

This shows that $^{86}$Rb$^+$ in the cells was not effluxed into the extracellular moiety, or the efflux was reduced, due to inhibition of the activation of human LTRPC2 protein caused by DPQ, 3-aminobenzamide or nicotinamide. It was revealed based on this result that the activation of human LTRPC2 protein by MNNG or $H_2O_2$ is inhibited by a PARP inhibitor DPQ, 3-aminobenzamide or nicotinamide.

Example 8

<Comparison of Human LTRPC2 Protein Inhibition and PARP Inhibition by PARP Inhibitor>

In order to verify that the human LTRPC2 protein inhibition by PARP inhibitor, shown in Example 7, occurs via PARP, $IC_{50}$ value of the human LTRPC2 protein inhibition and $IC_{50}$ value of the PARP inhibition were compared and examined.

$IC_{50}$ value of the LTRPC2 inhibition by each of the aforementioned PARP inhibitors DPQ, 3-aminobenzamide and nicotinamide was examined by the method of Example 7, by adding varied amounts of the inhibitors. As a result, $IC_{50}$ values of the human LTRPC2 protein inhibition by DPQ, 3-aminobenzamide and nicotinamide were 0.20 µM, 117 µM and 541 µM, respectively.

$IC_{50}$ value of the PARP inhibition was examined by the following method. The transfected cells obtained in Example 5 were incubated at room temperature for 30 minutes in physiological saline supplemented with a PARP activator MNNG (final concentration=1 mmol/liter) or $H_2O_2$ (final concentration=0.06%) and varied amount of the PARP inhibitor used in the above. In this connection, the same operation was carried out as a control in general physiological saline (namely, physiological saline to which MNNG or $H_2O_2$ was not added). Next, the cells after removal of the physiological saline supplemented with respective activator and inhibitor were incubated with 0.2 nCi/µl in final concentration of $^3$H-NAD at 37° C. for 40 minutes. Subsequently, the reaction was stopped by adding TCA to the cells to a final concentration of 10% and the cells were incubated at 4° C. for 30 minutes. Thereafter, the unincorporated $^3$H-NAD was removed by washing the cells twice with 5% TCA. The thus washed cells were lysed with a solution containing 2% SDS and 0.1 M NaOH, and then the $^3$H radioactivity contained in the cells was measured. As a result, $IC_{50}$ values of the PARP inhibition by DPQ, 3-aminobenzamide and nicotinamide were 0.26 µM, 71.7 µM and 335 µM, respectively.

Since the respective $IC_{50}$ values of LTRPC2 inhibition and PARP inhibition approximated to each other, it was confirmed that the LTRPC2 inhibition was due to the PARP inhibition.

Example 9

<Expression of Human LTRPC2 Protein in Animal Cell>

In order to clarify function of the human LTRPC2 protein in cells, expression of the aforementioned protein was induced in an animal cell. Using the expression vector pcDNA3.1-LTRPC2 obtained in Example 1 and a reagent for transfection (LIPOFECTAMINE 2000; manufactured by Invitrogen), transfection of a human fetal kidney-derived HEK 293 cell was carried out to induce expression of the human LTRPC2 protein. In this case, the aforementioned operation was carried out in accordance with the protocol attached to the aforementioned reagent for transfection and the known method (reference 1).

Example 10

<Induction of Cell Death by Human LTRPC2 Protein>

The transfected cells obtained in Example 8 were inoculated in $4 \times 10^4$ cells/well portions into a 96 well plate (manufactured by Asahi TechnoGlass), cultured overnight and then incubated at room temperature for 2 hours using a cell culture medium containing 0.001% in final concentration of $H_2O_2$. After washing with physiological saline, they were cultured for 4 hours by adding the cell culture medium. After removing the medium, alamaBlue Assay (provided by Bioscience) was carried out in order to judge life or death of the cells. According to this operation, life or death of the cells can be judged by adding a reagent which emits fluorescence by an oxidation reduction reaction in the cells and measuring the resulting fluorescence intensity. In this connection, the experimental procedure was carried out in accordance with the protocol attached to the reagent for the aforementioned alamaBlue Assay. The reagent for alamaBlue Assay was added to the stimulated cells, the mixture was incubated for additional 1 hour, and then the fluorescence intensity was measured. In this connection, the same operation was carried out as a control using cells transfected with pcDNA3.1 vector alone which does not contain LTRPC2. As a result, the fluorescence intensity was significantly reduced (reduction by 47.5%) in the cells in which LTRPC2 was expressed, in comparison with the cells in which the vector alone was expressed. This shows that a cell death occurred via LTRPC2 by the $H_2O_2$ stimulation, and surviving cells were reduced as a result. It was able to confirm based on this result that the human LTRPC2 protein accelerates the cell death by $H_2O_2$ stimulation. In addition, since it has been revealed by the aforementioned result that LTRPC2 is activated by the $H_2O_2$ stimulation, it is evident also from the result of this Example that the LTRPC2 protein has a function to induce cell death.

Example 11

<Isolation of Gene Coding for Mouse LTRPC2 Protein>

A complete length cDNA coding for a mouse LTRPC2 protein consisting of the amino acid sequence represented by SEQ ID NO:14 (to be referred simply to as "mouse LTRPC2 protein" in each of the following examples) was obtained by RT-PCR using 10 ng of a mouse brain mRNA (manufactured by Clontech) as the temperate, by the same techniques of Example 1 and Example 2. The PCR was carried out using an oligonucleotide comprising the nucleotide sequence represented by SEQ ID NO:15 as the sense primer, and an oligonucleotide comprising the nucleotide sequence represented by SEQ ID NO:16 as the antisense primer, and the PCR cycle was carried out under the same condition of Example 2. As a result, a DNA fragment of about 4.7 kbp was amplified. When this DNA fragment was cloned into the pCR-TOPO vector and nucleotide sequence of the thus obtained clone pCR-TOPO-mouse LTRPC2 was analyzed, the sequence represented by SEQ ID NO:13 was obtained. The nucleotide sequence represented by SEQ ID NO:13 has an open reading frame comprising 4,524 base pairs (a sequence comprising bases of from the 36th to 4,559th positions in the nucleotide sequence represented by SEQ ID NO:13). Amino acid sequence deduced from the aforementioned open reading frame was the amino acid sequence represented by SEQ ID NO:14 comprising 1,507 amino acid residues. The amino acid sequence represented by SEQ ID NO:14 has a homology of 84% with the amino acid sequence represented by SEQ ID NO:2 (human LTRPC2 protein) and that of 94% with the amino acid sequence represented by SEQ ID NO:4 (rat LTRPC2 protein). In this connection, the aforementioned numerical values of homology are values obtained by the aforementioned BLAST program.

Example 12

<Expression Analysis of Mouse LTRPC2 Gene in Rheumatoid Arthritis Model Animal>

In order to carry out expression analysis of LTRPC2 gene in rheumatoid arthritis, a mouse collagen-induced arthritis model was prepared as a model of rheumatoid arthritis, and changes in the expression of mouse LTRPC2 gene in this mouse were analyzed.

Preparation of the mouse collagen-induced arthritis model was carried out by the following method. A 150 µg portion of type 2 collagen was injected into a mouse joint region, the animal was fed for 3 weeks, and then injection of the same amount of collagen was carried out.

Subsequently, 5 weeks of feeding was carried out and then the joint region was excised by carrying out dissection. In this case, it was confirmed that damages (chondroclasis and osteoclasis) similar to the case of rheumatoid arthritis patients were formed in the excised mouse joint. This mouse joint was frozen and pulverized, and then mRNA was extracted using ISOGEN reagent (manufactured by Nippon Gene). In this connection, mRNA was also extracted as a control from a joint of a normal mouse without the treatment.

In order to analyze changes in the expression of mouse LTRPC2 gene in the thus obtained joint of mouse collagen-induced arthritis model, real time PCR was carried out using PRISM 7900 (manufactured by Applied Biosystems). By carrying out real time PCR, mouse LTRPC2 gene contained in mRNA can be quantified and measured.

The thus obtained mRNA was subjected to a DNase treatment and then to reverse transcription using the kit for reverse transcription reaction, thereby obtaining a single-stranded cDNA. Using this single-stranded cDNA as the template, PCR was carried out using a fluorescence reagent SYBR Green PCR Core Reagents Kit (manufactured by Applied Biosystems). The aforementioned PCR was carried out using an oligonucleotide comprising the nucleotide sequence represented by SEQ ID NO:17 as the sense primer, and an oligonucleotide comprising the nucleotide sequence represented by SEQ ID NO:18 as the antisense primer, and firstly carrying out thermal denaturation at 95° C. (10 minutes) and then repeating a cycle of 95° C. (15 seconds)/ 59° C. (1 minute) 45 times. These primers are sequences specific for the mouse LTRPC2 gene, comprising respective sequences of from the 3,763rd to 3,780th positions and from the 3,813rd to 3,830th positions in the nucleotide sequence represented by SEQ ID NO:13.

As a result, expressed amount of the mouse LTRPC2 gene was increased in the mouse collagen-induced arthritis model by a factor of about 15 times in comparison with the untreated normal mouse. It was revealed from this result that the mouse LTRPC2 gene is taking an important role in rheumatoid arthritis.

Example 13

<Expression Distribution of Mouse LTRPC2 Gene>

Expression distribution of mouse LTRPC2 gene in mouse tissues was analyzed by real time PCR by the same method of Example 12 using PRISM 7900 (manufactured by Applied Biosystems). A 5 ng portion of each of mRNA preparations (manufactured by Clontech) derive from respective mouse tissues (brain, heart, kidney, liver, lung, pancreas, skeletal muscle, smooth muscle, spleen and testis) was subjected to a DNase treatment and then to reverse transcription using the kit for reverse transcription reaction, thereby obtaining a single-stranded cDNA. Using this single-stranded cDNA as the template, PCR was carried out. As a result, amplification was detected in all of the tissues with the brain and spleen as the center. It was revealed from this that the mRNA of mouse LTRPC2 is expressed in each of the aforementioned tissues. In addition, it was revealed based on this result that the mRNA of mouse LTRPC2 is expressed in tissues which have been reported to be related to diseases whose cause is a cell death accompanied by the PARP activation.

Example 14

<Isolation of Gene Coding for PARP-1 Dominant Negative Mutant and Construction of Expression Vector>

A sequence of from the 1st to 374th positions of a human PARP-1 complete length amino acid sequence (Genebank accession No: XP-037273) is a DNA binding region, and it is known that when this DNA binding region alone is co-expressed wild type PARP-1, they compete for the binding to DNA. It is known that the binding ratio of wild type PARP-1 to DNA is reduced as the result, thus causing inhibition of the poly(ADP-ribosyl)ation of activated PARP-1 to DNA and inhibition of the induction of cell death (dominant negative effect). Thus, it has been revealed that the DNA binding region alone of PARP-1 functions as a dominant negative mutant protein which shows the dominant negative effect for PARP-1 (Kupper, J. H., de, Murcia, G. and Burkle, A., *J. Biol. Chem.*, 265, 18721–18724, 1990).

A complete length cDNA coding for a human PARP-1 dominant negative mutant protein comprising the aforementioned region, namely the amino acid sequence represented by SEQ ID NO:20 (to be referred simply to as "PARP-1 dominant negative mutant" in each of the following examples) was obtained by RT-PCR using a human spleen mRNA as the temperate. Firstly, a single-stranded cDNA was synthesized by carrying out reverse transcription of the human spleen mRNA (10 ng) using the kit for reverse transcription reaction. Using this single-stranded cDNA as the template, PCR was carried out by a hot start method using a Taq DNA polymerase (LA Taq DNA polymerase; manufactured by Takara Shuzo). The aforementioned PCR was carried out using an oligonucleotide comprising the nucleotide sequence represented by SEQ ID NO:21 as the sense primer, and an oligonucleotide comprising the nucleotide sequence represented by SEQ ID NO:22 as the antisense primer, and firstly carrying out thermal denaturation at 98° C. (1 minute) and then repeating a cycle of 98° C. (15 seconds)/65° C. (30 seconds)/72° C. (6 minutes) 35 times. As a result, a DNA fragment of about 1.2 kbp was amplified. This DNA fragment was cloned into the pCR-TOPO vector using the cloning kit. An insert (cDNA coding for the PARP-1 dominant negative mutant) alone was isolated by digesting the thus obtained plasmid DNA with a restriction enzyme EcoRI and then cloned using a pcDNA3.1(+) plasmid (manufactured by Invitrogen). When nucleotide sequence of the thus obtained clone pcDNA3.1-PARPt was analyzed by the dideoxy terminator method using a DNA sequencer (ABI 3700 DNA Sequencer; manufactured by Applied Biosystems), the sequence represented by SEQ ID NO:19 was obtained. The sequence represented by SEQ ID NO:19 encoded the PARP-1 dominant negative mutant.

Example 15

<Inhibition of Activation of Human LTRPC2 Protein by PARP-1 Dominant Negative Mutant>

In order to examine influence of the PARP-1 dominant negative mutant upon the channel activity of human LTRPC2 protein, expression of the aforementioned protein was induced in an animal cell. Using the expression vectors pcDNA3.1-LTRPC2 and pcDNA3.1-PARPt obtained in Example 1 and Example 14 and a reagent for transfection (LIPOFECTAMINE 2000; manufactured by Invitrogen), transfection of a Chinese hamster ovary-derived CHO dhfr⁻ cell was carried out to induce expression of the human LTRPC2 protein and PARP-1 dominant negative mutant. In this case, the aforementioned operation was carried out in accordance with the protocol attached to the aforementioned reagent for transfection and the known method (reference 1).

Activation of LTRPC2 in the thus obtained transformed cells ($1.6 \times 10^5$ cells) was measured using a method measuring efflux of $Rb^+$ ion. The method was carried out in the same manner as in Example 6. In this case, however, $H_2O_2$ (final concentration=0.06%) was used as the PARP activator, and cells in which the LTRPC2 protein alone obtained in Example 5 was expressed were used as the control.

As a result of the measurement, the residual activity of $^{86}Rb^+$ in the cells in which the PARP-1 dominant negative mutant was expressed was significantly increased in comparison with the control cells (cells in which the PARP-1 dominant negative mutant was not expressed).

This shows that the PARP activity was inhibited by the PARP-1 dominant negative mutant, and as the result, activation of the human LTRPC2 protein was inhibited and discharge of the intracellular $^{86}Rb^+$ into the extracellular moiety was reduced.

In addition, activation of PARP in this case was examined using the method of Example 8. However, $H_2O_2$ (final concentration=0.06%) was used as the PARP activator, and cells in which the LTRPC2 protein alone obtained in Example 5 was expressed were used as the control. As a result of the measurement, the $^3H$ radioactivity in the cells in which the PARP-1 dominant negative mutant was expressed was reduced to 67% in comparison with the control cells.

It was revealed based on these results that the activation of human LTRPC2 protein by $H_2O_2$ is inhibited by the PARP-1 dominant negative mutant. In addition to the results obtained by using PARP inhibitors (Example 7), it was confirmed also from the results obtained using the PARP-1 dominant negative mutant (this Example) that the LTRPC2 activation is inhibited by the reduction of PARP activity, and the activity of LTRPC2 therefore is controlled by PARP.

Example 16

<Screening of Human LTRPC2 Protein Inhibitor>

Screening was carried out on a compound capable of inhibiting the ion channel activity of human LTRPC2 protein.

The transfected cells obtained in Example 5 ($1.6 \times 10^5$ cells) were incubated at 37° C. for 24 hours in the presence of $^{86}RbCl$ (1 µCi/ml) to effect incorporation of $^{86}Rb^+$ into the cells and then washed with physiological saline to remove the $^{86}Rb^+$ which was not incorporated into the cells. The thus obtained cells were incubated at room temperature for 30 minutes in physiological saline supplemented with each of various compounds (final concentration=10 µmol/liter) in the presence of $H_2O_2$ (final concentration=0.06%). In this connection, the same operation was carried out as a control without adding the compound in the presence of $H_2O_2$.

The respective cells were washed with physiological saline, and then radioactivity of the $^{86}Rb^+$ remained in the cells was measured. A compound showing a significantly high residual activity as the thus obtained radioactivity, in comparison with the radioactivity of the control cells (cells to which $H_2O_2$ alone was added), is a compound which inhibits the channel activity of human LTRPC2 protein. This shows that $^{86}Rb^+$ in the cells was not effluxed into the extracellular moiety caused by the inhibition of the activation of human LTRPC2 protein induced by the added compound, or the efflux was reduced.

Since the compounds found in the above are obtained using, as the index, efflux of $^{86}Rb^+$ into the extracellular moiety accompanied by the activation of human LTRPC2 protein, the human LTRPC2 protein inhibition activity is not directly detected. More illustratively, a compound showing inhibition activity of PARP contained inside the cells also inhibits activation of the human LTRPC2 protein and inhibits efflux of $^{86}Rb^+$ into the extracellular moiety as a result. Accordingly, examination was further carried out on the PARP inhibition activity of the compounds obtained in the aforementioned process.

The transfected cells obtained in Example 5 were incubated at room temperature for 30 minutes in physiological saline supplemented with each of various compounds (final concentration=10 µmol/liter) in the presence of $H_2O_2$ (final concentration=0.06%). In this connection, the same operation was carried out as a control in the presence of $H_2O_2$ without adding the compound. Next, the cells after removal of the reaction solution were mixed with 0.2 nCi/µl in final concentration of $^3H$-NAD and incubated at 37° C. for 40 minutes. Subsequently, the reaction was stopped by adding TCA to the cells to a final concentration of 10% and incubating the mixture at 4° C. for 30 minutes. Thereafter, the un-incorporated $^3H$-NAD was removed by washing the cells twice with 5% TCA. The thus washed cells were lysed with a solution containing 2% SDS and 0.1% NaOH, and then the $^3H$ radioactivity contained in the cells was measured.

As a result, a compound showing a residual activity similar to the residual radioactivity of the control cells (cells to which $H_2O_2$ alone was added) was selected. This shows that the added compound is not inhibiting the PARP activity.

As a result of these examinations, a compound which inhibited efflux of $^{86}Rb^+$ into the extracellular moiety accompanied by the activation of human LTRPC2 protein but did not inhibit the intracellular PARP activity at the same time was selected. It is considered that this compound is directly inhibiting the activation of human LTRPC2 protein.

Next, in order to verify that the thus found compound is directly inhibiting the human LTRPC2 protein, its influence upon the ion channel activity of human LTRPC2 protein was examined using a technique of electrophysiology. Illustratively, the whole cell current which is generated when ADP ribose (500 µM in final concentration) is administered inside the cells was measured by membrane potential-clamped the transfected cells obtained in the aforementioned Example 5 by the whole cell membrane potential-clamped (whole-cell voltage-clamp) method. A solution containing 145 mmol/L NaCl, 5 mmol/L KCl, 2 mmol/L $CaCl_2$, 2 mmol/L $MgCl_2$ and 10 mmol/L HEPES-Na (pH 7.4) was used as the extracellular solution, and a solution containing 150 mmol/L CsCl, 5 mmol/L MgCl₂ and 10 mmol/L HEPES-Cs (pH 7.2) was used as the intracellular solution.

In this case, change in the whole cell current induced by ADP ribose was measured by adding the compound found by the aforementioned process simultaneously with the ADP ribose administration or at the time of the pretreatment. In that case, a compound which reduces change in the whole cell current in comparison with the case of the addition of ADP ribose alone, or completely inhibits induction thereof, is selected. This shows that the added compound directly inhibited the channel activity of human LTRPC2 protein.

By carrying out these examinations, it is possible to find out a compound capable of directly inhibiting the human LTRPC2 protein.

Example 17

<Expression of Human LTRPC2 Protein in Pancreatic Cell and Acceleration of Cell Death of Type I Diabetes Mellitus by Human LTRPC2 Protein>

Function of human LTRPC2 protein in pancreas and participation of human LTRPC2 protein in cell death in a type I diabetes mellitus model were examined. Regarding the cell death of pancreatic cell in type I diabetes mellitus, a cell death by streptozotocin stimulation can be used as its model. In addition, it has been revealed also that PARP is concerned in the process of this cell death (Pieper, A. A. et al., Proc. Natl. Acad. Sci., 96, 3059–3064, 1999).

Using the expression vector pcDNA3.1-LTRPC2 obtained in Example 1 and a reagent for transfection (LIPO-FECTAMINE; manufactured by Invitrogen), transfection of MIN6B cell derived from the β cell of the pancreatic islets of Langerhans was carried out to induce expression of the human LTRPC2 protein. In this case, the aforementioned operation was carried out in accordance with the protocol attached to the aforementioned reagent for transfection and the known method (reference 1).

The thus obtained transfected cells were inoculated in 4×10⁴ cells/well portions into a 96 well plate (manufactured by Asahi TechnoGlass), cultured overnight and then incubated at room temperature overnight using a cell culture medium containing 1 mM in final concentration of streptozotocin (manufactured by Sigma Aldrich). After removing the cell culture medium, an MTT Assay was carried out in order to judge life or death of the cells. According to this operation, life or death of the cells can be judged by making use of the reaction of developing blue color through the reduction of MTT into formazan by the respiratory enzyme system in mitochondria in the cells. After 2 hours of culturing by adding an MTT reagent (manufactured by Wako Pure Chemical Industries) to the stimulated cells, formazan was dissolved by adding DMSO to the resulting cells after removing the culture supernatant, and then its absorbance was measured using a spectrophotometer. In this case, the same operation was carried out as a control using cells transfected with the pcDNA3.1 vector alone which does not contain LTRPC2. As a result, the absorbance was significantly reduced (reduced to 93%) in the cells in which LTRPC2 was expressed, in comparison with the cells in which the vector alone was expressed. This shows that cell death was induced via LTRPC2 by the streptozotocin stimulation, and the number of surviving cells was reduced as the result. Based on this result, it was able to confirm that the human LTRPC2 protein accelerates cell death by streptozotocin stimulation. In addition, since the cell death by streptozotocin stimulation is a model of type I diabetes mellitus, it was revealed that the human LTRPC2 has a function to induce cell death by type I diabetes mellitus.

INDUSTRIAL APPLICABILITY

According to the screening method of the present invention, it can screen a substance capable of inhibiting cell death induced by the activation of PARP, particularly a substance which is useful as a therapeutic agent and/or a preventive agent for a disease in which cell death induced by the activation of PARP is concerned (e.g., rheumatoid arthritis, neuronal death at the time of cerebral ischemia, cell death of the heart after myocardial infarction reperfusion, autoimmune destruction of β-cells of pancreatic islets of Langerhans, cell death after shock, or inflammatory reaction by immunocyte death). The screening system of the present invention can be constructed using the LTRPC2 of the present invention and the cell of the present invention.

Though the present invention has been described in the foregoing by specified embodiments, modifications and improvements obvious to those skilled in the art are included in the scope of the invention.

The invention claimed is:

1. An isolated polypeptide selected from the group consisting of (a) a polypeptide which comprises the amino acid sequence represented by SEQ ID NO:4 or SEQ ID NO:14, and (b) a polypeptide which comprises the amino acid sequence of SEQ ID NO: 4 or SEQ ID NO:14 in which from one to five amino acids are substituted, deleted and/or inserted, and which has an activity to cause permeation of ions.

2. An isolated polypeptide which consists of the amino acid sequence represented by SEQ ID NO:4.

3. An isolated polynucleotide which encodes the polypeptide according to claim 1 or 2.

4. An isolated polypeptide which consists of the amino acid sequence represented by SEQ ID NO:14.

5. An isolated polynucleotide which encodes the polypeptide according to claim 4.

6. An expression vector which comprises the polynucleotide according to claim 3.

7. An expression vector which comprises the polynucleotide according to claim 5.

8. An isolated host cell which comprises the vector according to claim 6.

9. An isolated host cell which comprises the vector according to claim 7.

10. A process for producing the polypeptide according to claim 1 or 2 comprising, culturing an isolated host cell harboring an expression vector that comprises a polynucleotide encoding said polypeptide under conditions promoting expression of said polypeptide and recovering said polypeptide from the cell culture.

11. A process for producing the polypeptide according to claim 4 comprising, culturing an isolated host cell harboring an expression vector that comprises a polynucleotide encoding said polypeptide under conditions promoting expression of said polypeptide and recovering said polypeptide from the cell culture.

12. A method for determining whether a compound is an inhibitor of an ion channel, wherein said ion channel is comprised of a polypeptide selected from the group consisting of (a) a polypeptide represented by SEQ ID NO:2, (b) a polypeptide represented by SEQ ID NO:4, (c) a polypeptide with at least 84% sequence homology to the polypeptide represented by SEQ ID NO:2 wherein the polypeptide (c) has an activity to cause permeation of ions, and (d) a polypeptide with at least 84% sequence homology to the polypeptide represented by SEQ ID NO:4, wherein the polypeptide (d) has an activity to cause permeation of ions, said method comprising:

(A) contacting a cell expressing (i) PARP-1 and (ii) said polypeptide with (a) a test compound in the presence of an exogenous PARP-1 activator, wherein said PARP-1 activator activates, through PARP, an ion channel comprised of said polypeptide;

(B) measuring ion flow through said ion channel; and (C) comparing the ion flow through said ion channel of (B) with the ion flow through an ion channel in a corresponding cell cultured in the presence of said exogenous PARP-1 activator and in the absence of said test compound, wherein when the ion flow through said ion channel is lower in the presence of said test compound than in the absence of said test compound, said test compound is determined to be an inhibitor of an ion channel.

13. The method of claim 12, wherein said PARP-1 activator is $H_2O_2$ or MNNG.

14. The method of claim 12, wherein said cell is a eukaryotic cell.

15. The method of claim 12, wherein flow through said ion channel is measured using a patch-clamp technique, influx or efflux of a radioisotopic ion, efflux of $Rb^+$ ion, or an intracellular $Ca^{2+}$ indicator.

16. The method of claim 12, wherein the cell expresses a polypeptide having the amino acid sequence of SEQ ID NO:2, or SEQ ID NO:4.

17. A method for determining whether a test compound is an inhibitor of an ion channel, wherein said ion channel is comprised of a polypeptide represented by SEQ ID NO: 14, said method comprising:

(A) contacting a cell expressing (i) PARP-1 and (ii) said polypeptide with (a) a test compound in the presence of an exogenous PARP-1 activator, wherein said PARP-1 activator activates, through PARP, an ion channel comprised of said polypeptide;

(B) measuring ion flow through said ion channel; and (C) comparing the ion flow through said ion channel of (B) with the ion flow through an ion channel in a corresponding cell cultured in the presence of said exogenous PARP-1 activator and in the absence of said test compound, wherein when the ion flow through said ion channel is lower in the presence of said test compound than in the absence of said test compound, said test compound is determined to be an inhibitor of an ion channel.

* * * * *

SEQUENCE LISTING

<160> NUMBER OF SEQ ID NOS: 18

<210> SEQ ID NO 1
<211> LENGTH: 4738
<212> TYPE: DNA
<213> ORGANISM: Homo sapiens
<220> FEATURE:
<221> NAME/KEY: CDS
<222> LOCATION: (22)..(4533)

<400> SEQUENCE: 1

```
agctggcgtg ggggtctcag a atg gag ccc tca gcc ctg agg aaa gct ggc          51
                         Met Glu Pro Ser Ala Leu Arg Lys Ala Gly
                          1               5                  10 tcg gag cag gag gag ggc ttt gag ggg ctg ccc aga agg gtc act gac          99
Ser Glu Gln Glu Glu Gly Phe Glu Gly Leu Pro Arg Arg Val Thr Asp
         15                  20                  25
```

```
ctg ggg atg gtc tcc aat ctc cgg cgc agc aac agc agc ctc ttc aag      147
Leu Gly Met Val Ser Asn Leu Arg Arg Ser Asn Ser Ser Leu Phe Lys
             30                  35                  40 agc tgg agg cta cag tgc ccc ttc ggc aac aat gac aag caa gaa agc      195
Ser Trp Arg Leu Gln Cys Pro Phe Gly Asn Asn Asp Lys Gln Glu Ser
         45                  50                  55 ctc agt tcg tgg att cct gaa aac atc aag aag aaa gaa tgc gtg tat      243
Leu Ser Ser Trp Ile Pro Glu Asn Ile Lys Lys Lys Glu Cys Val Tyr
 60                  65                  70 ttt gtg gaa agt tcc aaa ctg tct gat gct ggg aag gtg gtg tgt cag      291
Phe Val Glu Ser Ser Lys Leu Ser Asp Ala Gly Lys Val Val Cys Gln
 75                  80                  85                  90 tgt ggc tac acg cat gag cag cac ttg gag gag gct acc aag ccc cac      339
Cys Gly Tyr Thr His Glu Gln His Leu Glu Glu Ala Thr Lys Pro His
                 95                 100                 105 acc ttc cag ggc aca cag tgg gac cca aag aaa cat gtc cag gag atg      387
Thr Phe Gln Gly Thr Gln Trp Asp Pro Lys Lys His Val Gln Glu Met
            110                 115                 120 cca acc gat gcc ttt ggc gac atc gtc ttc acg ggc ctg agc cag aag      435
Pro Thr Asp Ala Phe Gly Asp Ile Val Phe Thr Gly Leu Ser Gln Lys
        125                 130                 135 gtg aaa aag tac gtc cga gtc tcc cag gac acg ccc tcc agc gtg atc      483
Val Lys Lys Tyr Val Arg Val Ser Gln Asp Thr Pro Ser Ser Val Ile
140                 145                 150 tac cac ctc atg acc cag cac tgg ggg ctg gac gtc ccc aat ctc ttg      531
Tyr His Leu Met Thr Gln His Trp Gly Leu Asp Val Pro Asn Leu Leu
155                 160                 165                 170 atc tcg gtg acc ggg ggg gcc aag aac ttc aac atg aag ccg cgg ctg      579
Ile Ser Val Thr Gly Gly Ala Lys Asn Phe Asn Met Lys Pro Arg Leu
                175                 180                 185 aag agc att ttc cgc aga ggc ctg gtc aag gtg gct cag acc aca ggg      627
Lys Ser Ile Phe Arg Arg Gly Leu Val Lys Val Ala Gln Thr Thr Gly
            190                 195                 200 gcc tgg atc atc aca ggg ggg tcc cac acc ggc gtc atg aag cag gta      675
Ala Trp Ile Ile Thr Gly Gly Ser His Thr Gly Val Met Lys Gln Val
        205                 210                 215 ggc gag gcg gtg cgg gac ttc agc ctg agc agc agc tac aag gaa ggc      723
Gly Glu Ala Val Arg Asp Phe Ser Leu Ser Ser Ser Tyr Lys Glu Gly
220                 225                 230 gag ctc atc acc atc gga gtc gcc acc tgg ggc act gtc cac cgc cgc      771
Glu Leu Ile Thr Ile Gly Val Ala Thr Trp Gly Thr Val His Arg Arg
235                 240                 245                 250 gag ggc ctg atc cat ccc acg ggc agc ttc ccc gcc gag tac ata ctg      819
Glu Gly Leu Ile His Pro Thr Gly Ser Phe Pro Ala Glu Tyr Ile Leu
                255                 260                 265 gat gag gat ggc caa ggg aac ctg acc tgc cta gac agc aac cac tct      867
Asp Glu Asp Gly Gln Gly Asn Leu Thr Cys Leu Asp Ser Asn His Ser
            270                 275                 280 cac ttc atc ctc gtg gac gac ggg acc cac ggc cag tac ggg gtg gag      915
His Phe Ile Leu Val Asp Asp Gly Thr His Gly Gln Tyr Gly Val Glu
        285                 290                 295 att cct ctg agg acc agg ctg gag aag ttc ata tcg gag cag acc aag      963
Ile Pro Leu Arg Thr Arg Leu Glu Lys Phe Ile Ser Glu Gln Thr Lys
300                 305                 310 gaa aga gga ggt gtg gcc atc aag atc ccc atc gtg tgc gtg gtg ctg     1011
Glu Arg Gly Gly Val Ala Ile Lys Ile Pro Ile Val Cys Val Val Leu
315                 320                 325                 330 gag ggc ggc ccg ggc acg ttg cac acc atc gac aac gcc acc acc aac     1059
Glu Gly Gly Pro Gly Thr Leu His Thr Ile Asp Asn Ala Thr Thr Asn
```

|  |  |  |  |  |  |  |  |  |  |  |  |  |  |  |  |
|---|---|---|---|---|---|---|---|---|---|---|---|---|---|---|---|
|  |  |  | 335 |  |  |  | 340 |  |  |  | 345 |  |  |  |  |
| ggc | acc | ccc | tgt | gtg | gtt | gtg | gag | ggc | tcg | ggc | cgc | gtg | gcc | gac | gtc | 1107 |
| Gly | Thr | Pro | Cys | Val | Val | Val | Glu | Gly | Ser | Gly | Arg | Val | Ala | Asp | Val |  |
|  |  | 350 |  |  |  |  | 355 |  |  |  |  | 360 |  |  |  |  |
| att | gcc | cag | gtg | gcc | aac | ctg | cct | gtc | tcg | gac | atc | act | atc | tcc | ctg | 1155 |
| Ile | Ala | Gln | Val | Ala | Asn | Leu | Pro | Val | Ser | Asp | Ile | Thr | Ile | Ser | Leu |  |
|  |  | 365 |  |  |  |  | 370 |  |  |  |  | 375 |  |  |  |  |
| atc | cag | cag | aaa | ctg | agc | gtg | ttc | ttc | cag | gag | atg | ttt | gag | acc | ttc | 1203 |
| Ile | Gln | Gln | Lys | Leu | Ser | Val | Phe | Phe | Gln | Glu | Met | Phe | Glu | Thr | Phe |  |
|  | 380 |  |  |  |  | 385 |  |  |  |  | 390 |  |  |  |  |  |
| acg | gaa | agc | agg | att | gtc | gag | tgg | acc | aaa | aag | atc | caa | gat | att | gtc | 1251 |
| Thr | Glu | Ser | Arg | Ile | Val | Glu | Trp | Thr | Lys | Lys | Ile | Gln | Asp | Ile | Val |  |
| 395 |  |  |  |  | 400 |  |  |  |  | 405 |  |  |  |  | 410 |  |
| cgg | agg | cgg | cag | ctg | ctg | act | gtc | ttc | cgg | gaa | ggc | aag | gat | ggt | cag | 1299 |
| Arg | Arg | Arg | Gln | Leu | Leu | Thr | Val | Phe | Arg | Glu | Gly | Lys | Asp | Gly | Gln |  |
|  |  |  |  | 415 |  |  |  |  | 420 |  |  |  |  | 425 |  |  |
| cag | gac | gtg | gat | gtg | gcc | atc | ttg | cag | gcc | ttg | ctg | aaa | gcc | tca | cgg | 1347 |
| Gln | Asp | Val | Asp | Val | Ala | Ile | Leu | Gln | Ala | Leu | Leu | Lys | Ala | Ser | Arg |  |
|  |  |  | 430 |  |  |  |  | 435 |  |  |  |  | 440 |  |  |  |
| agc | caa | gac | cac | ttt | ggc | cac | gag | aac | tgg | gac | cac | cag | ctg | aaa | ctg | 1395 |
| Ser | Gln | Asp | His | Phe | Gly | His | Glu | Asn | Trp | Asp | His | Gln | Leu | Lys | Leu |  |
|  |  | 445 |  |  |  |  | 450 |  |  |  |  | 455 |  |  |  |  |
| gca | gtg | gca | tgg | aat | cgc | gtg | gac | att | gcc | cgc | agt | gag | atc | ttc | atg | 1443 |
| Ala | Val | Ala | Trp | Asn | Arg | Val | Asp | Ile | Ala | Arg | Ser | Glu | Ile | Phe | Met |  |
|  | 460 |  |  |  |  | 465 |  |  |  |  | 470 |  |  |  |  |  |
| gat | gag | tgg | cag | tgg | aag | cct | tca | gat | ctg | cac | ccc | acg | atg | aca | gct | 1491 |
| Asp | Glu | Trp | Gln | Trp | Lys | Pro | Ser | Asp | Leu | His | Pro | Thr | Met | Thr | Ala |  |
| 475 |  |  |  |  | 480 |  |  |  |  | 485 |  |  |  |  | 490 |  |
| gca | ctc | atc | tcc | aac | aag | cct | gag | ttt | gtg | aag | ctc | ttc | ctg | gaa | aac | 1539 |
| Ala | Leu | Ile | Ser | Asn | Lys | Pro | Glu | Phe | Val | Lys | Leu | Phe | Leu | Glu | Asn |  |
|  |  |  |  | 495 |  |  |  |  | 500 |  |  |  |  | 505 |  |  |
| ggg | gtg | cag | ctg | aag | gag | ttt | gtc | acc | tgg | gac | acc | ttg | ctc | tac | ctg | 1587 |
| Gly | Val | Gln | Leu | Lys | Glu | Phe | Val | Thr | Trp | Asp | Thr | Leu | Leu | Tyr | Leu |  |
|  |  |  | 510 |  |  |  |  | 515 |  |  |  |  | 520 |  |  |  |
| tac | gag | aac | ctg | gac | ccc | tcc | tgc | ctg | ttc | cac | agc | aag | ctg | caa | aag | 1635 |
| Tyr | Glu | Asn | Leu | Asp | Pro | Ser | Cys | Leu | Phe | His | Ser | Lys | Leu | Gln | Lys |  |
|  |  | 525 |  |  |  |  | 530 |  |  |  |  | 535 |  |  |  |  |
| gtg | ctg | gtg | gag | gat | ccc | gag | cgc | ccg | gct | tgc | gcg | ccc | gcg | gcg | ccc | 1683 |
| Val | Leu | Val | Glu | Asp | Pro | Glu | Arg | Pro | Ala | Cys | Ala | Pro | Ala | Ala | Pro |  |
|  | 540 |  |  |  |  | 545 |  |  |  |  | 550 |  |  |  |  |  |
| cgc | ctg | cag | atg | cac | cac | gtg | gcc | cag | gtg | ctg | cgg | gag | ctg | ctg | ggg | 1731 |
| Arg | Leu | Gln | Met | His | His | Val | Ala | Gln | Val | Leu | Arg | Glu | Leu | Leu | Gly |  |
| 555 |  |  |  |  | 560 |  |  |  |  | 565 |  |  |  |  | 570 |  |
| gac | ttc | acg | cag | ccg | ctt | tat | ccc | cgg | ccc | cgg | cac | aac | gac | cgg | ctg | 1779 |
| Asp | Phe | Thr | Gln | Pro | Leu | Tyr | Pro | Arg | Pro | Arg | His | Asn | Asp | Arg | Leu |  |
|  |  |  |  | 575 |  |  |  |  | 580 |  |  |  |  | 585 |  |  |
| cgg | ctc | ctg | ctg | ccc | gtt | ccc | cac | gtc | aag | ctc | aac | gtg | cag | gga | gtg | 1827 |
| Arg | Leu | Leu | Leu | Pro | Val | Pro | His | Val | Lys | Leu | Asn | Val | Gln | Gly | Val |  |
|  |  |  | 590 |  |  |  |  | 595 |  |  |  |  | 600 |  |  |  |
| agc | ctc | cgg | tcc | ctc | tac | aag | cgt | tcc | tca | ggc | cat | gtg | acc | ttc | acc | 1875 |
| Ser | Leu | Arg | Ser | Leu | Tyr | Lys | Arg | Ser | Ser | Gly | His | Val | Thr | Phe | Thr |  |
|  |  | 605 |  |  |  |  | 610 |  |  |  |  | 615 |  |  |  |  |
| atg | gac | ccc | atc | cgt | gac | ctt | ctc | att | tgg | gcc | att | gtc | cag | aac | cgt | 1923 |
| Met | Asp | Pro | Ile | Arg | Asp | Leu | Leu | Ile | Trp | Ala | Ile | Val | Gln | Asn | Arg |  |
|  | 620 |  |  |  |  | 625 |  |  |  |  | 630 |  |  |  |  |  |
| cgg | gag | ctg | gca | gga | atc | atc | tgg | gct | cag | agc | cag | gac | tgc | atc | gca | 1971 |
| Arg | Glu | Leu | Ala | Gly | Ile | Ile | Trp | Ala | Gln | Ser | Gln | Asp | Cys | Ile | Ala |  |
| 635 |  |  |  |  | 640 |  |  |  |  | 645 |  |  |  |  | 650 |  |
| gcg | gcc | ttg | gcc | tgc | agc | aag | atc | ctg | aag | gaa | ctg | tcc | aag | gag | gag | 2019 |

-continued

| | | |
|---|---|---|
| Ala Ala Leu Ala Cys Ser Lys Ile Leu Lys Glu Leu Ser Lys Glu Glu<br>655 660 665 | | |
| gag gac acg gac agc tcg gag gag atg ctg gcg ctg gcg gag gag tat<br>Glu Asp Thr Asp Ser Ser Glu Glu Met Leu Ala Leu Ala Glu Glu Tyr<br>670 675 680 | | 2067 |
| gag cac aga gcc atc ggg gtc ttc acc gag tgc tac cgg aag gac gaa<br>Glu His Arg Ala Ile Gly Val Phe Thr Glu Cys Tyr Arg Lys Asp Glu<br>685 690 695 | | 2115 |
| gag aga gcc cag aaa ctg ctc acc cgc gtg tcc gag gcc tgg ggg aag<br>Glu Arg Ala Gln Lys Leu Leu Thr Arg Val Ser Glu Ala Trp Gly Lys<br>700 705 710 | | 2163 |
| acc acc tgc ctg cag ctc gcc ctg gag gcc aag gac atg aag ttt gtg<br>Thr Thr Cys Leu Gln Leu Ala Leu Glu Ala Lys Asp Met Lys Phe Val<br>715 720 725 730 | | 2211 |
| tct cac ggg ggc atc cag gcc ttc ctg acc aag gtg tgg tgg ggc cag<br>Ser His Gly Gly Ile Gln Ala Phe Leu Thr Lys Val Trp Trp Gly Gln<br>735 740 745 | | 2259 |
| ctc tcc gtg gac aat ggg ctg tgg cgt gtg acc ctg tgc atg ctg gcc<br>Leu Ser Val Asp Asn Gly Leu Trp Arg Val Thr Leu Cys Met Leu Ala<br>750 755 760 | | 2307 |
| ttc ccg ctg ctc ctc acc ggc ctc atc tcc ttc agg gag aag agg ctg<br>Phe Pro Leu Leu Leu Thr Gly Leu Ile Ser Phe Arg Glu Lys Arg Leu<br>765 770 775 | | 2355 |
| cag gat gtg ggc acc ccc gcg gcc cgc gcc cgt gcc ttc ttc acc gca<br>Gln Asp Val Gly Thr Pro Ala Ala Arg Ala Arg Ala Phe Phe Thr Ala<br>780 785 790 | | 2403 |
| ccc gtg gtc gtc ttc cac ctg aac atc ctc tcc tac ttc gcc ttc ctc<br>Pro Val Val Val Phe His Leu Asn Ile Leu Ser Tyr Phe Ala Phe Leu<br>795 800 805 810 | | 2451 |
| tgc ctg ttc gcc tac gtg ctc atg gtg gac ttc cag cct gtg ccc tcc<br>Cys Leu Phe Ala Tyr Val Leu Met Val Asp Phe Gln Pro Val Pro Ser<br>815 820 825 | | 2499 |
| tgg tgc gag tgt gcc atc tac ctc tgg ctc ttc tcc ttg gtg tgc gag<br>Trp Cys Glu Cys Ala Ile Tyr Leu Trp Leu Phe Ser Leu Val Cys Glu<br>830 835 840 | | 2547 |
| gag atg cgg cag ctc ttc tat gac cct gac gag tgc ggg ctg atg aag<br>Glu Met Arg Gln Leu Phe Tyr Asp Pro Asp Glu Cys Gly Leu Met Lys<br>845 850 855 | | 2595 |
| aag gca gcc ttg tac ttc agt gac ttc tgg aat aag ctg gac gtc ggc<br>Lys Ala Ala Leu Tyr Phe Ser Asp Phe Trp Asn Lys Leu Asp Val Gly<br>860 865 870 | | 2643 |
| gca atc ttg ctc ttc gtg gca ggg ctg acc tgc agg ctc atc ccg gcg<br>Ala Ile Leu Leu Phe Val Ala Gly Leu Thr Cys Arg Leu Ile Pro Ala<br>875 880 885 890 | | 2691 |
| acg ctg tac ccc ggg cgc gtc atc ctc tct ctg gac ttc atc ctg ttc<br>Thr Leu Tyr Pro Gly Arg Val Ile Leu Ser Leu Asp Phe Ile Leu Phe<br>895 900 905 | | 2739 |
| tgc ctc cgg ctc atg cac att ttt acc atc agt aag acg ctg ggg ccc<br>Cys Leu Arg Leu Met His Ile Phe Thr Ile Ser Lys Thr Leu Gly Pro<br>910 915 920 | | 2787 |
| aag atc atc att gtg aag cgg atg atg aag gac gtc ttc ttc ttc ctc<br>Lys Ile Ile Ile Val Lys Arg Met Met Lys Asp Val Phe Phe Phe Leu<br>925 930 935 | | 2835 |
| ttc ctg ctg gct gtg tgg gtg gtg tcc ttc ggg gtg gcc aag cag gcc<br>Phe Leu Leu Ala Val Trp Val Val Ser Phe Gly Val Ala Lys Gln Ala<br>940 945 950 | | 2883 |
| atc ctc atc cac aac gag cgc cgg gtg gac tgg ctg ttc cga ggg gcc<br>Ile Leu Ile His Asn Glu Arg Arg Val Asp Trp Leu Phe Arg Gly Ala<br>955 960 965 970 | | 2931 |

-continued

| | |
|---|---|
| gtc tac cac tcc tac ctc acc atc ttc ggg cag atc ccg ggc tac atc<br>Val Tyr His Ser Tyr Leu Thr Ile Phe Gly Gln Ile Pro Gly Tyr Ile<br>975                        980                   985 | 2979 |
| gac ggt gtg aac ttc aac ccg gag cac tgc agc ccc aat ggc acc gac<br>Asp Gly Val Asn Phe Asn Pro Glu His Cys Ser Pro Asn Gly Thr Asp<br>        990                   995                     1000 | 3027 |
| ccc tac aag cct aag tgc ccc gag agc gac gcg acg cag cag agg ccg<br>Pro Tyr Lys Pro Lys Cys Pro Glu Ser Asp Ala Thr Gln Gln Arg Pro<br>     1005                  1010                1015 | 3075 |
| gcc ttc cct gag tgg ctg acg gtc ctc cta ctc tgc ctc tac ctg ctc<br>Ala Phe Pro Glu Trp Leu Thr Val Leu Leu Leu Cys Leu Tyr Leu Leu<br>1020                   1025                1030 | 3123 |
| ttc acc aac atc ctg ctg ctc aac ctc ctc atc gcc atg ttc aac tac<br>Phe Thr Asn Ile Leu Leu Leu Asn Leu Leu Ile Ala Met Phe Asn Tyr<br>1035              1040              1045             1050 | 3171 |
| acc ttc cag cag gtg cag gag cac acg gac cag att tgg aag ttc cag<br>Thr Phe Gln Gln Val Gln Glu His Thr Asp Gln Ile Trp Lys Phe Gln<br>                 1055              1060              1065 | 3219 |
| cgc cat gac ctg atc gag gag tac cac ggc cgc ccc gcc gcg ccg ccc<br>Arg His Asp Leu Ile Glu Glu Tyr His Gly Arg Pro Ala Ala Pro Pro<br>            1070               1075              1080 | 3267 |
| ccc ttc atc ctc ctc agc cac ctg cag ctc ttc atc aag agg gtg gtc<br>Pro Phe Ile Leu Leu Ser His Leu Gln Leu Phe Ile Lys Arg Val Val<br>1085                 1090               1095 | 3315 |
| ctg aag act ccg gcc aag agg cac aag cag ctc aag aac aag ctg gag<br>Leu Lys Thr Pro Ala Lys Arg His Lys Gln Leu Lys Asn Lys Leu Glu<br>    1100                1105              1110 | 3363 |
| aag aac gag gag gcg gcc ctg cta tcc tgg gag atc tac ctg aag gag<br>Lys Asn Glu Glu Ala Ala Leu Leu Ser Trp Glu Ile Tyr Leu Lys Glu<br>1115               1120               1125             1130 | 3411 |
| aac tac ctc cag aac cga cag ttc cag caa aag cag cgg ccc gag cag<br>Asn Tyr Leu Gln Asn Arg Gln Phe Gln Gln Lys Gln Arg Pro Glu Gln<br>                 1135             1140              1145 | 3459 |
| aag atc gag gac atc agc aat aag gtt gac gcc atg gtg gac ctg ctg<br>Lys Ile Glu Asp Ile Ser Asn Lys Val Asp Ala Met Val Asp Leu Leu<br>           1150               1155              1160 | 3507 |
| gac ctg gac cca ctg aag agg tcg ggc tcc atg gag cag agg ttg gcc<br>Asp Leu Asp Pro Leu Lys Arg Ser Gly Ser Met Glu Gln Arg Leu Ala<br>1165               1170               1175 | 3555 |
| tcc ctg gag gag cag gtg gcc cag aca gcc cga gcc ctg cac tgg atc<br>Ser Leu Glu Glu Gln Val Ala Gln Thr Ala Arg Ala Leu His Trp Ile<br>1180                1185              1190 | 3603 |
| gtg agg acg ctg cgg gcc agc ggc ttc agc tcg gag gcg gac gtc ccc<br>Val Arg Thr Leu Arg Ala Ser Gly Phe Ser Ser Glu Ala Asp Val Pro<br>1195               1200               1205              1210 | 3651 |
| act ctg gcc tcc cag aag gcc gcg gag gag ccg gat gct gag ccg gga<br>Thr Leu Ala Ser Gln Lys Ala Ala Glu Glu Pro Asp Ala Glu Pro Gly<br>             1215              1220               1225 | 3699 |
| ggc agg aag aag acg gag gag ccg ggc gac agc tac cac gtg aat gcc<br>Gly Arg Lys Lys Thr Glu Glu Pro Gly Asp Ser Tyr His Val Asn Ala<br>          1230               1235              1240 | 3747 |
| cgg cac ctc ctc tac ccc aac tgc cct gtc acg cgc ttc ccc gtg ccc<br>Arg His Leu Leu Tyr Pro Asn Cys Pro Val Thr Arg Phe Pro Val Pro<br>              1245              1250              1255 | 3795 |
| aac gag aag gtg ccc tgg gag acg gag ttc ctg atc tat gac cca ccc<br>Asn Glu Lys Val Pro Trp Glu Thr Glu Phe Leu Ile Tyr Asp Pro Pro<br>1260               1265              1270 | 3843 |
| ttt tac acg gca gag agg aag gac gcg gcc gcc atg gac ccc atg gga<br>Phe Tyr Thr Ala Glu Arg Lys Asp Ala Ala Ala Met Asp Pro Met Gly<br>1275               1280               1285              1290 | 3891 |

| | |
|---|---:|
| gac acc ctg gag cca ctg tcc acg atc cag tac aac gtg gtg gat ggc<br>Asp Thr Leu Glu Pro Leu Ser Thr Ile Gln Tyr Asn Val Val Asp Gly<br>                1295                          1300                     1305 | 3939 |
| ctg agg gac cgc cgg agc ttc cac ggg ccg tac aca gtg cag gcc ggg<br>Leu Arg Asp Arg Arg Ser Phe His Gly Pro Tyr Thr Val Gln Ala Gly<br>            1310                         1315                      1320 | 3987 |
| ttg ccc ctg aac ccc atg ggc cgc aca gga ctg cgt ggg cgc ggg agc<br>Leu Pro Leu Asn Pro Met Gly Arg Thr Gly Leu Arg Gly Arg Gly Ser<br>      1325                         1330                     1335 | 4035 |
| ctc agc tgc ttc gga ccc aac cac acg ctg tac ccc atg gtc acg cgg<br>Leu Ser Cys Phe Gly Pro Asn His Thr Leu Tyr Pro Met Val Thr Arg<br>          1340                       1345                     1350 | 4083 |
| tgg agg cgg aac gag gat gga gcc atc tgc agg aag agc ata aag aag<br>Trp Arg Arg Asn Glu Asp Gly Ala Ile Cys Arg Lys Ser Ile Lys Lys<br>1355                     1360                     1365                   1370 | 4131 |
| atg ctg gaa gtg ctg gtg gtg aag ctc cct ctc tcc gag cac tgg gcc<br>Met Leu Glu Val Leu Val Val Lys Leu Pro Leu Ser Glu His Trp Ala<br>                      1375                     1380                     1385 | 4179 |
| ctg cct ggg ggc tcc cgg gag cca ggg gag atg cta cct cgg aag ctg<br>Leu Pro Gly Gly Ser Arg Glu Pro Gly Glu Met Leu Pro Arg Lys Leu<br>          1390                       1395                     1400 | 4227 |
| aag cgg atc ctc cgg cag gag cac tgg ccg tct ttt gaa aac ttg ctg<br>Lys Arg Ile Leu Arg Gln Glu His Trp Pro Ser Phe Glu Asn Leu Leu<br>            1405                       1410                     1415 | 4275 |
| aag tgc ggc atg gag gtg tac aaa ggc tac atg gat gac ccg agg aac<br>Lys Cys Gly Met Glu Val Tyr Lys Gly Tyr Met Asp Asp Pro Arg Asn<br>      1420                       1425                     1430 | 4323 |
| acg gac aat gcc tgg atc gag acg gtg gcc gtc agc gtc cac ttc cag<br>Thr Asp Asn Ala Trp Ile Glu Thr Val Ala Val Ser Val His Phe Gln<br>1435                    1440                     1445                   1450 | 4371 |
| gac cag aat gac gtg gag ctg aac agg ctg aac tct aac ctg cac gcc<br>Asp Gln Asn Asp Val Glu Leu Asn Arg Leu Asn Ser Asn Leu His Ala<br>                   1455                     1460                   1465 | 4419 |
| tgc gac tcg ggg gcc tcc atc cga tgg cag gtg gtg gac agg cgc atc<br>Cys Asp Ser Gly Ala Ser Ile Arg Trp Gln Val Val Asp Arg Arg Ile<br>        1470                       1475                     1480 | 4467 |
| cca ctc tat gcg aac cac aag acc ctc ctc cag aag gca gcc gct gag<br>Pro Leu Tyr Ala Asn His Lys Thr Leu Leu Gln Lys Ala Ala Ala Glu<br>            1485                       1490                   1495 | 4515 |
| ttc ggg gct cac tac tga ctgtgccctc aggctgggcg gctccagtcc<br>Phe Gly Ala His Tyr<br>    1500 | 4563 |
| atagacgttc cccccagaaa ccagggcttc tctctcctga gcctggccag gactcaggct | 4623 |
| gttcctgggc cctgcacatg atggggtttg gtggacccag tgcccctcac ggctgccgca | 4683 |
| agtctgctgc agatgacctc atgaactgga agggtcaag gtgaccccggg aggag | 4738 |

<210> SEQ ID NO 2
<211> LENGTH: 1503
<212> TYPE: PRT
<213> ORGANISM: Homo sapiens

<400> SEQUENCE: 2

Met Glu Pro Ser Ala Leu Arg Lys Ala Gly Ser Glu Gln Glu Glu Gly
1               5                   10                  15

Phe Glu Gly Leu Pro Arg Arg Val Thr Asp Leu Gly Met Val Ser Asn
            20                  25                  30

Leu Arg Arg Ser Asn Ser Ser Leu Phe Lys Ser Trp Arg Leu Gln Cys
        35                  40                  45

```
Pro Phe Gly Asn Asn Asp Lys Gln Glu Ser Leu Ser Ser Trp Ile Pro
    50                  55                  60

Glu Asn Ile Lys Lys Lys Glu Cys Val Tyr Phe Val Glu Ser Ser Lys
65                  70                  75                  80

Leu Ser Asp Ala Gly Lys Val Val Cys Gln Cys Gly Tyr Thr His Glu
                85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His Pro
                245                 250                 255

Thr Gly Ser Phe Pro Ala Glu Tyr Ile Leu Asp Glu Asp Gly Gln Gly
            260                 265                 270

Asn Leu Thr Cys Leu Asp Ser Asn His Ser His Phe Ile Leu Val Asp
        275                 280                 285

Asp Gly Thr His Gly Gln Tyr Gly Val Glu Ile Pro Leu Arg Thr Arg
    290                 295                 300

Leu Glu Lys Phe Ile Ser Glu Gln Thr Lys Glu Arg Gly Gly Val Ala
305                 310                 315                 320

Ile Lys Ile Pro Ile Val Cys Val Val Leu Glu Gly Gly Pro Gly Thr
                325                 330                 335

Leu His Thr Ile Asp Asn Ala Thr Thr Asn Gly Thr Pro Cys Val Val
            340                 345                 350

Val Glu Gly Ser Gly Arg Val Ala Asp Val Ile Ala Gln Val Ala Asn
        355                 360                 365

Leu Pro Val Ser Asp Ile Thr Ile Ser Leu Ile Gln Gln Lys Leu Ser
    370                 375                 380

Val Phe Phe Gln Glu Met Phe Glu Thr Phe Thr Glu Ser Arg Ile Val
385                 390                 395                 400

Glu Trp Thr Lys Lys Ile Gln Asp Ile Val Arg Arg Arg Gln Leu Leu
                405                 410                 415

Thr Val Phe Arg Glu Gly Lys Asp Gly Gln Gln Asp Val Asp Val Ala
            420                 425                 430

Ile Leu Gln Ala Leu Leu Lys Ala Ser Arg Ser Gln Asp His Phe Gly
        435                 440                 445

His Glu Asn Trp Asp His Gln Leu Lys Leu Ala Val Ala Trp Asn Arg
    450                 455                 460
```

-continued

Val Asp Ile Ala Arg Ser Glu Ile Phe Met Asp Glu Trp Gln Trp Lys
465                 470                 475                 480

Pro Ser Asp Leu His Pro Thr Met Thr Ala Ala Leu Ile Ser Asn Lys
                485                 490                 495

Pro Glu Phe Val Lys Leu Phe Leu Glu Asn Gly Val Gln Leu Lys Glu
            500                 505                 510

Phe Val Thr Trp Asp Thr Leu Leu Tyr Leu Tyr Glu Asn Leu Asp Pro
        515                 520                 525

Ser Cys Leu Phe His Ser Lys Leu Gln Lys Val Leu Glu Asp Pro
    530                 535                 540

Glu Arg Pro Ala Cys Ala Pro Ala Ala Pro Arg Leu Gln Met His His
545                 550                 555                 560

Val Ala Gln Val Leu Arg Glu Leu Leu Gly Asp Phe Thr Gln Pro Leu
                565                 570                 575

Tyr Pro Arg Pro Arg His Asn Asp Arg Leu Arg Leu Leu Pro Val
            580                 585                 590

Pro His Val Lys Leu Asn Val Gln Gly Val Ser Leu Arg Ser Leu Tyr
        595                 600                 605

Lys Arg Ser Ser Gly His Val Thr Phe Thr Met Asp Pro Ile Arg Asp
610                 615                 620

Leu Leu Ile Trp Ala Ile Val Gln Asn Arg Arg Glu Leu Ala Gly Ile
625                 630                 635                 640

Ile Trp Ala Gln Ser Gln Asp Cys Ile Ala Ala Leu Ala Cys Ser
                645                 650                 655

Lys Ile Leu Lys Glu Leu Ser Lys Glu Glu Asp Thr Asp Ser Ser
                660                 665                 670

Glu Glu Met Leu Ala Leu Ala Glu Glu Tyr Glu His Arg Ala Ile Gly
                675                 680                 685

Val Phe Thr Glu Cys Tyr Arg Lys Asp Glu Glu Arg Ala Gln Lys Leu
        690                 695                 700

Leu Thr Arg Val Ser Glu Ala Trp Gly Lys Thr Thr Cys Leu Gln Leu
705                 710                 715                 720

Ala Leu Glu Ala Lys Asp Met Lys Phe Val Ser His Gly Gly Ile Gln
                725                 730                 735

Ala Phe Leu Thr Lys Val Trp Trp Gly Gln Leu Ser Val Asp Asn Gly
                740                 745                 750

Leu Trp Arg Val Thr Leu Cys Met Leu Ala Phe Pro Leu Leu Leu Thr
            755                 760                 765

Gly Leu Ile Ser Phe Arg Glu Lys Arg Leu Gln Asp Val Gly Thr Pro
            770                 775                 780

Ala Ala Arg Ala Arg Ala Phe Phe Thr Ala Pro Val Val Phe His
785                 790                 795                 800

Leu Asn Ile Leu Ser Tyr Phe Ala Phe Leu Cys Leu Phe Ala Tyr Val
                805                 810                 815

Leu Met Val Asp Phe Gln Pro Val Pro Ser Trp Cys Glu Cys Ala Ile
            820                 825                 830

Tyr Leu Trp Leu Phe Ser Leu Val Cys Glu Glu Met Arg Gln Leu Phe
            835                 840                 845

Tyr Asp Pro Asp Glu Cys Gly Leu Met Lys Lys Ala Ala Leu Tyr Phe
            850                 855                 860

Ser Asp Phe Trp Asn Lys Leu Asp Val Gly Ala Ile Leu Leu Phe Val
865                 870                 875                 880

Ala Gly Leu Thr Cys Arg Leu Ile Pro Ala Thr Leu Tyr Pro Gly Arg

```
                    885                 890                 895
Val Ile Leu Ser Leu Asp Phe Ile Leu Phe Cys Leu Arg Leu Met His
                900                 905                 910
Ile Phe Thr Ile Ser Lys Thr Leu Gly Pro Lys Ile Ile Val Lys
                915                 920                 925
Arg Met Met Lys Asp Val Phe Phe Leu Phe Leu Leu Ala Val Trp
            930                 935                 940
Val Val Ser Phe Gly Val Ala Lys Gln Ala Ile Leu Ile His Asn Glu
945                 950                 955                 960
Arg Arg Val Asp Trp Leu Phe Arg Gly Ala Val Tyr His Ser Tyr Leu
                965                 970                 975
Thr Ile Phe Gly Gln Ile Pro Gly Tyr Ile Asp Gly Val Asn Phe Asn
            980                 985                 990
Pro Glu His Cys Ser Pro Asn Gly Thr Asp Pro Tyr Lys Pro Lys Cys
                995                 1000                1005
Pro Glu Ser Asp Ala Thr Gln Gln Arg Pro Ala Phe Pro Glu Trp Leu
            1010                1015                1020
Thr Val Leu Leu Leu Cys Leu Tyr Leu Leu Phe Thr Asn Ile Leu Leu
1025                1030                1035                1040
Leu Asn Leu Leu Ile Ala Met Phe Asn Tyr Thr Phe Gln Gln Val Gln
                1045                1050                1055
Glu His Thr Asp Gln Ile Trp Lys Phe Gln Arg His Asp Leu Ile Glu
                1060                1065                1070
Glu Tyr His Gly Arg Pro Ala Ala Pro Pro Pro Phe Ile Leu Leu Ser
                1075                1080                1085
His Leu Gln Leu Phe Ile Lys Arg Val Val Leu Lys Thr Pro Ala Lys
                1090                1095                1100
Arg His Lys Gln Leu Lys Asn Lys Leu Glu Lys Asn Glu Glu Ala Ala
1105                1110                1115                1120
Leu Leu Ser Trp Glu Ile Tyr Leu Lys Glu Asn Tyr Leu Gln Asn Arg
                1125                1130                1135
Gln Phe Gln Gln Lys Gln Arg Pro Glu Gln Lys Ile Glu Asp Ile Ser
                1140                1145                1150
Asn Lys Val Asp Ala Met Val Asp Leu Leu Asp Leu Asp Pro Leu Lys
                1155                1160                1165
Arg Ser Gly Ser Met Glu Gln Arg Leu Ala Ser Leu Glu Glu Gln Val
                1170                1175                1180
Ala Gln Thr Ala Arg Ala Leu His Trp Ile Val Arg Thr Leu Arg Ala
1185                1190                1195                1200
Ser Gly Phe Ser Ser Glu Ala Asp Val Pro Thr Leu Ala Ser Gln Lys
                1205                1210                1215
Ala Ala Glu Glu Pro Asp Ala Glu Pro Gly Gly Arg Lys Lys Thr Glu
                1220                1225                1230
Glu Pro Gly Asp Ser Tyr His Val Asn Ala Arg His Leu Leu Tyr Pro
                1235                1240                1245
Asn Cys Pro Val Thr Arg Phe Pro Val Pro Asn Glu Lys Val Pro Trp
                1250                1255                1260
Glu Thr Glu Phe Leu Ile Tyr Asp Pro Pro Phe Tyr Thr Ala Glu Arg
1265                1270                1275                1280
Lys Asp Ala Ala Ala Met Asp Pro Met Gly Asp Thr Leu Glu Pro Leu
                1285                1290                1295
Ser Thr Ile Gln Tyr Asn Val Val Asp Gly Leu Arg Asp Arg Arg Ser
                1300                1305                1310
```

-continued

```
Phe His Gly Pro Tyr Thr Val Gln Ala Gly Leu Pro Leu Asn Pro Met
        1315                1320                1325
Gly Arg Thr Gly Leu Arg Gly Arg Gly Ser Leu Ser Cys Phe Gly Pro
    1330                1335                1340
Asn His Thr Leu Tyr Pro Met Val Thr Arg Trp Arg Arg Asn Glu Asp
1345                1350                1355                1360
Gly Ala Ile Cys Arg Lys Ser Ile Lys Lys Met Leu Glu Val Leu Val
                1365                1370                1375
Val Lys Leu Pro Leu Ser Glu His Trp Ala Leu Pro Gly Gly Ser Arg
            1380                1385                1390
Glu Pro Gly Glu Met Leu Pro Arg Lys Leu Lys Arg Ile Leu Arg Gln
        1395                1400                1405
Glu His Trp Pro Ser Phe Glu Asn Leu Leu Lys Cys Gly Met Glu Val
    1410                1415                1420
Tyr Lys Gly Tyr Met Asp Asp Pro Arg Asn Thr Asp Asn Ala Trp Ile
1425                1430                1435                1440
Glu Thr Val Ala Val Ser Val His Phe Gln Asp Gln Asn Asp Val Glu
                1445                1450                1455
Leu Asn Arg Leu Asn Ser Asn Leu His Ala Cys Asp Ser Gly Ala Ser
            1460                1465                1470
Ile Arg Trp Gln Val Val Asp Arg Arg Ile Pro Leu Tyr Ala Asn His
        1475                1480                1485
Lys Thr Leu Leu Gln Lys Ala Ala Ala Glu Phe Gly Ala His Tyr
    1490                1495                1500

<210> SEQ ID NO 3
<211> LENGTH: 4738
<212> TYPE: DNA
<213> ORGANISM: Rattus sp.
<220> FEATURE:
<221> NAME/KEY: CDS
<222> LOCATION: (84)..(4610)

<400> SEQUENCE: 3
cccccaacct cacaaatgag aagagacatc cctgaaaggc atctagagat ctctctcctc     60
tggtggatct ggagccgtgg agg atg gag ccc ttg gac cag aga aga act gac    113
                          Met Glu Pro Leu Asp Gln Arg Arg Thr Asp
                            1               5                  10 tct gat caa gag gag ggc ttt ggg gtg cag tcc cgg agg gcc act gat      161
Ser Asp Gln Glu Glu Gly Phe Gly Val Gln Ser Arg Arg Ala Thr Asp
                15                  20                  25 ctg ggc atg gtc ccc aat ctc cga cga agc aat agc agt ctt tgc aag      209
Leu Gly Met Val Pro Asn Leu Arg Arg Ser Asn Ser Ser Leu Cys Lys
         30                  35                  40 agc agg agg ctt ctg tgc tcc ttc agc agt gag aag caa gaa aac ctt      257
Ser Arg Arg Leu Leu Cys Ser Phe Ser Ser Glu Lys Gln Glu Asn Leu
     45                  50                  55 agc tca tgg att ccc gag aac atc aag aag aag gaa tgt gtg tat ttc      305
Ser Ser Trp Ile Pro Glu Asn Ile Lys Lys Lys Glu Cys Val Tyr Phe
 60                  65                  70 gtg gaa agt tcc aag ctc tcg gat gca ggg aag gta gtg tgt gag tgt      353
Val Glu Ser Ser Lys Leu Ser Asp Ala Gly Lys Val Val Cys Glu Cys
 75                  80                  85                  90 ggt tac acc cac gag cag cac att gaa gtg gcc atc aag cct cac acc      401
Gly Tyr Thr His Glu Gln His Ile Glu Val Ala Ile Lys Pro His Thr
                 95                 100                 105 ttc cag ggc aag gag tgg gac cca aag aaa cac gtc cat gag atg cct      449
```

```
                                                        -continued

Phe Gln Gly Lys Glu Trp Asp Pro Lys Lys His Val His Glu Met Pro
            110                 115                 120 aca gat gcc ttt ggt gac att gtc ttc acc ggc ctg agc cag aaa gtg    497
Thr Asp Ala Phe Gly Asp Ile Val Phe Thr Gly Leu Ser Gln Lys Val
            125                 130                 135 ggg aag tat gtc cga ctc tcc cag gac acg tcg tcc att gtc atc tac    545
Gly Lys Tyr Val Arg Leu Ser Gln Asp Thr Ser Ser Ile Val Ile Tyr
        140                 145                 150 cag ctt atg aca cag cac tgg ggc ctg gat gtc ccc agc ctc ctc atc    593
Gln Leu Met Thr Gln His Trp Gly Leu Asp Val Pro Ser Leu Leu Ile
155             160                 165                 170 tct gtg acc ggt ggg gcc aag aac ttc aac atg aag ctg agg ttg aag    641
Ser Val Thr Gly Gly Ala Lys Asn Phe Asn Met Lys Leu Arg Leu Lys
                175                 180                 185 agc atc ttc cgg aga ggc ctg gtt aag gtg gcc caa acc acg ggg gcc    689
Ser Ile Phe Arg Arg Gly Leu Val Lys Val Ala Gln Thr Thr Gly Ala
            190                 195                 200 tgg atc atc act ggg ggt tcc cac acc ggt gtg atg aag cag gtg ggc    737
Trp Ile Ile Thr Gly Gly Ser His Thr Gly Val Met Lys Gln Val Gly
            205                 210                 215 gag gcg gta cgg gac ttc agc cta agc agc agc tgc aaa gaa ggc gac    785
Glu Ala Val Arg Asp Phe Ser Leu Ser Ser Ser Cys Lys Glu Gly Asp
        220                 225                 230 gtc atc acc atc ggc ata gcc acg tgg ggc acc atc cac aac cgt gag    833
Val Ile Thr Ile Gly Ile Ala Thr Trp Gly Thr Ile His Asn Arg Glu
235             240                 245                 250 gca ctg atc cat ccc atg gga ggc ttc ccc gct gag tac atg ctg gat    881
Ala Leu Ile His Pro Met Gly Gly Phe Pro Ala Glu Tyr Met Leu Asp
                255                 260                 265 gag gaa ggc caa ggg aac ctg acc tgc ctg gac agc aac cac tcc cac    929
Glu Glu Gly Gln Gly Asn Leu Thr Cys Leu Asp Ser Asn His Ser His
            270                 275                 280 ttc atc ctg gtg gat gat ggg acc cac ggg cag tat ggt gtg gag att    977
Phe Ile Leu Val Asp Asp Gly Thr His Gly Gln Tyr Gly Val Glu Ile
            285                 290                 295 ccg ctg agg act aag ctg gag aag ttc ata tcg gag caa acg aag gaa   1025
Pro Leu Arg Thr Lys Leu Glu Lys Phe Ile Ser Glu Gln Thr Lys Glu
        300                 305                 310 aga ggg ggt gtg gcc att aag atc ccc att gtc tgc gtg gtg ttg gag   1073
Arg Gly Gly Val Ala Ile Lys Ile Pro Ile Val Cys Val Val Leu Glu
315             320                 325                 330 ggt ggc cct ggc act ctg cat acc atc tac aac gcc atc acc aat ggc   1121
Gly Gly Pro Gly Thr Leu His Thr Ile Tyr Asn Ala Ile Thr Asn Gly
                335                 340                 345 aca ccc tgc gtg ata gtg gag ggc tcc ggc cga gtg gct gac gtc atc   1169
Thr Pro Cys Val Ile Val Glu Gly Ser Gly Arg Val Ala Asp Val Ile
            350                 355                 360 gct cag gtg gcc gct ctg ccc gtc tct gag atc acc atc tcc ctg atc   1217
Ala Gln Val Ala Ala Leu Pro Val Ser Glu Ile Thr Ile Ser Leu Ile
        365                 370                 375 cag cag aag ctc agc gtc ttc ttc cag gag atg ttt gag act ttc acc   1265
Gln Gln Lys Leu Ser Val Phe Phe Gln Glu Met Phe Glu Thr Phe Thr
            380                 385                 390 gaa aac cag att gtg gaa tgg acc aaa aag atc caa gat att gtc agg   1313
Glu Asn Gln Ile Val Glu Trp Thr Lys Lys Ile Gln Asp Ile Val Arg
395             400                 405                 410 agg cgg cag ctg ctg acg gtc ttc cgg gaa ggc aag gat ggt cag cag   1361
Arg Arg Gln Leu Leu Thr Val Phe Arg Glu Gly Lys Asp Gly Gln Gln
            415                 420                 425
```

-continued

```
gat gtg gat gtt gcc att ctg caa gct tta ctg aaa gcc tct cga agc         1409
Asp Val Asp Val Ala Ile Leu Gln Ala Leu Leu Lys Ala Ser Arg Ser
        430                 435                 440 caa gat cac ttc ggc cac gag aac tgg gac cat cag ctg aag ctg gcc         1457
Gln Asp His Phe Gly His Glu Asn Trp Asp His Gln Leu Lys Leu Ala
            445                 450                 455 gtg gcc tgg aac cgt gtg gac atc gcc cgc agt gag atc ttc act gat         1505
Val Ala Trp Asn Arg Val Asp Ile Ala Arg Ser Glu Ile Phe Thr Asp
460                 465                 470 gag tgg cag tgg aag cct tca gac ctg cat ccc atg atg aca gct gcc         1553
Glu Trp Gln Trp Lys Pro Ser Asp Leu His Pro Met Met Thr Ala Ala
475                 480                 485                 490 ctc atc tcc aac aag cct gag ttt gtg agg ctc ttt ctg gag aac ggg         1601
Leu Ile Ser Asn Lys Pro Glu Phe Val Arg Leu Phe Leu Glu Asn Gly
                495                 500                 505 gtg cgg ctg aag gag ttt gtc acc tgg gat act ctt ctc tgc ctc tac         1649
Val Arg Leu Lys Glu Phe Val Thr Trp Asp Thr Leu Leu Cys Leu Tyr
            510                 515                 520 gag aac ctg gag cca tcc tgc ctt ttc cac agc aag ctg cag aag gtg         1697
Glu Asn Leu Glu Pro Ser Cys Leu Phe His Ser Lys Leu Gln Lys Val
        525                 530                 535 ctg gca gaa gag cat gaa cgc tta gcc tat gca tct gag aca ccc cgg         1745
Leu Ala Glu Glu His Glu Arg Leu Ala Tyr Ala Ser Glu Thr Pro Arg
    540                 545                 550 ctg caa atg cac cac gtg gcc cag gtg ctg cgt gag ctc ctc gga gac         1793
Leu Gln Met His His Val Ala Gln Val Leu Arg Glu Leu Leu Gly Asp
555                 560                 565                 570 tcc aca cag ctg ctg tat ccc cgg ccc cgg tac act gac cgg cca cgg         1841
Ser Thr Gln Leu Leu Tyr Pro Arg Pro Arg Tyr Thr Asp Arg Pro Arg
                575                 580                 585 ctc tcg ctg ccc atg cca cac atc aaa ctc aac gtg caa gga gtg agc         1889
Leu Ser Leu Pro Met Pro His Ile Lys Leu Asn Val Gln Gly Val Ser
            590                 595                 600 ctc cgg tct ctc tat aag cga tca aca ggc cac gtt acc ttc acc att         1937
Leu Arg Ser Leu Tyr Lys Arg Ser Thr Gly His Val Thr Phe Thr Ile
        605                 610                 615 gac cca gtc cgc gat ctt ctc att tgg gcc atc atc cag aac cac agg         1985
Asp Pro Val Arg Asp Leu Leu Ile Trp Ala Ile Ile Gln Asn His Arg
    620                 625                 630 gag ctg gcg ggc atc atc tgg gct cag agc cag gac tgc aca gca gcc         2033
Glu Leu Ala Gly Ile Ile Trp Ala Gln Ser Gln Asp Cys Thr Ala Ala
635                 640                 645                 650 gca ctg gcc tgc agc aag atc ctg aag gag ctg tcc aag gag gag gaa         2081
Ala Leu Ala Cys Ser Lys Ile Leu Lys Glu Leu Ser Lys Glu Glu Glu
                655                 660                 665 gat aca gac agc tct gag gag atg ctg gca ctc gcg gat gag ttt gag         2129
Asp Thr Asp Ser Ser Glu Glu Met Leu Ala Leu Ala Asp Glu Phe Glu
            670                 675                 680 cat aga gct atc ggt gtc ttc acc gag tgc tac aga aag gat gag gaa         2177
His Arg Ala Ile Gly Val Phe Thr Glu Cys Tyr Arg Lys Asp Glu Glu
        685                 690                 695 aga gcc cag aag ctg ctt gtc cgt gtg tct gag gcc tgg ggg aag acc         2225
Arg Ala Gln Lys Leu Leu Val Arg Val Ser Glu Ala Trp Gly Lys Thr
    700                 705                 710 acc tgc ctg cag ctg gcc ctc gag gcc aag gac atg aaa ttc gtg tct         2273
Thr Cys Leu Gln Leu Ala Leu Glu Ala Lys Asp Met Lys Phe Val Ser
715                 720                 725                 730 cac gga ggg atc cag gct ttc cta acg aag gtg tgg tgg ggt cag ctc         2321
His Gly Gly Ile Gln Ala Phe Leu Thr Lys Val Trp Trp Gly Gln Leu
                735                 740                 745
```

-continued

| | |
|---|---|
| tgc gtg gac aat ggc ctg tgg agg atc atc ctg tgc atg ctg gcc ttc<br>Cys Val Asp Asn Gly Leu Trp Arg Ile Ile Leu Cys Met Leu Ala Phe<br>750                          755                          760 | 2369 |
| cct ctg ctc ttc acc ggc ttc atc tcc ttc agg gaa aag agg ctg cag<br>Pro Leu Leu Phe Thr Gly Phe Ile Ser Phe Arg Glu Lys Arg Leu Gln<br>765                          770                          775 | 2417 |
| gca ctg tgc cgc ccg gcc cgc gtc cgc gcc ttc ttc aac gcg ccg gtg<br>Ala Leu Cys Arg Pro Ala Arg Val Arg Ala Phe Phe Asn Ala Pro Val<br>780                          785                          790 | 2465 |
| gtc atc ttc tac ctc aat att ctc tcc tac ttt gcc ttc ctc tgc ctg<br>Val Ile Phe Tyr Leu Asn Ile Leu Ser Tyr Phe Ala Phe Leu Cys Leu<br>795                          800                          805          810 | 2513 |
| ttt gcc tac gtg ctc atg gtg gac ttc cag ccc tca cca tcc tgg tgc<br>Phe Ala Tyr Val Leu Met Val Asp Phe Gln Pro Ser Pro Ser Trp Cys<br>                         815                          820                          825 | 2561 |
| gag tac ctc atc tac ctg tgg ctc ttc tcc ctg gtg tgc gag gag aca<br>Glu Tyr Leu Ile Tyr Leu Trp Leu Phe Ser Leu Val Cys Glu Glu Thr<br>                         830                          835                          840 | 2609 |
| cgg cag cta ttc tac gat ccc gat ggc tgc ggg ctc atg aag atg gcg<br>Arg Gln Leu Phe Tyr Asp Pro Asp Gly Cys Gly Leu Met Lys Met Ala<br>                         845                          850                          855 | 2657 |
| tcc ctg tac ttc agt gac ttc tgg aac aaa ctg gac gtt ggg gcc att<br>Ser Leu Tyr Phe Ser Asp Phe Trp Asn Lys Leu Asp Val Gly Ala Ile<br>860                          865                          870 | 2705 |
| ctg ctc ttt ata gca gga ctg acc tgc cga ctc atc cca gcg acg ctg<br>Leu Leu Phe Ile Ala Gly Leu Thr Cys Arg Leu Ile Pro Ala Thr Leu<br>875                          880                          885          890 | 2753 |
| tac cct ggg cgc atc atc ctg tct ttg gac ttc att atg ttc tgc ctc<br>Tyr Pro Gly Arg Ile Ile Leu Ser Leu Asp Phe Ile Met Phe Cys Leu<br>                         895                          900                          905 | 2801 |
| cgc ctc atg cac atc ttc acc att agc aag aca ctg ggg ccc aag ata<br>Arg Leu Met His Ile Phe Thr Ile Ser Lys Thr Leu Gly Pro Lys Ile<br>                         910                          915                          920 | 2849 |
| atc atc gtg aag cgg atg atg aag gac gtc ttc ttc ctc ttt ctc<br>Ile Ile Val Lys Arg Met Met Lys Asp Val Phe Phe Phe Leu Phe Leu<br>                         925                          930                          935 | 2897 |
| ctg gcg gtg tgg gtg gtg tcc ttc gga gtg gcc aag cag gcc atc ctc<br>Leu Ala Val Trp Val Val Ser Phe Gly Val Ala Lys Gln Ala Ile Leu<br>940                          945                          950 | 2945 |
| atc cac aat gag agc cgc gtg gac tgg atc ttc cgc gga gtt atc tat<br>Ile His Asn Glu Ser Arg Val Asp Trp Ile Phe Arg Gly Val Ile Tyr<br>955                          960                          965                          970 | 2993 |
| cac tct tac ctt acc atc ttc ggg cag atc ccg acc tac att gac ggc<br>His Ser Tyr Leu Thr Ile Phe Gly Gln Ile Pro Thr Tyr Ile Asp Gly<br>                         975                          980                          985 | 3041 |
| gtg aat ttc agc atg gac cag tgc agc ccc aat ggt aca gac ccc tac<br>Val Asn Phe Ser Met Asp Gln Cys Ser Pro Asn Gly Thr Asp Pro Tyr<br>                         990                          995                        1000 | 3089 |
| aag ccc aag tgt cct gag agt gac tgg aca ggg cag gca ccc gcc ttc<br>Lys Pro Lys Cys Pro Glu Ser Asp Trp Thr Gly Gln Ala Pro Ala Phe<br>                    1005                     1010                     1015 | 3137 |
| ccc gag tgg ctg aca gtc acc ctt ctc tgc ctc tac ctg ctc ttc gcc<br>Pro Glu Trp Leu Thr Val Thr Leu Leu Cys Leu Tyr Leu Leu Phe Ala<br>1020                     1025                     1030 | 3185 |
| aac atc ctg ctg ctt aat ttg ctc atc gcc atg ttc aac tac acc ttc<br>Asn Ile Leu Leu Leu Asn Leu Leu Ile Ala Met Phe Asn Tyr Thr Phe<br>1035                     1040                     1045                     1050 | 3233 |
| cag gag gtg cag gag cac aca gac cag atc tgg aag ttc cag cgc cac<br>Gln Glu Val Gln Glu His Thr Asp Gln Ile Trp Lys Phe Gln Arg His | 3281 |

-continued

|  |  |  |  |
|---|---|---|---|
| gac ctg att gag gag tac cac ggc cgg ccc ccg gcc cct ccc cca ctc<br>Asp Leu Ile Glu Glu Tyr His Gly Arg Pro Pro Ala Pro Pro Pro Leu<br>                                          1070                                1075                                1080 | 3329 |

```
                        1055                    1060                    1065
gac ctg att gag gag tac cac ggc cgg ccc ccg gcc cct ccc cca ctc      3329
Asp Leu Ile Glu Glu Tyr His Gly Arg Pro Pro Ala Pro Pro Pro Leu
                1070                    1075                    1080 atc ctc ctc agc cac ctg cag ctc ctg atc aag agg att gtc ctg aag      3377
Ile Leu Leu Ser His Leu Gln Leu Leu Ile Lys Arg Ile Val Leu Lys
        1085                    1090                    1095 atc ccc gcc aag agg cac aag cag ctc aag aac aag ctg gag aag aat      3425
Ile Pro Ala Lys Arg His Lys Gln Leu Lys Asn Lys Leu Glu Lys Asn
    1100                    1105                    1110 gag gag gca gcc ctc ctg tcc tgg gag ctc tac ctg aag gag aat tac      3473
Glu Glu Ala Ala Leu Leu Ser Trp Glu Leu Tyr Leu Lys Glu Asn Tyr
1115                    1120                    1125                    1130 ctg cag aac caa cag tac cag cac aaa cag cgg cca gag cag aag atc      3521
Leu Gln Asn Gln Gln Tyr Gln His Lys Gln Arg Pro Glu Gln Lys Ile
                1135                    1140                    1145 cag gac atc agt gag aaa gtg gac acc atg gtg gat ctg ttg gac atg      3569
Gln Asp Ile Ser Glu Lys Val Asp Thr Met Val Asp Leu Leu Asp Met
        1150                    1155                    1160 gac cgt gtg aag aga tca ggc tcc aca gag cag agg ctg gcc tcc ctt      3617
Asp Arg Val Lys Arg Ser Gly Ser Thr Glu Gln Arg Leu Ala Ser Leu
    1165                    1170                    1175 gag gaa cag gtg act cag atg ggc aga tct ttg cac tgg atc gtg acg      3665
Glu Glu Gln Val Thr Gln Met Gly Arg Ser Leu His Trp Ile Val Thr
1180                    1185                    1190 acc ctg aag gac agt ggc ttt ggc tca ggg gcc ggt gca ctg acc ctg      3713
Thr Leu Lys Asp Ser Gly Phe Gly Ser Gly Ala Gly Ala Leu Thr Leu
1195                    1200                    1205                    1210 gca gcc caa agg gcc ttc gac gag cca gat gct gag ctg agt atc agg      3761
Ala Ala Gln Arg Ala Phe Asp Glu Pro Asp Ala Glu Leu Ser Ile Arg
                1215                    1220                    1225 aag aaa gga gag gag gga gga gat ggc tat cat gtg agc gcc cgg cac      3809
Lys Lys Gly Glu Glu Gly Gly Asp Gly Tyr His Val Ser Ala Arg His
        1230                    1235                    1240 ctc ctc tac cct gat gcc cgc atc atg cgc ttc ccc gtg cct aat gag      3857
Leu Leu Tyr Pro Asp Ala Arg Ile Met Arg Phe Pro Val Pro Asn Glu
    1245                    1250                    1255 aag gtg cct tgg gag gca gag ttt ctg atc tac gac cct ccg ttt tac      3905
Lys Val Pro Trp Glu Ala Glu Phe Leu Ile Tyr Asp Pro Pro Phe Tyr
1260                    1265                    1270 aca gct gag aag aag gat gcg act ctc aca gac cct gtg gga gac act      3953
Thr Ala Glu Lys Lys Asp Ala Thr Leu Thr Asp Pro Val Gly Asp Thr
1275                    1280                    1285                    1290 gca gaa cct ctg tct aag atc aat tac aac gtc gtg gac gga ctg atg      4001
Ala Glu Pro Leu Ser Lys Ile Asn Tyr Asn Val Val Asp Gly Leu Met
                1295                    1300                    1305 gac cgt tgc agc ttc cat ggg acc tat gtg gtc caa tat gga ttc cct      4049
Asp Arg Cys Ser Phe His Gly Thr Tyr Val Val Gln Tyr Gly Phe Pro
        1310                    1315                    1320 ttg aac ccc atg ggc cgc acc ggg ttg cgt ggt cgt ggg agc ctc agc      4097
Leu Asn Pro Met Gly Arg Thr Gly Leu Arg Gly Arg Gly Ser Leu Ser
    1325                    1330                    1335 tgg ttt ggt ccc aac cac act ctg cag cca gtt gtt acc cgg tgg aag      4145
Trp Phe Gly Pro Asn His Thr Leu Gln Pro Val Val Thr Arg Trp Lys
1340                    1345                    1350 agg aac cag ggt gga ggc atc tgc cgg aag agt gtc agg aag atg ttg      4193
Arg Asn Gln Gly Gly Gly Ile Cys Arg Lys Ser Val Arg Lys Met Leu
1355                    1360                    1365                    1370 gag gtg ctg gtc atg aag ttg cct caa tcc gag cac tgg gcc ttg cct      4241
```

-continued

```
Glu Val Leu Val Met Lys Leu Pro Gln Ser Glu His Trp Ala Leu Pro
                1375                1380                1385 ggg ggc tct cgg gag cca ggg aag atg cta cca cgg aag ctg aaa cag      4289
Gly Gly Ser Arg Glu Pro Gly Lys Met Leu Pro Arg Lys Leu Lys Gln
        1390                1395                1400 gtc ctc cag cag gag tac tgg gtg acc ttt gag acc ttg cta agg caa      4337
Val Leu Gln Gln Glu Tyr Trp Val Thr Phe Glu Thr Leu Leu Arg Gln
        1405                1410                1415 ggt aca gag gtg tac aaa gga tac gtg gat gac cca agg aac acg gac      4385
Gly Thr Glu Val Tyr Lys Gly Tyr Val Asp Asp Pro Arg Asn Thr Asp
        1420                1425                1430 aat gcc tgg atc gag acg gtg gct gtc agc atc cat ttc cag gac cag      4433
Asn Ala Trp Ile Glu Thr Val Ala Val Ser Ile His Phe Gln Asp Gln
1435                1440                1445                1450 aat gat gtg gag ctg aag agg ctg gaa gag aac ctg caa act cat gat      4481
Asn Asp Val Glu Leu Lys Arg Leu Glu Glu Asn Leu Gln Thr His Asp
                1455                1460                1465 cca aag gag tcg gcc cgt ggc ttg gag atg tct act gaa tgg cag gtt      4529
Pro Lys Glu Ser Ala Arg Gly Leu Glu Met Ser Thr Glu Trp Gln Val
        1470                1475                1480 gta gac cgg cgg atc cct ctg tat gtg aac cac aag aag atc ctc caa      4577
Val Asp Arg Arg Ile Pro Leu Tyr Val Asn His Lys Lys Ile Leu Gln
        1485                1490                1495 aag gtg gcc tcg ctg ttt ggc gct cac ttc tga ccgtgggttc ttgtggaagc    4630
Lys Val Ala Ser Leu Phe Gly Ala His Phe
        1500                1505 tccagggaa ggggtgatca tccatcaatg acccccctcc aagacttgga ctgggtggca    4690
ggttggggta ctgggttggg gtggtaggtt gttgggctgg gttgggtg               4738

<210> SEQ ID NO 4
<211> LENGTH: 1508
<212> TYPE: PRT
<213> ORGANISM: Rattus sp.

<400> SEQUENCE: 4

Met Glu Pro Leu Asp Gln Arg Arg Thr Asp Ser Asp Gln Glu Glu Gly
 1                5                  10                  15

Phe Gly Val Gln Ser Arg Arg Ala Thr Asp Leu Gly Met Val Pro Asn
                 20                  25                  30

Leu Arg Arg Ser Asn Ser Ser Leu Cys Lys Ser Arg Arg Leu Leu Cys
             35                  40                  45

Ser Phe Ser Ser Glu Lys Gln Glu Asn Leu Ser Trp Ile Pro Glu
     50                  55                  60

Asn Ile Lys Lys Lys Glu Cys Val Tyr Phe Val Glu Ser Ser Lys Leu
 65                  70                  75                  80

Ser Asp Ala Gly Lys Val Val Cys Glu Cys Gly Tyr Thr His Glu Gln
                 85                  90                  95

His Ile Glu Val Ala Ile Lys Pro His Thr Phe Gln Gly Lys Glu Trp
                100                 105                 110

Asp Pro Lys Lys His Val His Glu Met Pro Thr Asp Ala Phe Gly Asp
            115                 120                 125

Ile Val Phe Thr Gly Leu Ser Gln Lys Val Gly Lys Tyr Val Arg Leu
        130                 135                 140

Ser Gln Asp Thr Ser Ser Ile Val Ile Tyr Gln Leu Met Thr Gln His
145                 150                 155                 160

Trp Gly Leu Asp Val Pro Ser Leu Leu Ile Ser Val Thr Gly Gly Ala
                165                 170                 175
```

-continued

```
Lys Asn Phe Asn Met Lys Leu Arg Leu Lys Ser Ile Phe Arg Arg Gly
            180                 185                 190

Leu Val Lys Val Ala Gln Thr Thr Gly Ala Trp Ile Ile Thr Gly Gly
        195                 200                 205

Ser His Thr Gly Val Met Lys Gln Val Gly Glu Ala Val Arg Asp Phe
    210                 215                 220

Ser Leu Ser Ser Cys Lys Glu Gly Asp Val Ile Thr Ile Gly Ile
225                 230                 235                 240

Ala Thr Trp Gly Thr Ile His Asn Arg Glu Ala Leu Ile His Pro Met
                245                 250                 255

Gly Gly Phe Pro Ala Glu Tyr Met Leu Asp Glu Gly Gln Gly Asn
            260                 265                 270

Leu Thr Cys Leu Asp Ser Asn His Ser His Phe Ile Leu Val Asp Asp
        275                 280                 285

Gly Thr His Gly Gln Tyr Gly Val Glu Ile Pro Leu Arg Thr Lys Leu
    290                 295                 300

Glu Lys Phe Ile Ser Glu Gln Thr Lys Glu Arg Gly Gly Val Ala Ile
305                 310                 315                 320

Lys Ile Pro Ile Val Cys Val Leu Glu Gly Gly Pro Gly Thr Leu
                325                 330                 335

His Thr Ile Tyr Asn Ala Ile Thr Asn Gly Thr Pro Cys Val Ile Val
            340                 345                 350

Glu Gly Ser Gly Arg Val Ala Asp Val Ile Ala Gln Val Ala Ala Leu
        355                 360                 365

Pro Val Ser Glu Ile Thr Ile Ser Leu Ile Gln Gln Lys Leu Ser Val
    370                 375                 380

Phe Phe Gln Glu Met Phe Glu Thr Phe Thr Glu Asn Gln Ile Val Glu
385                 390                 395                 400

Trp Thr Lys Lys Ile Gln Asp Ile Val Arg Arg Gln Leu Leu Thr
                405                 410                 415

Val Phe Arg Glu Gly Lys Asp Gly Gln Gln Asp Val Asp Val Ala Ile
            420                 425                 430

Leu Gln Ala Leu Leu Lys Ala Ser Arg Ser Gln Asp His Phe Gly His
        435                 440                 445

Glu Asn Trp Asp His Gln Leu Lys Leu Ala Val Ala Trp Asn Arg Val
    450                 455                 460

Asp Ile Ala Arg Ser Glu Ile Phe Thr Asp Glu Trp Gln Trp Lys Pro
465                 470                 475                 480

Ser Asp Leu His Pro Met Met Thr Ala Ala Leu Ile Ser Asn Lys Pro
                485                 490                 495

Glu Phe Val Arg Leu Phe Leu Glu Asn Gly Val Arg Leu Lys Glu Phe
            500                 505                 510

Val Thr Trp Asp Thr Leu Leu Cys Leu Tyr Glu Asn Leu Glu Pro Ser
        515                 520                 525

Cys Leu Phe His Ser Lys Leu Gln Lys Val Leu Ala Glu Glu His Glu
    530                 535                 540

Arg Leu Ala Tyr Ala Ser Glu Thr Pro Arg Leu Gln Met His His Val
545                 550                 555                 560

Ala Gln Val Leu Arg Glu Leu Leu Gly Asp Ser Thr Gln Leu Leu Tyr
                565                 570                 575

Pro Arg Pro Arg Tyr Thr Asp Arg Pro Arg Leu Ser Leu Pro Met Pro
            580                 585                 590
```

-continued

```
His Ile Lys Leu Asn Val Gln Gly Val Ser Leu Arg Ser Leu Tyr Lys
        595                 600                 605

Arg Ser Thr Gly His Val Thr Phe Thr Ile Asp Pro Val Arg Asp Leu
        610                 615                 620

Leu Ile Trp Ala Ile Ile Gln Asn His Arg Glu Leu Ala Gly Ile Ile
625                 630                 635                 640

Trp Ala Gln Ser Gln Asp Cys Thr Ala Ala Leu Ala Cys Ser Lys
                645                 650                 655

Ile Leu Lys Glu Leu Ser Lys Glu Glu Asp Thr Asp Ser Ser Glu
                660                 665                 670

Glu Met Leu Ala Leu Ala Asp Glu Phe Glu His Arg Ala Ile Gly Val
        675                 680                 685

Phe Thr Glu Cys Tyr Arg Lys Asp Glu Glu Arg Ala Gln Lys Leu Leu
        690                 695                 700

Val Arg Val Ser Glu Ala Trp Gly Lys Thr Thr Cys Leu Gln Leu Ala
705                 710                 715                 720

Leu Glu Ala Lys Asp Met Lys Phe Val Ser His Gly Gly Ile Gln Ala
                725                 730                 735

Phe Leu Thr Lys Val Trp Trp Gly Gln Leu Cys Val Asp Asn Gly Leu
        740                 745                 750

Trp Arg Ile Ile Leu Cys Met Leu Ala Phe Pro Leu Leu Phe Thr Gly
        755                 760                 765

Phe Ile Ser Phe Arg Glu Lys Arg Leu Gln Ala Leu Cys Arg Pro Ala
        770                 775                 780

Arg Val Arg Ala Phe Phe Asn Ala Pro Val Val Ile Phe Tyr Leu Asn
785                 790                 795                 800

Ile Leu Ser Tyr Phe Ala Phe Leu Cys Leu Phe Ala Tyr Val Leu Met
                805                 810                 815

Val Asp Phe Gln Pro Ser Pro Ser Trp Cys Glu Tyr Leu Ile Tyr Leu
        820                 825                 830

Trp Leu Phe Ser Leu Val Cys Glu Glu Thr Arg Gln Leu Phe Tyr Asp
        835                 840                 845

Pro Asp Gly Cys Gly Leu Met Lys Met Ala Ser Leu Tyr Phe Ser Asp
        850                 855                 860

Phe Trp Asn Lys Leu Asp Val Gly Ala Ile Leu Leu Phe Ile Ala Gly
865                 870                 875                 880

Leu Thr Cys Arg Leu Ile Pro Ala Thr Leu Tyr Pro Gly Arg Ile Ile
                885                 890                 895

Leu Ser Leu Asp Phe Ile Met Phe Cys Leu Arg Leu Met His Ile Phe
        900                 905                 910

Thr Ile Ser Lys Thr Leu Gly Pro Lys Ile Ile Val Lys Arg Met
        915                 920                 925

Met Lys Asp Val Phe Phe Phe Leu Phe Leu Leu Ala Val Trp Val Val
        930                 935                 940

Ser Phe Gly Val Ala Lys Gln Ala Ile Leu Ile His Asn Glu Ser Arg
945                 950                 955                 960

Val Asp Trp Ile Phe Arg Gly Val Ile Tyr His Ser Tyr Leu Thr Ile
                965                 970                 975

Phe Gly Gln Ile Pro Thr Tyr Ile Asp Gly Val Asn Phe Ser Met Asp
        980                 985                 990

Gln Cys Ser Pro Asn Gly Thr Asp Pro Tyr Lys Pro Lys Cys Pro Glu
        995                 1000                1005

Ser Asp Trp Thr Gly Gln Ala Pro Ala Phe Pro Glu Trp Leu Thr Val
```

-continued

```
              1010                1015                1020
Thr Leu Leu Cys Leu Tyr Leu Leu Phe Ala Asn Ile Leu Leu Asn
1025                1030                1035                1040

Leu Leu Ile Ala Met Phe Asn Tyr Thr Phe Gln Glu Val Gln Glu His
                    1045                1050                1055

Thr Asp Gln Ile Trp Lys Phe Gln Arg His Asp Leu Ile Glu Glu Tyr
                1060                1065                1070

His Gly Arg Pro Pro Ala Pro Pro Leu Ile Leu Ser His Leu
            1075                1080                1085

Gln Leu Leu Ile Lys Arg Ile Val Leu Lys Ile Pro Ala Lys Arg His
    1090                1095                1100

Lys Gln Leu Lys Asn Lys Leu Glu Lys Asn Glu Glu Ala Ala Leu Leu
1105                1110                1115                1120

Ser Trp Glu Leu Tyr Leu Lys Glu Asn Tyr Leu Gln Asn Gln Gln Tyr
                    1125                1130                1135

Gln His Lys Gln Arg Pro Glu Gln Lys Ile Gln Asp Ile Ser Glu Lys
                1140                1145                1150

Val Asp Thr Met Val Asp Leu Leu Asp Met Asp Arg Val Lys Arg Ser
            1155                1160                1165

Gly Ser Thr Glu Gln Arg Leu Ala Ser Leu Glu Glu Gln Val Thr Gln
    1170                1175                1180

Met Gly Arg Ser Leu His Trp Ile Val Thr Thr Leu Lys Asp Ser Gly
1185                1190                1195                1200

Phe Gly Ser Gly Ala Gly Ala Leu Thr Leu Ala Ala Gln Arg Ala Phe
                    1205                1210                1215

Asp Glu Pro Asp Ala Glu Leu Ser Ile Arg Lys Lys Gly Glu Glu Gly
                1220                1225                1230

Gly Asp Gly Tyr His Val Ser Ala Arg His Leu Leu Tyr Pro Asp Ala
            1235                1240                1245

Arg Ile Met Arg Phe Pro Val Pro Asn Glu Lys Val Pro Trp Glu Ala
    1250                1255                1260

Glu Phe Leu Ile Tyr Asp Pro Pro Phe Tyr Thr Ala Glu Lys Lys Asp
1265                1270                1275                1280

Ala Thr Leu Thr Asp Pro Val Gly Asp Thr Ala Glu Pro Leu Ser Lys
                    1285                1290                1295

Ile Asn Tyr Asn Val Val Asp Gly Leu Met Asp Arg Cys Ser Phe His
                1300                1305                1310

Gly Thr Tyr Val Val Gln Tyr Gly Phe Pro Leu Asn Pro Met Gly Arg
            1315                1320                1325

Thr Gly Leu Arg Gly Arg Gly Ser Leu Ser Trp Phe Gly Pro Asn His
1330                1335                1340

Thr Leu Gln Pro Val Val Thr Arg Trp Lys Arg Asn Gln Gly Gly Gly
1345                1350                1355                1360

Ile Cys Arg Lys Ser Val Arg Lys Met Leu Glu Val Leu Val Met Lys
                    1365                1370                1375

Leu Pro Gln Ser Glu His Trp Ala Leu Pro Gly Gly Ser Arg Glu Pro
                1380                1385                1390

Gly Lys Met Leu Pro Arg Lys Leu Lys Gln Val Leu Gln Gln Glu Tyr
            1395                1400                1405

Trp Val Thr Phe Glu Thr Leu Leu Arg Gln Gly Thr Glu Val Tyr Lys
    1410                1415                1420

Gly Tyr Val Asp Asp Pro Arg Asn Thr Asp Asn Ala Trp Ile Glu Thr
1425                1430                1435                1440
```

```
Val Ala Val Ser Ile His Phe Gln Asp Gln Asn Asp Val Glu Leu Lys
            1445                1450                1455

Arg Leu Glu Glu Asn Leu Gln Thr His Asp Pro Lys Glu Ser Ala Arg
        1460                1465                1470

Gly Leu Glu Met Ser Thr Glu Trp Gln Val Val Asp Arg Arg Ile Pro
    1475                1480                1485

Leu Tyr Val Asn His Lys Lys Ile Leu Gln Lys Val Ala Ser Leu Phe
      1490                1495                1500

Gly Ala His Phe
1505

<210> SEQ ID NO 5
<211> LENGTH: 18
<212> TYPE: DNA
<213> ORGANISM: Homo sapiens

<400> SEQUENCE: 5
agctggcgtg ggggtctc                                                 18

<210> SEQ ID NO 6
<211> LENGTH: 20
<212> TYPE: DNA
<213> ORGANISM: Homo sapiens

<400> SEQUENCE: 6
ctcctcccgg gtcaccttga                                               20

<210> SEQ ID NO 7
<211> LENGTH: 20
<212> TYPE: DNA
<213> ORGANISM: Homo sapiens

<400> SEQUENCE: 7
tctccggcgc agcaacagca                                               20

<210> SEQ ID NO 8
<211> LENGTH: 20
<212> TYPE: DNA
<213> ORGANISM: Homo sapiens

<400> SEQUENCE: 8
ccctcgcggc ggtggacagt                                               20

<210> SEQ ID NO 9
<211> LENGTH: 18
<212> TYPE: DNA
<213> ORGANISM: Rattus sp.

<400> SEQUENCE: 9
cccccaacct cacaaatg                                                 18

<210> SEQ ID NO 10
<211> LENGTH: 19
<212> TYPE: DNA
<213> ORGANISM: Rattus sp.

<400> SEQUENCE: 10
cacccaaccc agcccaaca                                                19

<210> SEQ ID NO 11
<211> LENGTH: 20
```

-continued

```
<212> TYPE: DNA
<213> ORGANISM: Rattus sp.

<400> SEQUENCE: 11
gggccatcat ccagaaccac                                                      20

<210> SEQ ID NO 12
<211> LENGTH: 20
<212> TYPE: DNA
<213> ORGANISM: Rattus sp.

<400> SEQUENCE: 12
aggccattgt ccacgcagag                                                      20

<210> SEQ ID NO 13
<211> LENGTH: 4808
<212> TYPE: DNA
<213> ORGANISM: Mus musculus
<220> FEATURE:
<221> NAME/KEY: CDS
<222> LOCATION: (36)..(4559)

<400> SEQUENCE: 13
gtctctgtcc tcgggtgaat ctggagccgt ggagg atg gag tcc ttg gac cgg          53
                                       Met Glu Ser Leu Asp Arg
                                         1               5 aga aga act ggc tct gag cag gag gag ggc ttt ggg gtg cag tca agg        101
Arg Arg Thr Gly Ser Glu Gln Glu Glu Gly Phe Gly Val Gln Ser Arg
             10                  15                  20 agg gcc act gac ctg ggc atg gtc ccc aat ctc cga cga agc aat agc        149
Arg Ala Thr Asp Leu Gly Met Val Pro Asn Leu Arg Arg Ser Asn Ser
         25                  30                  35 agc ctt tgc aag agc agg aga ttt ctg tgc tct ttc agc agt gag aag        197
Ser Leu Cys Lys Ser Arg Arg Phe Leu Cys Ser Phe Ser Ser Glu Lys
     40                  45                  50 caa gaa aac ctt agc tca tgg att ccc gag aat atc aag aag aag gag        245
Gln Glu Asn Leu Ser Ser Trp Ile Pro Glu Asn Ile Lys Lys Lys Glu
 55                  60                  65                  70 tgt gtg tac ttc gtg gaa agt tcc aaa ctc tcg gac gca ggg aag gta        293
Cys Val Tyr Phe Val Glu Ser Ser Lys Leu Ser Asp Ala Gly Lys Val
                 75                  80                  85 gtg tgt gcg tgt ggt tat acc cac gag caa cac ttg gag gtg gcc atc        341
Val Cys Ala Cys Gly Tyr Thr His Glu Gln His Leu Glu Val Ala Ile
             90                  95                 100 aag cca cac acc ttc cag ggc aag gag tgg gat cca aag aaa cac gtc        389
Lys Pro His Thr Phe Gln Gly Lys Glu Trp Asp Pro Lys Lys His Val
        105                 110                 115 caa gag atg ccc aca gat gcc ttt ggt gac atc gtt ttc aca gac ctg        437
Gln Glu Met Pro Thr Asp Ala Phe Gly Asp Ile Val Phe Thr Asp Leu
    120                 125                 130 agc cag aaa gtg ggg aag tat gtc cgg gtc tcc cag gac acg ccc tcc        485
Ser Gln Lys Val Gly Lys Tyr Val Arg Val Ser Gln Asp Thr Pro Ser
135                 140                 145                 150 agt gtc atc tac cag ctc atg acc cag cac tgg ggc cta gat gtc ccc        533
Ser Val Ile Tyr Gln Leu Met Thr Gln His Trp Gly Leu Asp Val Pro
                155                 160                 165 aac ctc ctc atc tcc gtg acc ggt ggg gcc aag aac ttc aac atg aag        581
Asn Leu Leu Ile Ser Val Thr Gly Gly Ala Lys Asn Phe Asn Met Lys
            170                 175                 180 ctg agg ctg aag agc atc ttc cgg aga ggc ttg gtc aag gtg gct caa        629
Leu Arg Leu Lys Ser Ile Phe Arg Arg Gly Leu Val Lys Val Ala Gln
        185                 190                 195
```

```
acc acg ggg gcc tgg atc atc act gga gga tcc cac aca ggc gtg atg      677
Thr Thr Gly Ala Trp Ile Ile Thr Gly Gly Ser His Thr Gly Val Met
200                 205                 210 aag cag gtg ggc gaa gcg gta cgg gac ttc agt ctg agc agc agc tgc      725
Lys Gln Val Gly Glu Ala Val Arg Asp Phe Ser Leu Ser Ser Ser Cys
215                 220                 225                 230 aaa gaa ggt gaa gtc atc act att ggc gta gcc acg tgg ggc acc atc      773
Lys Glu Gly Glu Val Ile Thr Ile Gly Val Ala Thr Trp Gly Thr Ile
                    235                 240                 245 cac aac cgc gag gga ctg atc cat ccc atg gga ggc ttc ccc gcc gag      821
His Asn Arg Glu Gly Leu Ile His Pro Met Gly Gly Phe Pro Ala Glu
                250                 255                 260 tac atg ctg gat gag gaa ggc caa ggg aac ctg acc tgc ttg gac agc      869
Tyr Met Leu Asp Glu Glu Gly Gln Gly Asn Leu Thr Cys Leu Asp Ser
            265                 270                 275 aac cat tcc cac ttc atc ttg gtg gat gat ggg acc cac ggg caa tat      917
Asn His Ser His Phe Ile Leu Val Asp Asp Gly Thr His Gly Gln Tyr
        280                 285                 290 ggt gtg gag att ccg ctg agg act aag ctg gaa aag ttc atc tca gag      965
Gly Val Glu Ile Pro Leu Arg Thr Lys Leu Glu Lys Phe Ile Ser Glu
295                 300                 305                 310 caa acg aag gaa agg gga ggt gtg gcc atc aag atc ccc att gtc tgc     1013
Gln Thr Lys Glu Arg Gly Gly Val Ala Ile Lys Ile Pro Ile Val Cys
                    315                 320                 325 gtg gtg ttg gag ggt ggc cct ggc act ctg cat aca atc tac aat gcc     1061
Val Val Leu Glu Gly Gly Pro Gly Thr Leu His Thr Ile Tyr Asn Ala
                330                 335                 340 atc aac aat ggc aca ccc tgc gtg ata gtg gag ggc tct ggc cga gtg     1109
Ile Asn Asn Gly Thr Pro Cys Val Ile Val Glu Gly Ser Gly Arg Val
            345                 350                 355 gct gac gtc atc gct cag gta gct act ctg cct gtc tct gag atc acc     1157
Ala Asp Val Ile Ala Gln Val Ala Thr Leu Pro Val Ser Glu Ile Thr
        360                 365                 370 atc tcc ttg atc cag cag aag ctc agc ata ttc ttc cag gag atg ttt     1205
Ile Ser Leu Ile Gln Gln Lys Leu Ser Ile Phe Phe Gln Glu Met Phe
375                 380                 385                 390 gag act ttc acc gaa aac cag att gtg gaa tgg acc aaa aag atc caa     1253
Glu Thr Phe Thr Glu Asn Gln Ile Val Glu Trp Thr Lys Lys Ile Gln
                    395                 400                 405 gac att gtc cgg agg cgg cag ctg ctg acg atc ttc cgg gaa ggc aag     1301
Asp Ile Val Arg Arg Arg Gln Leu Leu Thr Ile Phe Arg Glu Gly Lys
                410                 415                 420 gat ggt cag cag gat gtg gat gtg gcc att ctg cag gcg tta ctg aaa     1349
Asp Gly Gln Gln Asp Val Asp Val Ala Ile Leu Gln Ala Leu Leu Lys
            425                 430                 435 gcc tct cga agc caa gac cac ttt ggc cac gag aac tgg gac cac caa     1397
Ala Ser Arg Ser Gln Asp His Phe Gly His Glu Asn Trp Asp His Gln
        440                 445                 450 ctg aag ttg gct gtg gcc tgg aac cgc gtg gac atc gct cgc agt gag     1445
Leu Lys Leu Ala Val Ala Trp Asn Arg Val Asp Ile Ala Arg Ser Glu
455                 460                 465                 470 atc ttc acc gat gaa tgg cag tgg aag cct gca gat ctg cat ccc atg     1493
Ile Phe Thr Asp Glu Trp Gln Trp Lys Pro Ala Asp Leu His Pro Met
                    475                 480                 485 atg acg gcc gct ctc atc tcc aac aag cct gag ttc gtg agg ctc ttt     1541
Met Thr Ala Ala Leu Ile Ser Asn Lys Pro Glu Phe Val Arg Leu Phe
                490                 495                 500 ctg gag aat ggg gtg cgg ctc aag gag ttt gtc act tgg gat act ctt     1589
Leu Glu Asn Gly Val Arg Leu Lys Glu Phe Val Thr Trp Asp Thr Leu
```

```
                        505                 510                 515
ctc tgc ctg tac gag aac ctg gag ccg tcc tgt ctc ttc cac agc aag    1637
Leu Cys Leu Tyr Glu Asn Leu Glu Pro Ser Cys Leu Phe His Ser Lys
    520                 525                 530 cta cag aag gtg ctg gcc gaa gaa cag cgc tta gcc tat gca tct gca    1685
Leu Gln Lys Val Leu Ala Glu Glu Gln Arg Leu Ala Tyr Ala Ser Ala
535                 540                 545                 550 aca ccc cgc ctg cac atg cac cat gtg gcc cag gtg ctt cgt gaa ctc    1733
Thr Pro Arg Leu His Met His His Val Ala Gln Val Leu Arg Glu Leu
                555                 560                 565 ctg ggg gac tcc acg cag ctg ctg tac ccc cgg ccc cgg tac act gac    1781
Leu Gly Asp Ser Thr Gln Leu Leu Tyr Pro Arg Pro Arg Tyr Thr Asp
            570                 575                 580 agg cca cgg ctc tcg atg acc gtg cca cac atc aag ctg aac gtg cag    1829
Arg Pro Arg Leu Ser Met Thr Val Pro His Ile Lys Leu Asn Val Gln
        585                 590                 595 gga gtg agc ctc cgg tcc ctc tat aag cga tca aca ggc cac gtt acc    1877
Gly Val Ser Leu Arg Ser Leu Tyr Lys Arg Ser Thr Gly His Val Thr
    600                 605                 610 ttc acc att gac cca gtc cgt gac ctt ctc att tgg gcc gtt atc cag    1925
Phe Thr Ile Asp Pro Val Arg Asp Leu Leu Ile Trp Ala Val Ile Gln
615                 620                 625                 630 aac cac agg gag ctg gca ggc atc atc tgg gct cag agt cag gac tgt    1973
Asn His Arg Glu Leu Ala Gly Ile Ile Trp Ala Gln Ser Gln Asp Cys
                635                 640                 645 act gcc gca gca ctg gcc tgt agc aag atc ctg aag gag ctg tcc aag    2021
Thr Ala Ala Ala Leu Ala Cys Ser Lys Ile Leu Lys Glu Leu Ser Lys
            650                 655                 660 gag gag gaa gat aca gac agc tct gag gag atg ctg gca ctg gca gac    2069
Glu Glu Glu Asp Thr Asp Ser Ser Glu Glu Met Leu Ala Leu Ala Asp
        665                 670                 675 gag ttt gag cac aga gct ata ggc gtc ttc act gag tgc tac agg aag    2117
Glu Phe Glu His Arg Ala Ile Gly Val Phe Thr Glu Cys Tyr Arg Lys
    680                 685                 690 gat gag gaa aga gcc cag aag ctg ctt gtc cgt gtg tct gag gcc tgg    2165
Asp Glu Glu Arg Ala Gln Lys Leu Leu Val Arg Val Ser Glu Ala Trp
695                 700                 705                 710 ggg aag acc acc tgc ctg cag ctg gcc cta gag gcc aag gac atg aaa    2213
Gly Lys Thr Thr Cys Leu Gln Leu Ala Leu Glu Ala Lys Asp Met Lys
                715                 720                 725 ttc gtg tct cat gga ggc atc cag gct ttc cta acc aag gtg tgg tgg    2261
Phe Val Ser His Gly Gly Ile Gln Ala Phe Leu Thr Lys Val Trp Trp
            730                 735                 740 ggc cag ctc tgt gtg gac aat ggc ctg tgg agg atc atc ctg tgc atg    2309
Gly Gln Leu Cys Val Asp Asn Gly Leu Trp Arg Ile Ile Leu Cys Met
        745                 750                 755 ctg gcc ttc ccg ctg ctc ttc acc ggc ttc atc tcc ttc agg gaa aag    2357
Leu Ala Phe Pro Leu Leu Phe Thr Gly Phe Ile Ser Phe Arg Glu Lys
    760                 765                 770 agg ctg cag gca ctg tgt cgc cca gcc cgc gtc cgc gcc ttc ttc aat    2405
Arg Leu Gln Ala Leu Cys Arg Pro Ala Arg Val Arg Ala Phe Phe Asn
775                 780                 785                 790 gcg cct gtg gtc atc ttc cac atg aat atc ctc tcc tac ttt gcc ttc    2453
Ala Pro Val Val Ile Phe His Met Asn Ile Leu Ser Tyr Phe Ala Phe
                795                 800                 805 ctc tgc ctg ttc gcc tac gtg ctc atg gtg gac ttc cag cct tct cca    2501
Leu Cys Leu Phe Ala Tyr Val Leu Met Val Asp Phe Gln Pro Ser Pro
            810                 815                 820 tcc tgg tgc gag tac ctc atc tac ctg tgg ctc ttc tcc ctg gtg tgc    2549
```

```
Ser Trp Cys Glu Tyr Leu Ile Tyr Leu Trp Leu Phe Ser Leu Val Cys
        825                 830                 835 gaa gag act cgg cag cta ttc tat gat cct gat ggc tgt gga cta atg     2597
Glu Glu Thr Arg Gln Leu Phe Tyr Asp Pro Asp Gly Cys Gly Leu Met
840                 845                 850 aag atg gcg tcc ctg tac ttc agt gac ttc tgg aac aaa ctg gac gtt     2645
Lys Met Ala Ser Leu Tyr Phe Ser Asp Phe Trp Asn Lys Leu Asp Val
855                 860                 865                 870 ggg gcc att ctg ctc ttc ata gta gga ctg acc tgt cgg ctc atc cca     2693
Gly Ala Ile Leu Leu Phe Ile Val Gly Leu Thr Cys Arg Leu Ile Pro
                    875                 880                 885 gcg acg ctg tac cct ggg cgc atc atc ctg tct ttg gac ttc atc atg     2741
Ala Thr Leu Tyr Pro Gly Arg Ile Ile Leu Ser Leu Asp Phe Ile Met
                890                 895                 900 ttc tgt ctc cgt ctc atg cac atc ttc act att agc aag aca ctg ggg     2789
Phe Cys Leu Arg Leu Met His Ile Phe Thr Ile Ser Lys Thr Leu Gly
            905                 910                 915 ccc aag ata atc atc gtg aag cgg atg atg aag gac gtc ttc ttc ttc     2837
Pro Lys Ile Ile Ile Val Lys Arg Met Met Lys Asp Val Phe Phe Phe
        920                 925                 930 ctc ttt ctc ctg gcg gtg tgg gtg gtg tcc ttc ggc gta gct aag cag     2885
Leu Phe Leu Leu Ala Val Trp Val Val Ser Phe Gly Val Ala Lys Gln
935                 940                 945                 950 gcc att ctc ata cat aac gag agc cgc gtg gac tgg atc ttc cgt ggg     2933
Ala Ile Leu Ile His Asn Glu Ser Arg Val Asp Trp Ile Phe Arg Gly
                    955                 960                 965 gtt gtc tat cac tct tac ctg acc atc ttt ggc cag atc cca acc tac     2981
Val Val Tyr His Ser Tyr Leu Thr Ile Phe Gly Gln Ile Pro Thr Tyr
                970                 975                 980 att gac ggt gtg aat ttc agc atg gac cag tgc agc ccc aat ggc acg     3029
Ile Asp Gly Val Asn Phe Ser Met Asp Gln Cys Ser Pro Asn Gly Thr
            985                 990                 995 gac ccc tac aag cct aag tgt cct gag agc gac tgg acg gga cag gca     3077
Asp Pro Tyr Lys Pro Lys Cys Pro Glu Ser Asp Trp Thr Gly Gln Ala
        1000                1005                1010 cct gcc ttc ccc gag tgg ctg act gtc acc ctg ctc tgc ctc tac ctg     3125
Pro Ala Phe Pro Glu Trp Leu Thr Val Thr Leu Leu Cys Leu Tyr Leu
1015                1020                1025                1030 ctc ttt gcc aac atc ctg ctg ctt aac ctg ctc atc gcc atg ttc aac     3173
Leu Phe Ala Asn Ile Leu Leu Leu Asn Leu Leu Ile Ala Met Phe Asn
                    1035                1040                1045 tac acc ttc cag gag gtg cag gaa cac aca gac cag atc tgg aaa ttc     3221
Tyr Thr Phe Gln Glu Val Gln Glu His Thr Asp Gln Ile Trp Lys Phe
                1050                1055                1060 cag cgc cac gac ctg atc gag gag tac cat ggc cgt ccc ccg gca cct     3269
Gln Arg His Asp Leu Ile Glu Glu Tyr His Gly Arg Pro Pro Ala Pro
            1065                1070                1075 ccc cca ctc atc ctc ctc agc cac ctg cag ctc ctg atc aag agg att     3317
Pro Pro Leu Ile Leu Leu Ser His Leu Gln Leu Leu Ile Lys Arg Ile
        1080                1085                1090 gtc ctg aag atc cct gcc aag agg cat aag cag ctc aag aac aag ctg     3365
Val Leu Lys Ile Pro Ala Lys Arg His Lys Gln Leu Lys Asn Lys Leu
1095                1100                1105                1110 gag aag aac gag gag aca gcg ctc ctg tct tgg gaa ctg tac ctg aag     3413
Glu Lys Asn Glu Glu Thr Ala Leu Leu Ser Trp Glu Leu Tyr Leu Lys
                    1115                1120                1125 gag aac tac ctg cag aac cag cag tac cag cag aaa cag cgt cca gag     3461
Glu Asn Tyr Leu Gln Asn Gln Gln Tyr Gln Gln Lys Gln Arg Pro Glu
                1130                1135                1140
```

-continued

| | | |
|---|---|---|
| cag aaa atc caa gac atc agt gag aaa gtg gac acc atg gtg gat ctg<br>Gln Lys Ile Gln Asp Ile Ser Glu Lys Val Asp Thr Met Val Asp Leu<br>     1145                    1150                    1155 | | 3509 |
| ctg gac atg gac cag gtg aag agg tca ggc tcc aca gag cag aga ctg<br>Leu Asp Met Asp Gln Val Lys Arg Ser Gly Ser Thr Glu Gln Arg Leu<br>1160                    1165                    1170 | | 3557 |
| gct tcc ctg gag gaa cag gtg act cag gtg acc aga gct ttg cac tgg<br>Ala Ser Leu Glu Glu Gln Val Thr Gln Val Thr Arg Ala Leu His Trp<br>1175                    1180                    1185                    1190 | | 3605 |
| atc gtg aca acc ctg aag gac agt ggc ttt ggc tca gga gca ggt gcg<br>Ile Val Thr Thr Leu Lys Asp Ser Gly Phe Gly Ser Gly Ala Gly Ala<br>                    1195                    1200                    1205 | | 3653 |
| ctg acc ctg gca ccc cag agg gcc ttc gat gag cca gat gct gag ctg<br>Leu Thr Leu Ala Pro Gln Arg Ala Phe Asp Glu Pro Asp Ala Glu Leu<br>1210                    1215                    1220 | | 3701 |
| agt atc agg agg aaa gta gag gaa cca gga gat ggt tac cac gtg agc<br>Ser Ile Arg Arg Lys Val Glu Glu Pro Gly Asp Gly Tyr His Val Ser<br>1225                    1230                    1235 | | 3749 |
| gcc cgg cat ctc ctc tat ccc aat gcc cgc atc atg cgc ttc ccc gtg<br>Ala Arg His Leu Leu Tyr Pro Asn Ala Arg Ile Met Arg Phe Pro Val<br>                    1240                    1245                    1250 | | 3797 |
| cct aac gag aag gtg cct tgg gcg gca gag ttt ctg atc tac gat cct<br>Pro Asn Glu Lys Val Pro Trp Ala Ala Glu Phe Leu Ile Tyr Asp Pro<br>1255                    1260                    1265                    1270 | | 3845 |
| ccc ttt tac acc gct gag aag gat gtg gct ctc aca gac ccc gtg gga<br>Pro Phe Tyr Thr Ala Glu Lys Asp Val Ala Leu Thr Asp Pro Val Gly<br>                    1275                    1280                    1285 | | 3893 |
| gac act gca gaa cct ctg tct aag atc agt tac aac gtc gtg gat gga<br>Asp Thr Ala Glu Pro Leu Ser Lys Ile Ser Tyr Asn Val Val Asp Gly<br>1290                    1295                    1300 | | 3941 |
| ccg acg gac cgt cgc agc ttc cat gga gtc tac gtg gtc gag tat ggg<br>Pro Thr Asp Arg Arg Ser Phe His Gly Val Tyr Val Val Glu Tyr Gly<br>                    1305                    1310                    1315 | | 3989 |
| ttc ccg tgt gaa ccc cat ggg ccg cga cag ggt tgc tgt ggt cgt ggg<br>Phe Pro Cys Glu Pro His Gly Pro Arg Gln Gly Cys Cys Gly Arg Gly<br>1320                    1325                    1330 | | 4037 |
| agc ctc agc tgg ttt ggt ccc aac cac act ctg cag cca gtt gtc acc<br>Ser Leu Ser Trp Phe Gly Pro Asn His Thr Leu Gln Pro Val Val Thr<br>1335                    1340                    1345                    1350 | | 4085 |
| cgg tgg aag agg aac cag ggt gga gcc atc tgc cgg aag agt gtc agg<br>Arg Trp Lys Arg Asn Gln Gly Gly Ala Ile Cys Arg Lys Ser Val Arg<br>                    1355                    1360                    1365 | | 4133 |
| aag atg ctg gag gtg cta gtg atg aag ctg cct cgc tct gag cac tgg<br>Lys Met Leu Glu Val Leu Val Met Lys Leu Pro Arg Ser Glu His Trp<br>1370                    1375                    1380 | | 4181 |
| gcc ttg cct ggg ggc tct agg gag cca ggg gag atg cta cca cgg aag<br>Ala Leu Pro Gly Gly Ser Arg Glu Pro Gly Glu Met Leu Pro Arg Lys<br>1385                    1390                    1395 | | 4229 |
| ctg aaa cgg gtc ctc cgg cag gag ttc tgg gtg gcc ttt gag acc ttg<br>Leu Lys Arg Val Leu Arg Gln Glu Phe Trp Val Ala Phe Glu Thr Leu<br>                    1400                    1405                    1410 | | 4277 |
| ctg atg caa ggt aca gag gta tac aaa ggg tac gtg gat gac cca agg<br>Leu Met Gln Gly Thr Glu Val Tyr Lys Gly Tyr Val Asp Asp Pro Arg<br>1415                    1420                    1425                    1430 | | 4325 |
| aac aca gac aat gcc tgg atc gag aca gtg gct gtc agc atc cat ttt<br>Asn Thr Asp Asn Ala Trp Ile Glu Thr Val Ala Val Ser Ile His Phe<br>                    1435                    1440                    1445 | | 4373 |
| cag gac cag aat gat atg gag ctg aag agg ctg gaa gag aac ctg cac<br>Gln Asp Gln Asn Asp Met Glu Leu Lys Arg Leu Glu Glu Asn Leu His<br>1450                    1455                    1460 | | 4421 |

-continued

| | |
|---|---|
| act cat gat cca aag gag ttg acc cgt gac ctg aag ctg tct act gaa<br>Thr His Asp Pro Lys Glu Leu Thr Arg Asp Leu Lys Leu Ser Thr Glu<br>                          1465                     1470                   1475 | 4469 |
| tgg cag gtg gta gac cgg cgg atc cct ctg tat gcg aac cac aag acc<br>Trp Gln Val Val Asp Arg Arg Ile Pro Leu Tyr Ala Asn His Lys Thr<br>       1480                   1485                   1490 | 4517 |
| atc ctc cag aag gtg gcc tca ctg ttt gga gct cac ttc tga<br>Ile Leu Gln Lys Val Ala Ser Leu Phe Gly Ala His Phe<br>1495                   1500                   1505 | 4559 |
| ctgtggcttc tgggccacaa tggccccca agacttggac tgctgtcttg ggctggatgg | 4619 |
| ctggttgggg tactgggttg gggtgggtgg taggttgtag ggctgggttg ggtgaccaca | 4679 |
| gggatcttaa taagtcccca gaggtgatgt cctgaaagcc acttctgcca caacaggaag | 4739 |
| gtcacaagca taaggacaga agtgtattca gtggctcctg ctacctatgt cctcaagtgc | 4799 |
| catgctttg | 4808 |

<210> SEQ ID NO 14
<211> LENGTH: 1507
<212> TYPE: PRT
<213> ORGANISM: Mus musculus

<400> SEQUENCE: 14

Met Glu Ser Leu Asp Arg Arg Thr Gly Ser Glu Gln Glu Glu Gly
1               5                   10                  15

Phe Gly Val Gln Ser Arg Arg Ala Thr Asp Leu Gly Met Val Pro Asn
                20                  25                  30

Leu Arg Arg Ser Asn Ser Ser Leu Cys Lys Ser Arg Arg Phe Leu Cys
            35                  40                  45

Ser Phe Ser Ser Glu Lys Gln Glu Asn Leu Ser Ser Trp Ile Pro Glu
        50                  55                  60

Asn Ile Lys Lys Lys Glu Cys Val Tyr Phe Val Glu Ser Ser Lys Leu
65                  70                  75                  80

Ser Asp Ala Gly Lys Val Val Cys Ala Cys Gly Tyr Thr His Glu Gln
                85                  90                  95

His Leu Glu Val Ala Ile Lys Pro His Thr Phe Gln Gly Lys Glu Trp
            100                 105                 110

Asp Pro Lys Lys His Val Gln Glu Met Pro Thr Asp Ala Phe Gly Asp
        115                 120                 125

Ile Val Phe Thr Asp Leu Ser Gln Lys Val Gly Lys Tyr Val Arg Val
    130                 135                 140

Ser Gln Asp Thr Pro Ser Ser Val Ile Tyr Gln Leu Met Thr Gln His
145                 150                 155                 160

Trp Gly Leu Asp Val Pro Asn Leu Leu Ile Ser Val Thr Gly Gly Ala
                165                 170                 175

Lys Asn Phe Asn Met Lys Leu Arg Leu Lys Ser Ile Phe Arg Arg Gly
            180                 185                 190

Leu Val Lys Val Ala Gln Thr Thr Gly Ala Trp Ile Ile Thr Gly Gly
        195                 200                 205

Ser His Thr Gly Val Met Lys Gln Val Gly Glu Ala Val Arg Asp Phe
    210                 215                 220

Ser Leu Ser Ser Ser Cys Lys Glu Gly Glu Val Ile Thr Ile Gly Val
225                 230                 235                 240

Ala Thr Trp Gly Thr Ile His Asn Arg Glu Gly Leu Ile His Pro Met
                245                 250                 255

```
Gly Gly Phe Pro Ala Glu Tyr Met Leu Asp Glu Glu Gly Gln Gly Asn
            260                 265                 270

Leu Thr Cys Leu Asp Ser Asn His Ser His Phe Ile Leu Val Asp Asp
            275                 280                 285

Gly Thr His Gly Gln Tyr Gly Val Glu Ile Pro Leu Arg Thr Lys Leu
            290                 295                 300

Glu Lys Phe Ile Ser Glu Gln Thr Lys Glu Arg Gly Gly Val Ala Ile
305                 310                 315                 320

Lys Ile Pro Ile Val Cys Val Val Leu Glu Gly Gly Pro Gly Thr Leu
                    325                 330                 335

His Thr Ile Tyr Asn Ala Ile Asn Asn Gly Thr Pro Cys Val Ile Val
                340                 345                 350

Glu Gly Ser Gly Arg Val Ala Asp Val Ile Ala Gln Val Ala Thr Leu
                355                 360                 365

Pro Val Ser Glu Ile Thr Ile Ser Leu Ile Gln Gln Lys Leu Ser Ile
            370                 375                 380

Phe Phe Gln Glu Met Phe Glu Thr Phe Thr Glu Asn Gln Ile Val Glu
385                 390                 395                 400

Trp Thr Lys Lys Ile Gln Asp Ile Val Arg Arg Gln Leu Leu Thr
                    405                 410                 415

Ile Phe Arg Glu Gly Lys Asp Gly Gln Gln Asp Val Asp Val Ala Ile
                420                 425                 430

Leu Gln Ala Leu Leu Lys Ala Ser Arg Ser Gln Asp His Phe Gly His
                435                 440                 445

Glu Asn Trp Asp His Gln Leu Lys Leu Ala Val Ala Trp Asn Arg Val
450                 455                 460

Asp Ile Ala Arg Ser Glu Ile Phe Thr Asp Glu Trp Gln Trp Lys Pro
465                 470                 475                 480

Ala Asp Leu His Pro Met Met Thr Ala Ala Leu Ile Ser Asn Lys Pro
                485                 490                 495

Glu Phe Val Arg Leu Phe Leu Glu Asn Gly Val Arg Leu Lys Glu Phe
                500                 505                 510

Val Thr Trp Asp Thr Leu Leu Cys Leu Tyr Glu Asn Leu Glu Pro Ser
            515                 520                 525

Cys Leu Phe His Ser Lys Leu Gln Lys Val Leu Ala Glu Glu Gln Arg
            530                 535                 540

Leu Ala Tyr Ala Ser Ala Thr Pro Arg Leu His Met His His Val Ala
545                 550                 555                 560

Gln Val Leu Arg Glu Leu Leu Gly Asp Ser Thr Gln Leu Leu Tyr Pro
                565                 570                 575

Arg Pro Arg Tyr Thr Asp Arg Pro Arg Leu Ser Met Thr Val Pro His
                580                 585                 590

Ile Lys Leu Asn Val Gln Gly Val Ser Leu Arg Ser Leu Tyr Lys Arg
                595                 600                 605

Ser Thr Gly His Val Thr Phe Thr Ile Asp Pro Val Arg Asp Leu Leu
            610                 615                 620

Ile Trp Ala Val Ile Gln Asn His Arg Glu Leu Ala Gly Ile Ile Trp
625                 630                 635                 640

Ala Gln Ser Gln Asp Cys Thr Ala Ala Leu Ala Cys Ser Lys Ile
                    645                 650                 655

Leu Lys Glu Leu Ser Lys Glu Glu Asp Thr Asp Ser Ser Glu Glu
                660                 665                 670

Met Leu Ala Leu Ala Asp Glu Phe Glu His Arg Ala Ile Gly Val Phe
```

```
                675                 680                 685
Thr Glu Cys Tyr Arg Lys Asp Glu Glu Arg Ala Gln Lys Leu Leu Val
    690                 695                 700
Arg Val Ser Glu Ala Trp Gly Lys Thr Thr Cys Leu Gln Leu Ala Leu
705                 710                 715                 720
Glu Ala Lys Asp Met Lys Phe Val Ser His Gly Gly Ile Gln Ala Phe
                725                 730                 735
Leu Thr Lys Val Trp Trp Gly Gln Leu Cys Val Asp Asn Gly Leu Trp
            740                 745                 750
Arg Ile Ile Leu Cys Met Leu Ala Phe Pro Leu Leu Phe Thr Gly Phe
        755                 760                 765
Ile Ser Phe Arg Glu Lys Arg Leu Gln Ala Leu Cys Arg Pro Ala Arg
    770                 775                 780
Val Arg Ala Phe Phe Asn Ala Pro Val Val Ile Phe His Met Asn Ile
785                 790                 795                 800
Leu Ser Tyr Phe Ala Phe Leu Cys Leu Phe Ala Tyr Val Leu Met Val
                805                 810                 815
Asp Phe Gln Pro Ser Pro Ser Trp Cys Glu Tyr Leu Ile Tyr Leu Trp
            820                 825                 830
Leu Phe Ser Leu Val Cys Glu Glu Thr Arg Gln Leu Phe Tyr Asp Pro
        835                 840                 845
Asp Gly Cys Gly Leu Met Lys Met Ala Ser Leu Tyr Phe Ser Asp Phe
    850                 855                 860
Trp Asn Lys Leu Asp Val Gly Ala Ile Leu Leu Phe Ile Val Gly Leu
865                 870                 875                 880
Thr Cys Arg Leu Ile Pro Ala Thr Leu Tyr Pro Gly Arg Ile Ile Leu
                885                 890                 895
Ser Leu Asp Phe Ile Met Phe Cys Leu Arg Leu Met His Ile Phe Thr
            900                 905                 910
Ile Ser Lys Thr Leu Gly Pro Lys Ile Ile Val Lys Arg Met Met
        915                 920                 925
Lys Asp Val Phe Phe Phe Leu Phe Leu Leu Ala Val Trp Val Val Ser
    930                 935                 940
Phe Gly Val Ala Lys Gln Ala Ile Leu Ile His Asn Glu Ser Arg Val
945                 950                 955                 960
Asp Trp Ile Phe Arg Gly Val Val Tyr His Ser Tyr Leu Thr Ile Phe
                965                 970                 975
Gly Gln Ile Pro Thr Tyr Ile Asp Gly Val Asn Phe Ser Met Asp Gln
            980                 985                 990
Cys Ser Pro Asn Gly Thr Asp Pro Tyr Lys Pro Lys Cys Pro Glu Ser
        995                 1000                1005
Asp Trp Thr Gly Gln Ala Pro Ala Phe Pro Glu Trp Leu Thr Val Thr
    1010                1015                1020
Leu Leu Cys Leu Tyr Leu Leu Phe Ala Asn Ile Leu Leu Asn Leu
1025                1030                1035                1040
Leu Ile Ala Met Phe Asn Tyr Thr Phe Gln Glu Val Gln Glu His Thr
                1045                1050                1055
Asp Gln Ile Trp Lys Phe Gln Arg His Asp Leu Ile Glu Glu Tyr His
            1060                1065                1070
Gly Arg Pro Pro Ala Pro Pro Pro Leu Ile Leu Leu Ser His Leu Gln
        1075                1080                1085
Leu Leu Ile Lys Arg Ile Val Leu Lys Ile Pro Ala Lys Arg His Lys
    1090                1095                1100
```

```
Gln Leu Lys Asn Lys Leu Glu Lys Asn Glu Thr Ala Leu Leu Ser
1105                1110                1115                1120

Trp Glu Leu Tyr Leu Lys Glu Asn Tyr Leu Gln Asn Gln Gln Tyr Gln
            1125                1130                1135

Gln Lys Gln Arg Pro Glu Gln Lys Ile Gln Asp Ile Ser Glu Lys Val
            1140                1145                1150

Asp Thr Met Val Asp Leu Leu Asp Met Asp Gln Val Lys Arg Ser Gly
            1155                1160                1165

Ser Thr Glu Gln Arg Leu Ala Ser Leu Glu Glu Gln Val Thr Gln Val
            1170                1175                1180

Thr Arg Ala Leu His Trp Ile Val Thr Thr Leu Lys Asp Ser Gly Phe
1185                1190                1195                1200

Gly Ser Gly Ala Gly Ala Leu Thr Leu Ala Pro Gln Arg Ala Phe Asp
                1205                1210                1215

Glu Pro Asp Ala Glu Leu Ser Ile Arg Arg Lys Val Glu Glu Pro Gly
                1220                1225                1230

Asp Gly Tyr His Val Ser Ala Arg His Leu Leu Tyr Pro Asn Ala Arg
                1235                1240                1245

Ile Met Arg Phe Pro Val Pro Asn Glu Lys Val Pro Trp Ala Ala Glu
            1250                1255                1260

Phe Leu Ile Tyr Asp Pro Pro Phe Tyr Thr Ala Glu Lys Asp Val Ala
1265                1270                1275                1280

Leu Thr Asp Pro Val Gly Asp Thr Ala Glu Pro Leu Ser Lys Ile Ser
                1285                1290                1295

Tyr Asn Val Val Asp Gly Pro Thr Asp Arg Arg Ser Phe His Gly Val
                1300                1305                1310

Tyr Val Val Glu Tyr Gly Phe Pro Cys Glu Pro His Gly Pro Arg Gln
            1315                1320                1325

Gly Cys Cys Gly Arg Gly Ser Leu Ser Trp Phe Gly Pro Asn His Thr
            1330                1335                1340

Leu Gln Pro Val Val Thr Arg Trp Lys Arg Asn Gln Gly Gly Ala Ile
1345                1350                1355                1360

Cys Arg Lys Ser Val Arg Lys Met Leu Glu Val Leu Val Met Lys Leu
            1365                1370                1375

Pro Arg Ser Glu His Trp Ala Leu Pro Gly Gly Ser Arg Glu Pro Gly
            1380                1385                1390

Glu Met Leu Pro Arg Lys Leu Lys Arg Val Leu Arg Gln Glu Phe Trp
            1395                1400                1405

Val Ala Phe Glu Thr Leu Leu Met Gln Gly Thr Glu Val Tyr Lys Gly
            1410                1415                1420

Tyr Val Asp Asp Pro Arg Asn Thr Asp Asn Ala Trp Ile Glu Thr Val
1425                1430                1435                1440

Ala Val Ser Ile His Phe Gln Asp Gln Asn Asp Met Glu Leu Lys Arg
            1445                1450                1455

Leu Glu Glu Asn Leu His Thr His Asp Pro Lys Glu Leu Thr Arg Asp
            1460                1465                1470

Leu Lys Leu Ser Thr Glu Trp Gln Val Val Asp Arg Arg Ile Pro Leu
            1475                1480                1485

Tyr Ala Asn His Lys Thr Ile Leu Gln Lys Val Ala Ser Leu Phe Gly
            1490                1495                1500

Ala His Phe
1505
```

```
<210> SEQ ID NO 15
<211> LENGTH: 20
<212> TYPE: DNA
<213> ORGANISM: Mus musculus

<400> SEQUENCE: 15
gtctctgtcc tcgggtgaat                                                    20

<210> SEQ ID NO 16
<211> LENGTH: 20
<212> TYPE: DNA
<213> ORGANISM: Mus musculus

<400> SEQUENCE: 16
caaagcatgg cacttgagga                                                    20

<210> SEQ ID NO 17
<211> LENGTH: 18
<212> TYPE: DNA
<213> ORGANISM: Mus musculus

<400> SEQUENCE: 17
tctatcccaa tgcccgca                                                      18

<210> SEQ ID NO 18
<211> LENGTH: 18
<212> TYPE: DNA
<213> ORGANISM: Mus musculus

<400> SEQUENCE: 18
aaactctgcc gcccaagg                                                      18
```